(12) United States Patent
Yamamoto et al.

(10) Patent No.: US 7,582,463 B2
(45) Date of Patent: Sep. 1, 2009

(54) NON-REDUCING SACCHARIDE-FORMING ENZYME, TREHALOSE-RELEASING ENZYME, AND PROCESS FOR PRODUCING SACCHARIDES USING THE ENZYMES

(75) Inventors: Takuo Yamamoto, Okayama (JP); Kazuhiko Maruta, Okayama (JP); Michio Kubota, Okayama (JP); Shigeharu Fukuda, Okayama (JP); Toshio Miyake, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 0 days.

(21) Appl. No.: 11/564,476

(22) Filed: Nov. 29, 2006

(65) Prior Publication Data
US 2007/0281346 A1 Dec. 6, 2007

Related U.S. Application Data

(60) Division of application No. 09/435,770, filed on Nov. 8, 1999, now Pat. No. 7,186,535, which is a continuation-in-part of application No. 09/392,253, filed on Sep. 9, 1999, now abandoned.

(30) Foreign Application Priority Data

Sep. 11, 1998 (JP) .............................. 1998-258394
Dec. 11, 1998 (JP) .............................. 1998-352252
Jan. 26, 1999 (JP) .............................. 1999-016931

(51) Int. Cl.
*C12N 9/00* (2006.01)
*C12N 9/24* (2006.01)
*C12N 9/26* (2006.01)
*C12N 1/20* (2006.01)
*C12N 15/00* (2006.01)
*C07H 21/04* (2006.01)

(52) U.S. Cl. ................. 435/201; 435/183; 435/200; 435/252.3; 435/320.1; 536/23.2

(58) Field of Classification Search ................ 435/183, 435/193, 200, 252.3, 320.1; 536/23.2
See application file for complete search history.

(56) References Cited

U.S. PATENT DOCUMENTS

| 4,521,252 | A | 6/1985 | Miyake et al. |
| RE33,047 | E | 9/1989 | Miyake et al. |

FOREIGN PATENT DOCUMENTS

| EP | 0 606 753 | 7/1994 |
| EP | 0 628 630 | 12/1994 |
| EP | 0 671 470 | 9/1995 |
| EP | 0 674 005 | 9/1995 |
| EP | 0674005 A2 | 9/1995 |
| EP | 0 688 867 | 12/1995 |
| EP | 0 690 130 | 1/1996 |
| EP | 0 690 131 | 1/1996 |
| EP | 0 691 407 | 1/1996 |
| EP | 0 693 558 | 1/1996 |
| EP | 0 697 461 | 2/1996 |
| EP | 0 709 461 | 5/1996 |
| EP | 0 764 720 | 3/1997 |
| EP | 0 813 820 | 12/1997 |
| EP | 0 834 516 | 4/1998 |
| EP | 0 850 947 | 7/1998 |
| EP | 0 868 916 | 10/1998 |
| EP | 0 882 408 | 12/1998 |
| EP | 0 925 719 | 6/1999 |
| JP | 58-23799 | 2/1983 |
| JP | 58-72598 | 4/1983 |
| JP | 63-157987 | 6/1988 |
| JP | 5-502162 | 4/1993 |
| JP | 7-143876 | 6/1995 |
| JP | 7-213283 | 8/1995 |
| JP | 7-298880 | 11/1995 |
| JP | 7-322883 | 12/1995 |
| JP | 8-66187 | 3/1996 |
| JP | 8-66188 | 3/1996 |
| JP | 8-73482 | 3/1996 |
| JP | 8-73504 | 3/1996 |
| JP | 8-73506 | 3/1996 |
| JP | 8-84586 | 4/1996 |
| JP | 8-506731 | 7/1996 |
| JP | 2576970 | 11/1996 |
| JP | 8-336363 | 12/1996 |
| JP | 8-336388 | 12/1996 |
| JP | 9-9986 | 1/1997 |
| JP | 9-500024 | 1/1997 |
| JP | 9-500543 | 1/1997 |
| JP | 9-154493 | 6/1997 |
| JP | 9-252719 | 9/1997 |
| JP | 10-66540 | 3/1998 |
| JP | 10-165118 | 6/1998 |
| JP | 10-168093 | 6/1998 |
| JP | 11-46717 | 2/1999 |
| JP | 11-60590 | 3/1999 |
| JP | 11-75686 | 3/1999 |

(Continued)

OTHER PUBLICATIONS

Kato et al. Accession AAR90620, published Jun. 29, 1996 (Alignment to SEQ ID No. 10).*

(Continued)

*Primary Examiner*—Christian L Fronda
(74) *Attorney, Agent, or Firm*—Browdy and Neimark, PLLC

(57) ABSTRACT

A non-reducing saccharide-forming enzyme and a trehalose-releasing enzyme, which have an optimum temperature in a medium temperature range, i.e., a temperature of over 40 or 45° C. but below 60° C.; and an optimum pH in an acid pH range, i.e., a pH of less than 7. The two-types of enzymes can be obtained in a desired amount, for example, by culturing in a nutrient culture medium microorganisms capable of producing the enzymes or by recombinant DNA technology.

13 Claims, 9 Drawing Sheets

FOREIGN PATENT DOCUMENTS

| JP | 11-75763 | 3/1999 |
|---|---|---|
| JP | 11-158075 | 6/1999 |
| JP | 11-263795 | 9/1999 |
| JP | 11-308983 | 11/1999 |
| WO | WO 95/34642 | 12/1995 |

OTHER PUBLICATIONS

Kato et al. Accession AAR90620, published Jun. 29, 1996 (Alignment to SEQ ID No. 12).*

Barry et al. Accession AAR92695, published Jun. 3, 1996.*

Kato et al. Accession AAR90658, published Jul. 13, 1996.*

Chica et al. Curr Opin Biotechnol. Aug. 2005;16(4):378-84.*

*Chemical Abstracts*, 105(21):185270; 105:185265t; Diderichsen Eur. Pat. Appln. EP 185,512, "Stabilizing extra-chromosomal elements in bacteria during cultivation, extra-chromosomal elements, transformed bacteria and a method of producing a desired product in transformed bacteria" (1986).

*Chemical Abstracts*, 109(3):179; 109:18173n; Hastrup Eur. Pat. Appln. EP 242,220, "Xylose-inducible cloning vectors for *Bacillus subtilis*" (1988).

*Chemical Abstracts*, 115(11):255; 115:107773z; Joergensen PCT Int. Appln. WO 91 09,129, "Stable integration of DNA in bacterial genomes" (1991).

*Chemical Abstracts*, 121(19):343-343; 121:223663m; Joergensen PCT Int. Appln. WO 94 19,454, "Cloning and expression of Pyrococcus alpha-amylase gene and use of enzyme in starch degradation" (1994).

*Chemical Abstracts*, 122(17):927; 122;212617u; Wassermann PCT Int. Appln. WO 95 04,462, Protein concentrations in rye-flour (1995).

*Chemical Abstracts*, 123(17):341; 123d:220286w, Berka, PCT Appln. No. WO 95 15,391, "*Aspergillus* expression systems for production of cellulase, lipases, peroxidase, and xylanase" (1995).

Hasegawa (Ed.), "Biseibutsu-no-Bunrui-to-Dotei" (Classification and Identification of Microorganisms), Japan Scientific Societies Press, Tokyo, Japan (1985).

Horton et al, "Gene Splicing by Overlap Extension", *Methods in Enzymology* 217:270-279 (1993).

Lipman et al, "Rapid and Sensitive Protein Similarity Searches", *Science*, 227:1435-1441 (1985).

Matsumura et al (Eds), "Jikken-Igaku-Bessatsu-Shin-Idennshi-Kogaku-Handbook" (Handbook of Genetic Engineering), Yodosha Co., Ltd,, Tokyo, Japan, pp. 269-283 (1996).

Riazuddin, S., "Plant Genetic Engineering and Future Agriculture" in *Genetic Engineering: Principles and Methods*, vol. 16, Setlow (Ed.), Plenum Press, New York and London, pp. 93-113 (1994).

Sambrook et al (Eds.), *Molecular Cloning: A Laboratory Manual*, $2^{nd}$. Ed., Cold Spring Harbor Laboratory Press, Cold Spring Harbor, NY (1989).

Sneath et al (Eds.), *Bergey's Manual of Systematic Bacteriology*, vol. 2, Wiliams & Wilkins, Baltimore, MD, pp. 1291-1301 (1984).

*Handbook of Amylases and Related Enzymes*, Ed. The Amylase Research Society of Japan, Pergamon Press, pp. 18-142 (1988).

Oiiguciii et al., "Purification and Properties of Trehalose-Synthesizing Enzyme from *Pseudomonas* sp. F1", *Journal of Fermentation and Bioengineering*, 84:4:358-360 (1997).

Nakada et al., *Biosci Biotechnol. Biochem.*, 59(12) :2215-8 (Abstract) (Dec. 1995).

* cited by examiner

NON-REDUCING SACCHARIDE-FORMING ENZYME, TREHALOSE-RELEASING ENZYME, AND PROCESS FOR PRODUCING SACCHARIDES USING THE ENZYMES

CROSS REFERENCE TO RELATED APPLICATION

This application is a continuation-in-part of copending parent application Ser. No. 09/392,253, filed Sep. 9, 1999, the entire contents of which being hereby incorporated herein by reference.

BACKGROUND OF THE INVENTION

1. Field of the Invention

The present invention relates to a non-reducing saccharide-forming enzyme, a trehalose-releasing enzyme, and a process for producing saccharides using the enzymes.

2. Description of the Prior Art

Trehalose is a disaccharide consisting of two moles of glucose bound at their reducing residues, and is widely found in nature, for example in microorganisms, fungi, algae, insects, Crustacea, etc. Since the saccharide has long been known as a useful saccharide substantially free of reducibility and having a satisfactory moisture-retaining action, it has been expected to use in extensive fields including foods, cosmetics, and pharmaceuticals. However, no efficient production of the saccharide was established, and this narrows the use of trehalose in spite of its outstanding expectation. Thus supply of trehalose in a lower cost is greatly expected.

As a proposal for such an expectation, the present inventors had already established a process for enzymatically producing trehalose from material starches through their energetic studies. The process is characterized by a step of subjecting reducing partial starch hydrolysates to the action of a non-reducing saccharide-forming enzyme, which forms a non-reducing saccharide having a trehalose structure as an end unit from reducing partial starch hydrolysates, and to the action of a trehalose-releasing enzyme which acts on a non-reducing saccharide having a trehalose structure as an end unit in order to hydrolyze and release trehalose from the rest of the non-reducing saccharide. These enzymes and processes thereof are disclosed in Japanese Patent Kokai Nos. 143,876/95, 213,283/95, 322,883/95, 298,880/95, 66,187/96, 66,188/96, 73,504/96, 84,586/96, and 336,388/96, applied for by the same applicant as the present invention. Thus, a low-cost production of trehalose was attained.

During the studies, they found an original finding that the non-reducing saccharide-forming enzyme can be applied for a novel production of non-reducing saccharides that can overcome conventional drawback residing in reducing partial starch hydrolysates. As a problem, reducing partial starch hydrolysates such as dextrins and maltooligosaccharides have advantageous features that they can be used as sweeteners and energy-supplementing saccharide sources, but as a demerit they are highly reactive with substances because of their reducibility and are susceptible to browning reaction when coexisted with amino acids and/or proteins and to readily deteriorate their quality. To overcome such a problem, it is only known a method to convert reducing partial starch hydrolysates into sugar alcohols using a high-pressure hydrogenation method, etc. In actual use, the method, however, needs much heats and instruments constructed under consideration of safety in view of the use of hydrogen, resulting in a higher cost and much labor cost. On the contrary, the aforesaid non-reducing saccharide-forming enzyme as mentioned previously acts on reducing partial starch hydrolysates and forms non-reducing saccharide having a trehalose structure as an end unit, and the reaction proceeds under a relatively-mild condition due to its enzymatic reaction. Using the action of the enzyme, the present inventors established a novel efficient process for non-reducing saccharides using the enzyme, that can overcome conventional drawback residing in reducing partial starch hydrolysates. Because of these findings, the development of applicable uses for trehalose and non-reducing saccharides have become to be flourished in various fields, and this diversifies the uses of these saccharides and now remarkably increases the demands of the saccharides in a wide variety of fields.

Under these circumstances, a more efficient process for producing trehalose and non-reducing saccharides having a trehalose structure has been more expected in this art. A key to such an expectation is to establish a non-reducing saccharide-forming enzyme and a trehalose-releasing enzyme with various optimum conditions, and to provide a wide variety of sources for such enzymes usable in the production of the saccharides. Thus, an optimum enzyme can be chosen from various types of enzymes depending on the optimum conditions of another enzymes usable in combination with the above enzymes to produce the desired saccharides, as well as on installations and final uses of the saccharides produced, resulting in an efficient production of the saccharides. Conventionally known non-reducing saccharide-forming enzymes can be grouped into those having optimum temperatures of relatively-lower temperatures of about 40° C. or lower, and those having optimum temperatures of relatively-higher temperatures of about 60° C. or higher. While conventionally known trehalose-releasing enzymes can be grouped into those having optimum temperatures in a relatively-lower temperature range, about 45° C. or lower, and those having optimum temperatures in a relatively-higher temperature range, about 60° C. or higher. However, any non-reducing saccharide-forming enzyme and a trehalose-releasing enzyme having an optimum temperature in a medium temperature range, about 50° C., have never yet been opened.

Among saccharide-related enzymes used in the production of saccharides from starch materials, enzymes as a major group have an optimum temperature in a medium temperature range. Such enzymes may be required in the process for producing the aforesaid trehalose and non-reducing saccharides; No non-reducing saccharide-forming enzyme and no trehalose-releasing enzyme, which have an optimum temperature in a medium temperature range, have not yet been established so that there has not yet been realized a process for producing saccharides in a sufficient yield using either or both of these enzymes together with the above saccharide-related enzymes. Depending on installations for producing saccharides and final uses of them, there have been required enzymes having an optimum temperature in a medium temperature range in their enzymatic reactions. It is far from saying that it has established a process for producing saccharides in a satisfactorily-high yield using a non-reducing saccharide-forming enzyme and a trehalose-releasing enzyme. As described above the establishment of a non-reducing saccharide-forming enzyme and a trehalose-releasing enzyme having an optimum temperature in a medium temperature range, and a process for producing saccharides comprising non-reducing saccharides are in great demand.

SUMMARY OF THE INVENTION

In view of this, the first object of the present invention is to provide a non-reducing saccharide-forming enzyme having an optimum temperature in a medium temperature range.

The second object of the present invention is to provide a DNA encoding the non-reducing saccharide-forming enzyme.

The third object of the present invention is to provide a process for producing the non-reducing saccharide-forming enzyme.

The fourth object of the present invention is to provide a trehalose-releasing enzyme having an optimum temperature in a medium temperature range.

The fifth object of the present invention is to provide a DNA encoding the trehalose-releasing enzyme.

The sixth object of the present invention is to provide a process for producing the trehalose-releasing enzyme.

The seventh object of the present invention is to provide a microorganism capable of producing the non-reducing saccharide-forming enzyme and/or the trehalose-releasing enzyme.

The eighth object of the present invention is to provide a process for producing saccharides comprising non-reducing saccharides, which uses the non-reducing saccharide-forming enzyme and/or the trehalose-releasing enzyme.

In order to attain the above objects, the present inventors extensively screened microorganisms, that can overcome the objects, in soils. As a result, they found that a microorganism newly isolated from a soil in Ako-shi, Hyogo, Japan, produced enzymes that can solve the above objects. The present inventors isolated separately the desired non-reducing saccharide-forming enzyme and trehalose-releasing enzyme from the microorganism, and then identified their properties, revealing that the enzymes both had an optimum temperature in a medium temperature range. The identification of the microorganism confirmed that it was a novel microorganism of the genus *Arthrobacter*, and named *Arthrobacter* sp. S34. The microorganism was deposited on Aug. 6, 1998, in the National Institute of Bioscience and Human-Technology Agency of Industrial Science and Technology, Higashi 1-1-3, Tsukuba-shi, Ibaraki, Japan, and accepted and has been maintained by the institute under the accession number of FERM BP-6450.

The present inventors continued studying, isolated DNAs encoding the above-identified enzymes from the microorganism, *Arthrobacter* sp. S34, FERM BP-6450, decoded the nucleotide sequences, and determined the amino acid sequences of the enzymes. The inventors confirmed that *Arthrobacter* sp. S34, FERM BP-6450, and transformants, into which the DNAs obtained in the above had been introduced in a usual manner, produced desired amounts of enzymes. It was also confirmed that the enzymes thus obtained can be advantageously used in producing saccharides which comprise trehalose and non-reducing saccharides having a trehalose structure in a medium temperature range. The present invention was made based on these findings.

The first object of the present invention is solved by a novel non-reducing saccharide-forming enzyme that forms a non-reducing saccharide having a trehalose structure as an end unit from reducing partial starch hydrolysates, and has an optimum temperature in a medium temperature range.

The second object of the present invention is solved by a DNA encoding the non-reducing saccharide-forming enzyme.

The third object of the present invention is solved by a process for producing the non-reducing saccharide-forming enzyme, characterized in that it comprises the steps of culturing a microorganism capable of producing the enzyme, and collecting the produced enzyme from the culture.

The fourth object of the present invention is solved by a novel trehalose-releasing enzyme which specifically hydrolyses a non-reducing saccharide having a trehalose structure as an end unit and a glucose polymerization degree of at least 3 to release trehalose from the rest of the non-reducing saccharide, and which has an optimum temperature in a medium temperature range.

The fifth object of the present invention is solved by a DNA encoding the trehalose-releasing enzyme.

The sixth object of the present invention is solved by a process for producing the trehalose-releasing enzyme, characterized in that it comprises the steps of culturing a microorganism capable of producing the enzyme, and collecting the produced enzyme from the culture.

The seventh object of the present invention is solved by a microorganism selected from *Arthrobacter* sp. S34, FERM BP-6450, and mutants thereof.

The eighth object of the present invention is solved by a process for producing saccharides, comprising the steps of allowing the either or both of the above enzymes to act on reducing partial starch hydrolysates to produce non-reducing saccharides, and collecting the non-reducing saccharides or saccharide compositions having a relatively-low reducibility and containing the non-reducing saccharides.

BRIEF DESCRIPTION OF THE ACCOMPANYING DRAWINGS

Figure 5:
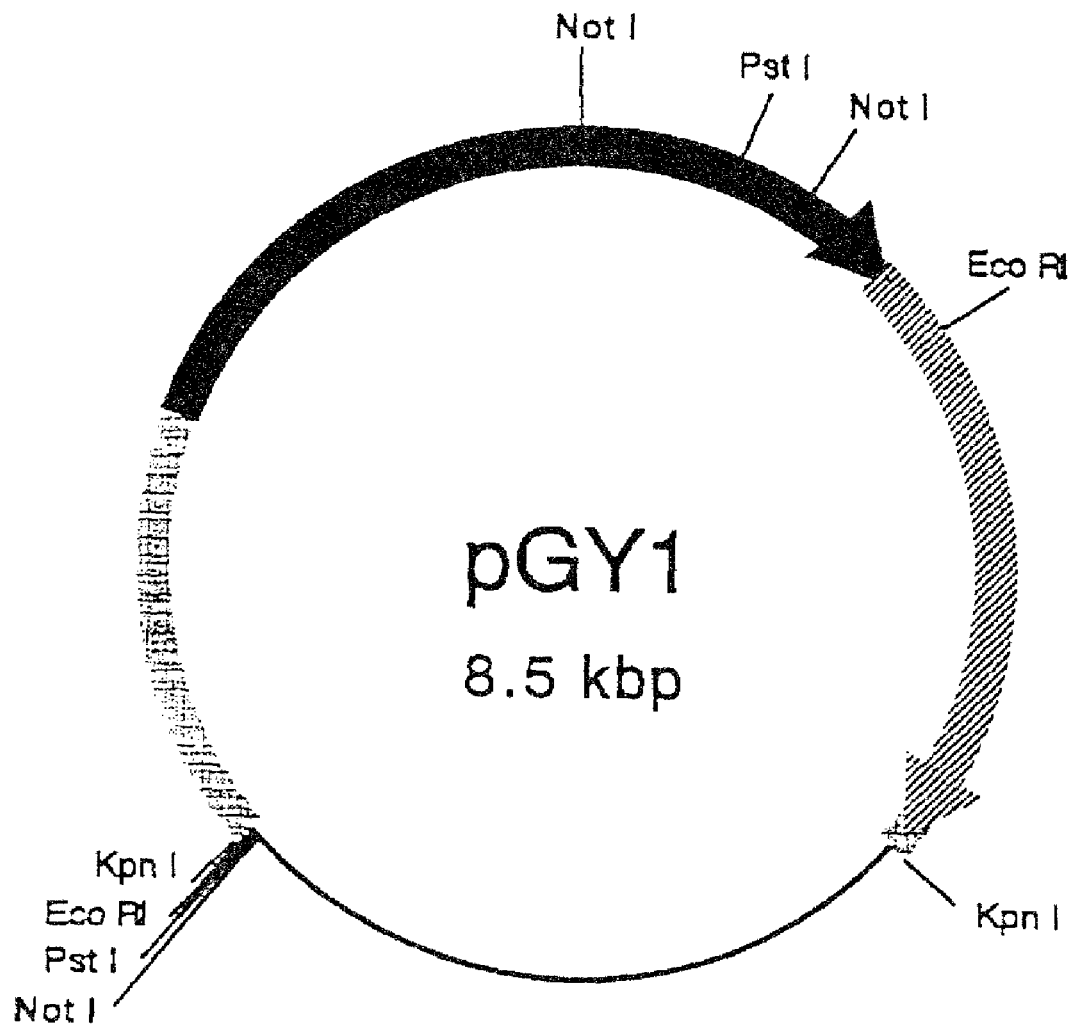

FIG. 5 is a restriction map of the recombinant DNA pGY1 according to the present invention. The bold line shows the nucleotide sequence from *Arthrobacter* sp. S34, FERM BP-6450. The black arrow within the bold line shows a nucleotide sequence encoding the present non-reducing saccharide-forming enzyme, while the oblique arrow shows a nucleotide sequence encoding the present trehalose-releasing enzyme.

Figure 6:
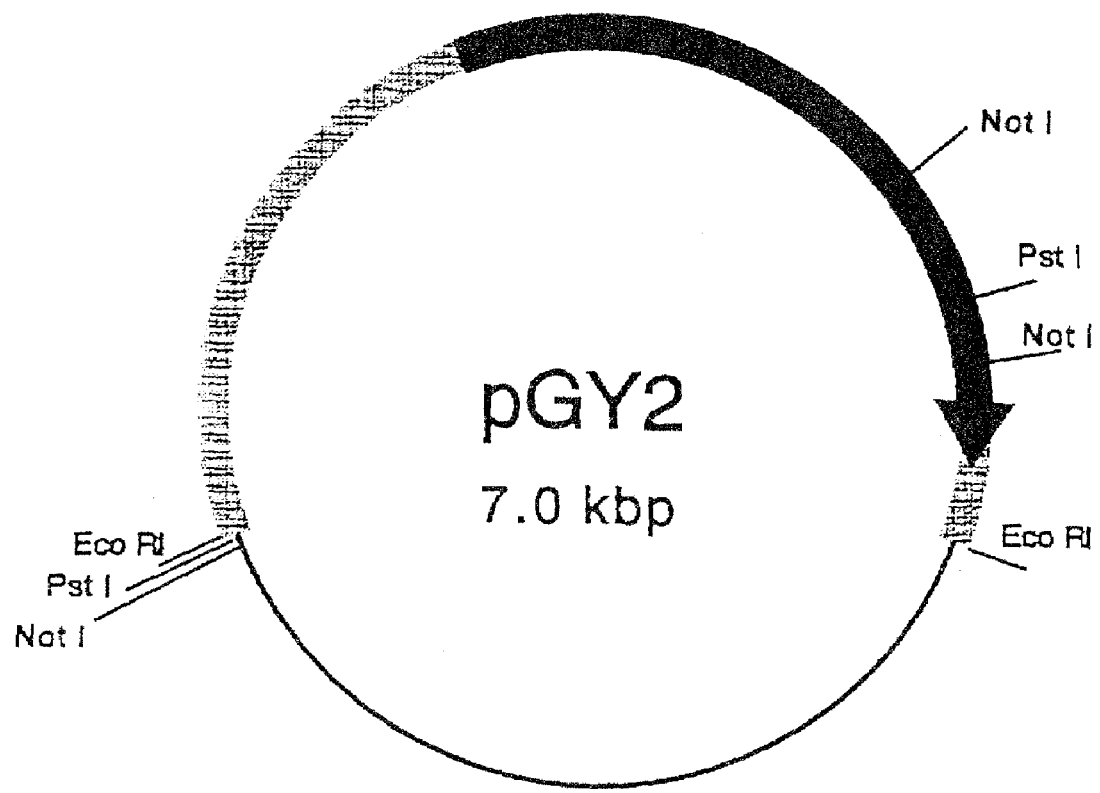

FIG. 6 is a restriction map of the recombinant DNA pGY2 according to the present invention. The bold line shows the nucleotide sequence from *Arthrobacter* sp. S34, FERM BP-6450. The black arrow within the bold line shows a nucleotide sequence encoding the present non-reducing saccharide-forming enzyme.

Figure 7:
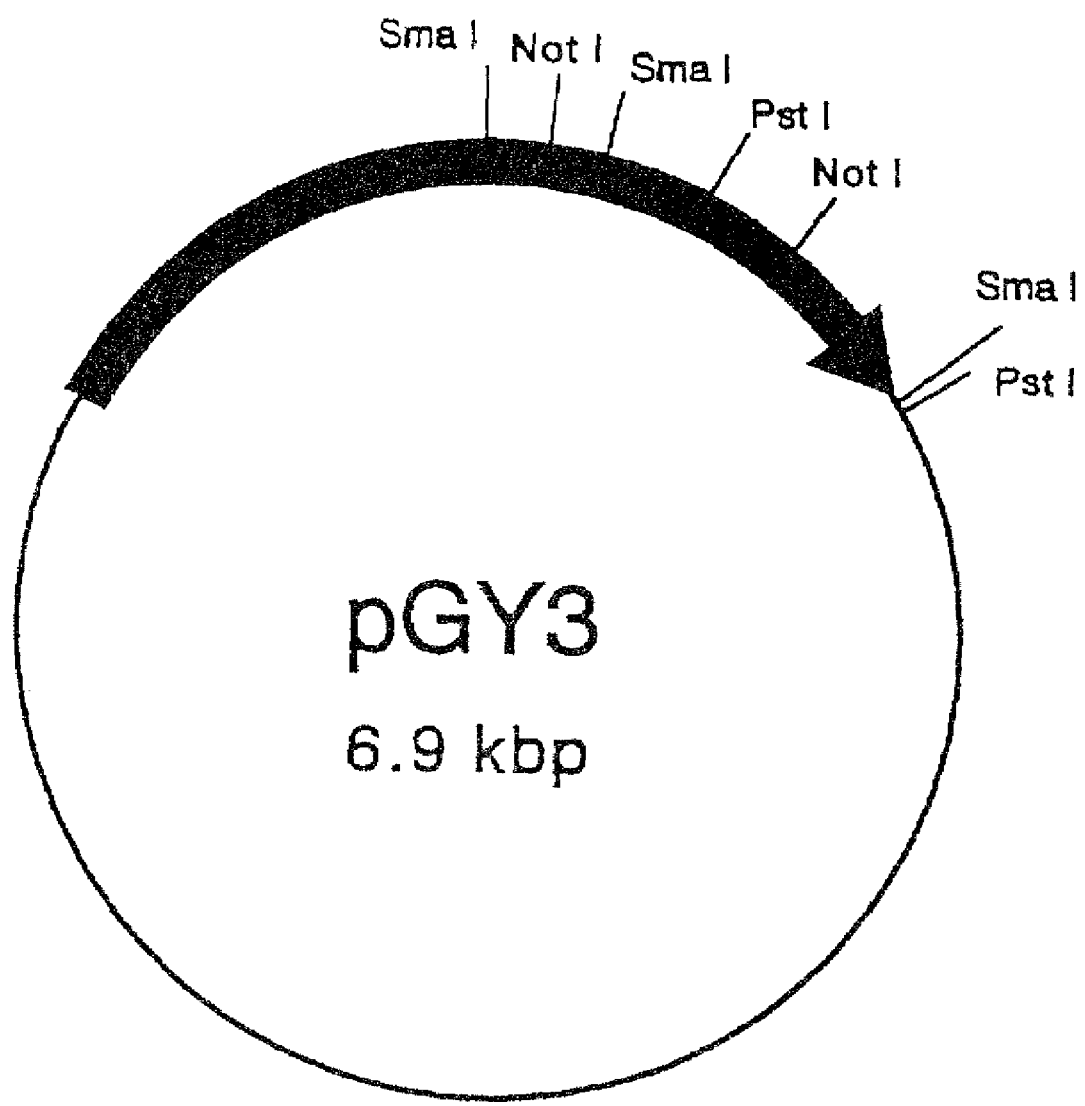

FIG. 7 is a restriction map of the recombinant DNA pGY3 according to the present invention. The black arrow shows the nucleotide sequence, encoding the present non-reducing saccharide-forming enzyme, from *Arthrobacter* sp. S34, FERM BP-6450.

Figure 8:
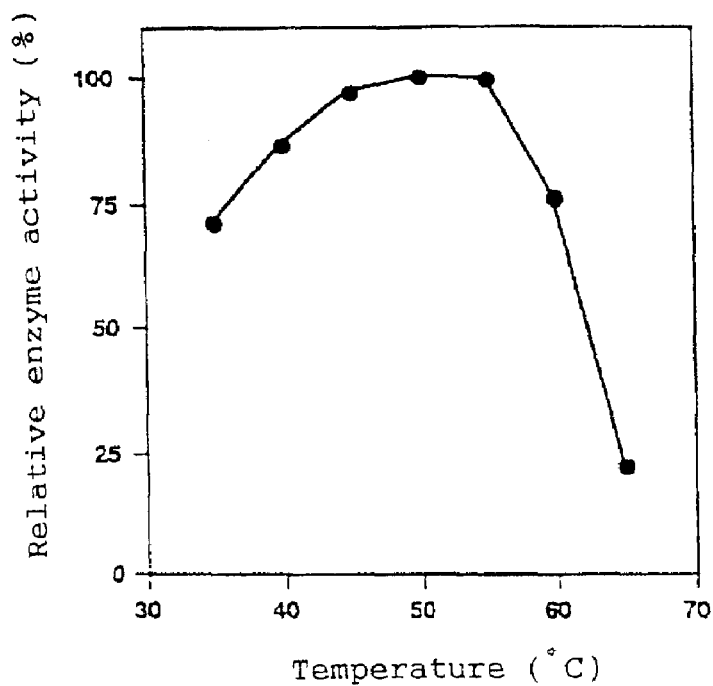

FIG. 8 is a figure that shows the influence of temperature on the activity of a trehalose-releasing enzyme from *Arthrobacter* sp. S34, FERM BP-6450, according to the present invention.

Figure 9:
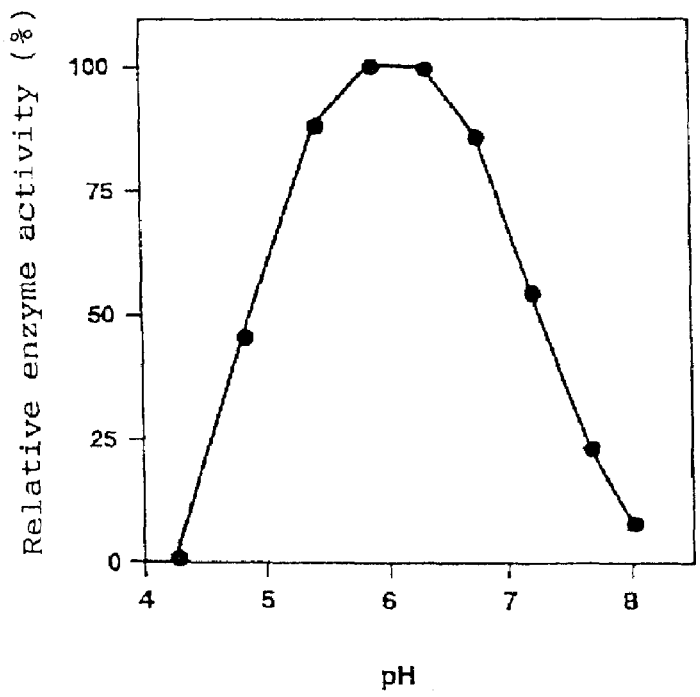

FIG. 9 is a figure that shows the influence of pH on the activity of a trehalose-releasing enzyme from *Arthrobacter* sp. S34, FERM BP-6450, according to the present invention.

Figure 10:
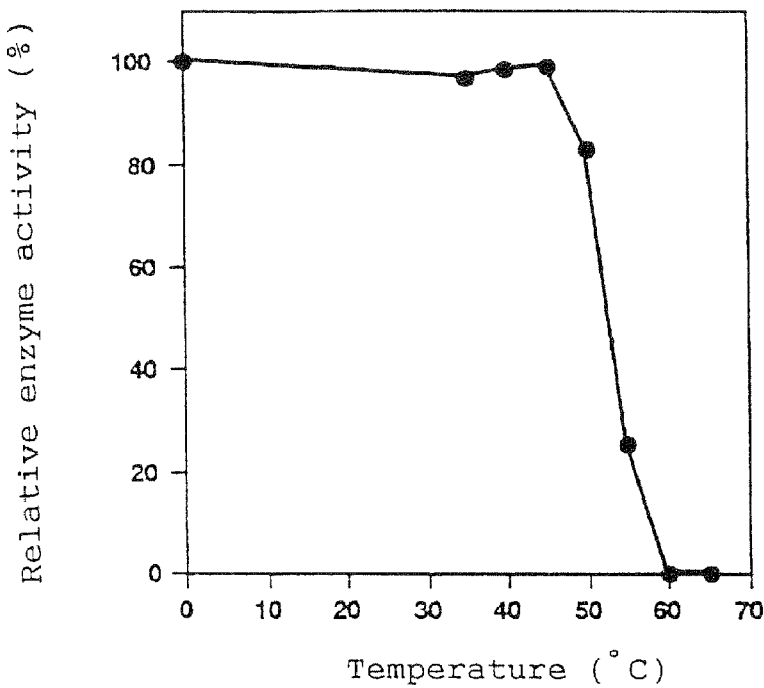

FIG. 10 is a figure that -shows the influence of temperature on the stability of a trehalose-releasing enzyme from *Arthrobacter* sp. S34, FERM BP-6450, according to the present invention.

Figure 11:
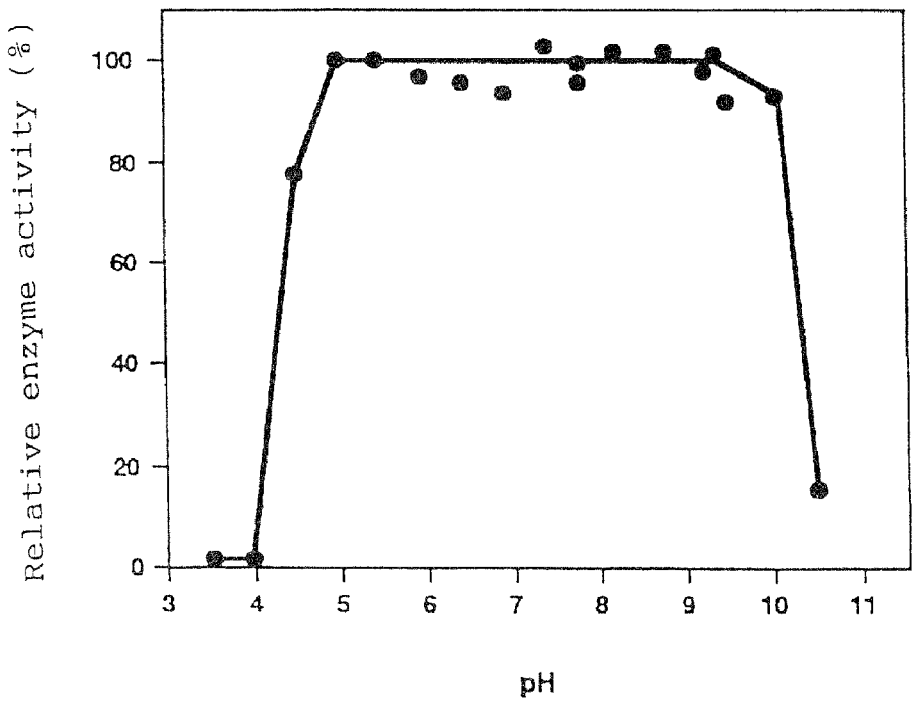

FIG. 11 is a figure that shows the influence of pH on the stability of a trehalose-releasing enzyme from *Arthrobacter* sp. S34, FERM BP-6450, according to the present invention.

Figure 12:
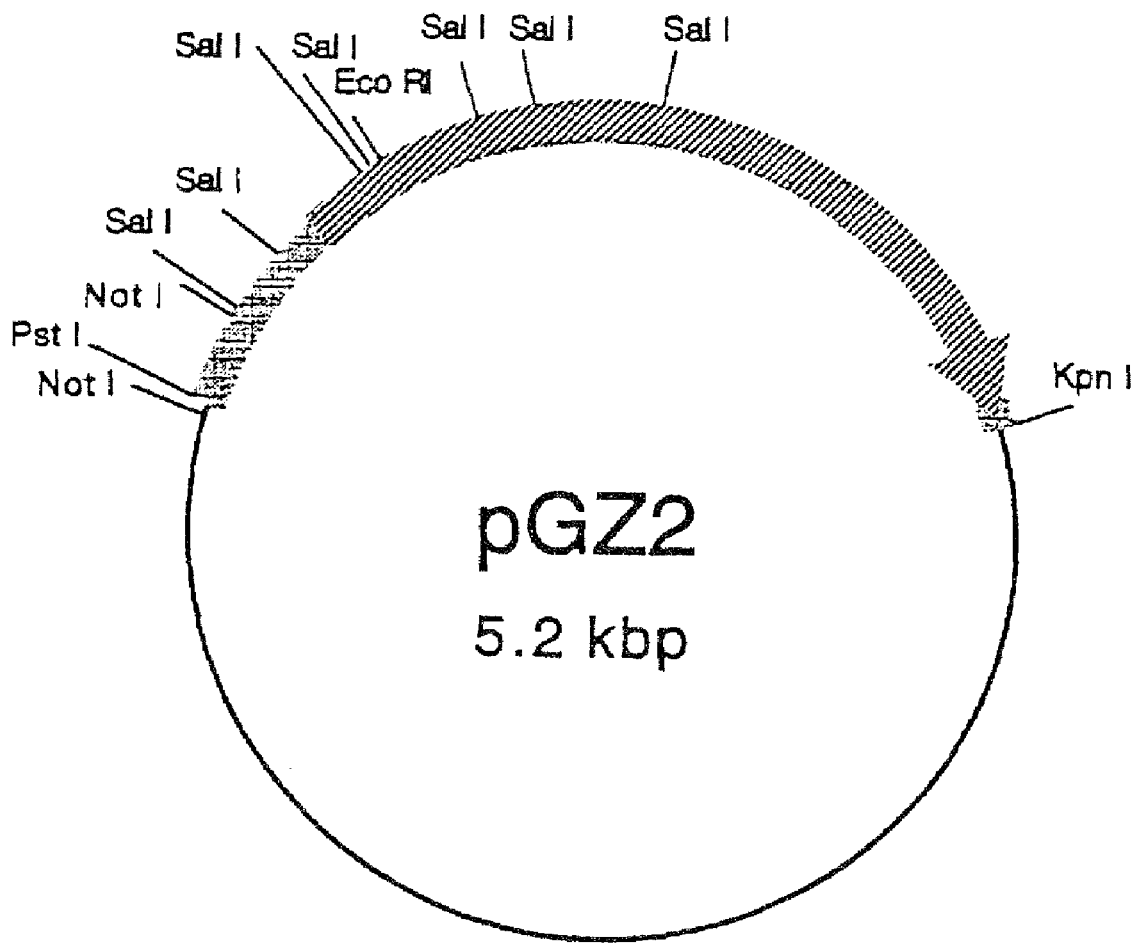

FIG. 12 is a restriction map of the recombinant DNA pGZ2 according to the present invention. The bold line shows the nucleotide sequence from *Arthrobacter* sp. S34, FERM BP-6450. The oblique arrow within the bold line shows a nucleotide sequence encoding the present trehalose-releasing enzyme.

Figure 13:
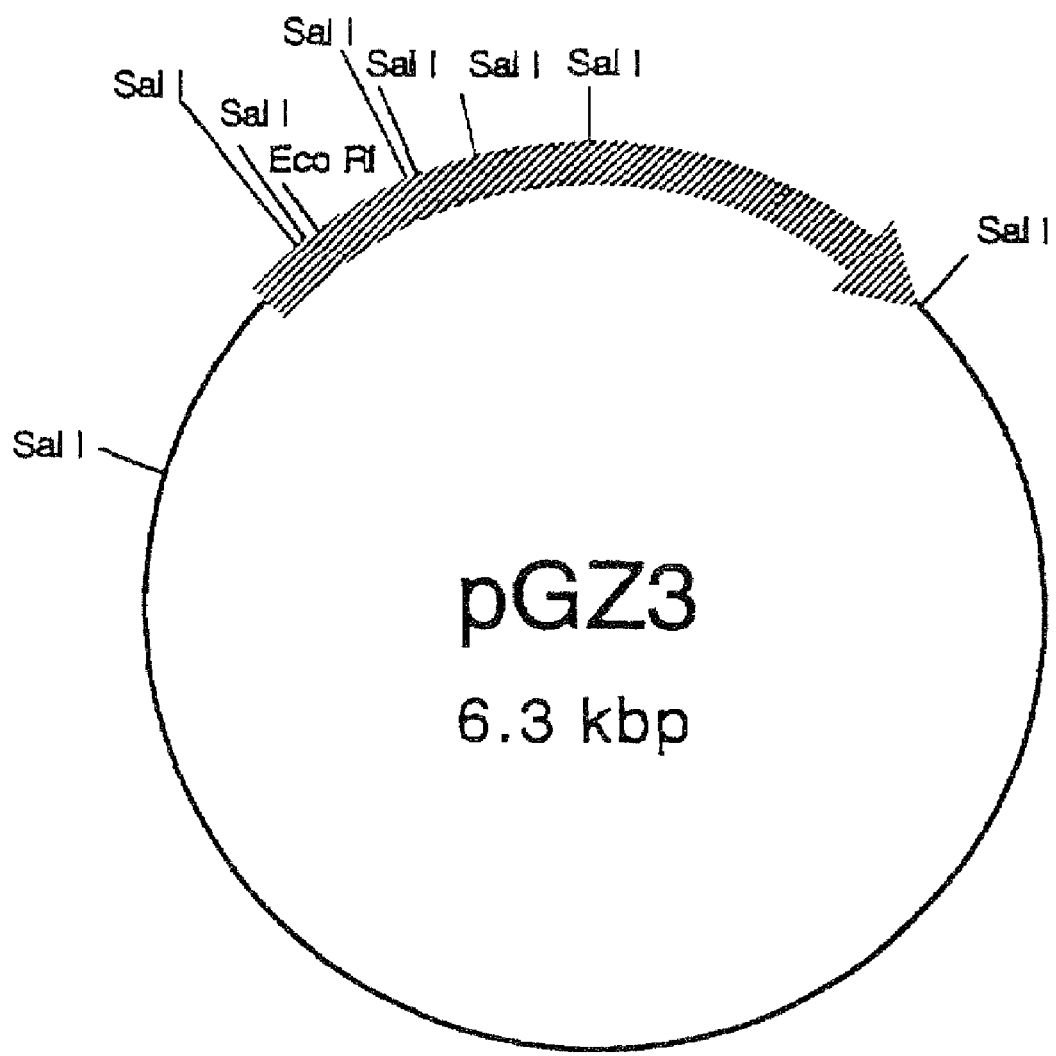

FIG. 13 is a restriction map of the recombinant DNA pGZ3 according to the present invention. The oblique arrow shows the nucleotide sequence from *Arthrobacter* sp. S34, FERM BP-6450.

DETAILED DESCRIPTION OF THE INVENTION

The present invention relates to a non-reducing saccharide-forming enzyme and a trehalose-releasing enzyme, and a process for producing a saccharide using either or both of the enzymes. The wording "non-reducing saccharide-forming enzyme" as referred to in the present invention represents an enzyme which has an action of forming a non-reducing saccharide having a trehalose structure as an end unit from reducing partial starch hydrolysates. The wording "trehalose-releasing enzyme" as referred to in the present invention represents an enzyme which specifically hydrolyses a non-reducing saccharide having a trehalose structure as an end unit and a glucose polymerization degree of at least 3 to release trehalose from the rest of the non-reducing saccharide. The wording "a medium temperature range" as referred to in the present invention represents a middle temperature range in reaction temperatures which are conventionally used in producing saccharides from starch materials by an enzymatic reaction. In most cases of such processes, different reaction temperatures of about 10° C. to about 100° C. and around the temperatures are used. The nonreducing saccharide-forming enzyme according to the present invention has an action as such an enzyme and has an optimum temperature in a medium temperature range, preferably a temperature range over 40° C. but less than 60° C., and more preferably it has an optimum pH in an acid pH range in addition to the optimum temperature. The trehalose-releasing enzyme according to the present invention has an action as such an enzyme and has an optimum temperature in a medium temperature range, preferably a temperature range over 45° C. but below 60° C., and more preferably it has an optimum pH in an acid pH range in addition to the optimum temperature. These present enzymes should not be restricted to their origins and sources.

The activity of the present non-reducing saccharide-forming enzyme is assayed as follows: One ml of an enzyme solution is added to four ml of 1.25 w/v % maltopentaose as a substrate in 20 mM phosphate buffer (pH 6.0), and the mixture solution is incubated at 50° C. for 60 min. The reaction mixture is heated at 100° C. for 10 min to suspend the enzymatic reaction, and the reaction mixture is precisely diluted by 10 times with deionized water, followed by determining the reducing power of the diluted solution on the Somogyi-Nelson's method. As a control, an enzyme solution, which had been heated at 100° C. for 10 min to inactivate the enzyme, is treated similarly as above. One unit activity of the present enzyme is defined as the amount of enzyme which eliminates the reducing power of that of one μmole of maltopentaose per minute when determined with the above-mentioned assay. The optimum temperature of the enzyme as referred to in the present invention is determined in accordance with the assay; It is assayed by adjusting the enzymatic reaction temperature at different temperatures including 50° C., allowing a prescribed amount of the enzyme to act on the substrate at the different temperatures according to the assay, and determining the reduction level of reducing power at the temperatures in accordance with the assay, followed by comparing the determined reduction levels one another and determining the optimum temperature of the present enzyme that showed a maximum temperature.

The activity of the present trehalose-releasing enzyme is assayed as follows: One ml of an enzyme solution is added to four ml of 1.25 w/v % maltotriosyltrehalose, i.e., α-maltotetraosyl-α-D-glucoside, as a substrate, in 20 mM phosphate buffer (pH 6.0), and the mixture solution is incubated at 50° C. for 30 min, followed by suspending the enzymatic reaction by the addition of the Somogyi copper solution and assaying the reducing power by the Somogyi-Nelson's method. As a control, it is similarly assayed using an enzyme solution which has been inactivated by heating at 100° C. for 10 min. One unit activity of the present enzyme is defined as the amount of enzyme which increases the reducing power of one μ mole of glucose per minute when determined with the above-mentioned assay. The optimum temperature of the enzyme as referred to in the present invention is determined in accordance with the assay; It is assayed by adjusting the enzymatic reaction temperature at the different temperatures including 50° C., allowing a prescribed amount of the enzyme to act on the substrate at the temperatures according to the assay, and determining the increased level of reducing power at the different temperatures in accordance with the assay, followed by comparing the determined increased levels one another and determining the optimum temperature of the present enzyme that showed a maximum temperature.

Explaining the present non-reducing saccharide-forming enzyme based on the amino acid sequence, the enzyme has the amino acid sequence of SEQ ID NO:1 as a whole, and has the amino acid sequences of SEQ ID NOs:2 to 6 as partial amino acid sequences in some cases. In addition to these enzymes having the whole of the above-identified amino acid sequences, the present invention includes another types of enzymes which comprise a part of any one of the amino acid sequences selected therefrom or which have both the action as the present non-reducing saccharide-forming enzyme and the above-identified optimum temperature. Examples of the amino acid sequences of such enzymes are those which contain, within the amino acid sequences, a partial amino acid sequence or an amino acid residue that are related to the expression of the properties of the present non-reducing saccharide-forming enzyme, and which one or more amino acids are replaced with different amino acids, added thereunto and/or deleted therefrom other than the above partial amino acid sequence or the amino acid residue. Examples of the amino acid sequences replaced with different amino acids as referred to in the present invention include those which less than 30% and preferably less than 20% of the amino acid sequences composing the amino acid sequence of SEQ ID NO:1 are replaced with another amino acids which have similar properties and structures to respective ones to be replaced. Examples of groups of such amino acids are a group of aspartic acid and glutamic acid as acid amino acids, one of lysine, arginine, and histidine as basic amino acids, one of asparagine and glutamine as amid-type amino acids, one of serine and threonine as hydroxyamino acids, and one of valine, leucine and isoleucine as branched-chain amino acids. Examples of another amino acid sequences of the present enzyme containing a part of any one of the amino acid sequences selected from SEQ ID NOs:1 to 6 are those which might have a substantially similar stereo-structure to the one of the amino acid sequence of SEQ ID NO:1, i.e., replacement, deletion and/or addition of amino acid(s) are introduced into the amino acid sequence of SEQ ID NO:1. The stereo-structure of proteins is estimable by screening commercially available databases for stereo-structures of proteins which have amino acid sequences related to the aiming ones and have revealed stereo-structures, referencing the screened stereo-structures, and using commercially available soft wares for visualizing stereo-structures. The above-identified amino acid sequence of the present non-reducing saccharide-forming enzyme has a homology of at least 57%, preferably at least 70%, and more preferably at least 80% to SEQ ID NO:1.

As described above, the non-reducing saccharide-forming enzyme should not be restricted to a specific origin/source. Examples of such are those derived from microorganisms, i.e., those of the genus *Arthrobacter, Arthrobacter* sp. S34, FERM BP-6450, and its mutants. The mutants can be obtained by treating in a usual manner *Arthrobacter* sp. S34, FERM BP-6450, with known mutagens such as N-methyl-N'-nitro-N-nitrosoguanidine, ethyl methanesulfonate, ultraviolet, and transposon; screening the desired mutants capable of producing a non-reducing saccharide-forming enzyme and having an optimum temperature at temperatures in a medium temperature range, and usually at temperatures in the range of over 40° C. but below 60° C. The enzyme from *Arthrobacter* sp. S34, FERM BP-6450, usually has the amino acid sequences of SEQ ID NOs:1 to 6. Another non-reducing saccharide-forming enzymes from microorganisms of mutants *Arthrobacter* sp. S34, FERM BP-6450, and another microorganisms comprise the whole or a part of any one of the amino acid sequences of SEQ ID NOs:1 to 6. Concrete examples of another enzymes include recombinant enzymes which act as the present non-reducing saccharide-forming enzyme and have an optimum temperature at temperatures in a medium temperature range, and usually at temperatures of over 40° C. but below 60° C. The recombinant enzymes can be obtainable by applying the recombinant DNA technology for the DNA encoding the present non-reducing saccharide-forming enzyme, and have the whole or a part of any one of the amino acid sequences of SEQ ID NOs:1 to 6.

Most of the non-reducing saccharide-forming enzyme according to the present invention has the following physico-chemical properties:

(1) Action
  Forming a non-reducing saccharide having a trehalose structure as an end unit from a reducing partial starch hydrolysates having a degree of glucose polymerization of 3 or higher;

(2) Molecular Weight
  About 75,000±10,000 daltons on sodium dodecyl sulfate-polyacrylamide gel electrophoresis (SDS-PAGE);
(3) Isoelectric Point (pI)
  About 4.5±0.5 on isoelectrophoresis using ampholyte;
(4) Optimum Temperature
  About 50° C. when incubated at pH 6.0 for 60 min;
(5) Optimum pH
  About 6.0 when incubated at 50° C. for 60 min;
(6) Thermal Stability
  Stable up to a temperature of about 55° C. when incubated at pH 7.0 for 60 min; and
(7) pH Stability
  Stable at pHs of about 5.0 to about 10.0 when incubated at 4° C. for 24 hours.

The present non-reducing saccharide-forming enzyme can be obtained in a prescribed amount by the later described present process for producing the same.

The present invention provides a DNA encoding the present non-reducing saccharide-forming enzyme. Such a DNA is quite useful in producing the enzyme in the form of a recombinant protein. In general, the DNA includes those which encode the enzyme independently of its origin/source. Examples of such a DNA are those which contain the whole or a part of the nucleotide sequence of SEQ ID NO:7 or complementary ones thereunto. The DNA comprising the whole of the nucleotide sequence of SEQ ID NO:7 encodes the amino acid sequence of SEQ ID NO:1. The DNAs, which contain the whole or a part of the nucleotide sequence of SEQ ID NO:7, include those which have an amino acid sequence relating to the expression of the properties of the present non-reducing saccharide-forming enzyme, and have a nucleotide sequence corresponding to the amino acid sequence, and the nucleotide sequence of SEQ ID NO:7 introduced with a replacement, deletion and/or addition of one or more bases while retaining the nucleotide sequence relating to the expression of the properties of the present non-reducing saccharide-forming enzyme. The DNAs according to the present invention should include those which one or more bases are replaced with different ones based on the degeneracy of genetic code. Also the DNAs according to the present invention include those which comprise the nucleotide sequences that encode the present non-reducing saccharide-forming enzyme and further comprise additional one or more another nucleotide sequences selected from the group consisting of ribosome-binding sequences such as an initiation codon, termination codon, and Shine-Dalgarno sequence; nucleotide sequences encoding signal peptides, recognition sequences for appropriate restriction enzymes; nucleotide sequences to regulate the expression of genes for promotor and enhancers; and terminators, all of which are generally used in recombinant DNA technology for producing recombinant proteins. For example, since a part of and the whole of the nucleotide sequence of SEQ ID NO:8 function as ribosome-binding sequences, DNAs to which the part of and the whole of the nucleotide sequence of SEQ ID NO:8 are ligated upstream of the nucleotide sequences encoding the present non-reducing saccharide-forming enzyme can be arbitrarily used in producing the enzyme as a recombinant protein.

As described above, the DNAs encoding the present non-reducing saccharide-forming enzyme should not be restricted to their origins/sources, and they are preparable by screening DNAs from different sources based on hybridization with a DNA comprising a nucleotide sequence which encodes at least a part of the amino acid sequence of the enzyme, eg., the amino acid sequence of SEQ ID NO:1. Actual examples of these sources are microorganisms of the genus *Arthrobacter*, and preferably, *Arthrobacter* sp. S34, FERM BP-6450, and its mutants, all of which produce the non-reducing saccharide-forming enzyme. To screen the microorganisms, conventional methods used in this field for screening or cloning DNAs such as screening methods of recombinant libraries, PCR method, and their modified methods. As a result of screening, the desired DNAs can be obtained by collecting in a usual manner DNAs confirmed with the expected hybridization. Generally, the DNAs thus obtained comprise a part of or the whole of the nucleotide sequence of SEQ ID NO:7. For example, a DNA which comprises the whole of the nucleotide sequence of SEQ ID NO:7 is generally obtained from *Arthrobacter* sp. S34, FERM BP-6450. DNAs comprising a part of the nucleotide sequence of SEQ ID NO:7 can be obtained by similarly screening DNAs from microorganisms as sources other than the above strain, capable of producing the present non-reducing saccharide-forming enzyme. Such DNAs can be prepared by selecting DNAs, which encode the enzymes having the properties of the present enzyme, from DNAs into which have been introduced a replacement, addition and/or deletion of one or more bases of the above-mentioned DNAs by using one or more conventional mutation-introducing methods. The DNAs can be also obtained by applying conventional chemical syntheses based on the nucleotide sequence encoding the present non-reducing saccharide-forming enzyme, e.g., one of SEQ ID NO:7. Once in hand, the DNAs according to the present invention can be easily amplified to the desired level by applying or using PCR method and autonomously-replicable vectors.

The present DNA encoding the non-reducing saccharide-forming enzyme include those in the form of recombinant DNAs which the DNAs have been introduced into appropriate vectors. The recombinant DNAs can be relatively-easily preparable by recombinant DNA technology in general if only the DNAs are available. Any types of vectors can be used in the present invention as long as they autonomously replicable in appropriate hosts. Examples of such vectors are pUC18, pBluescript II SK(+), pKK223-3, λgt·λC, etc., which use *Escherichia coli* as a host; pUB110, pTZ4, pC194, ρ11, φ1, φ105, etc., which use microorganisms of the genus *Bacillus*; and pHY300PLK, pHV14, TRp7, YEp7, pBS7, etc., which use two or more microorganisms as hosts. The methods to insert the present DNA into such vectors in the present invention may be conventional ones generally used in this field. A gene containing the present DNA and an autonomously-replicable vector are first digested with a restriction enzyme and/or ultrasonic disintegrator, then the resultant DNA fragments and vector fragments are ligated. The ligation is facilitated by the use of restriction enzymes which specifically act on the cleavage of the DNA, especially, KpnI, AccI, BamHI, BstXI, EcoRI, HindIII, NotI, PstI, SacI, SalI, SmaI, SpeI, XbaI, XhoI, etc. To ligate DNA fragments and vectors, firstly they may be annealed if necessary, then subjected to the action of a DNA ligase in vivo or in vitro. The recombinant DNA thus obtained can be replicable without substantial limitation in an appropriate host.

The present DNA encoding the non-reducing saccharide-forming enzyme further includes transformants which the DNA has been introduced into appropriate vectors. The transformants can be easily preparable by introducing the DNA or recombinant DNA obtained in the above into appropriate hosts to transform them. As the hosts, microorganisms and cells from plants and animals, which are used conventionally in this field and chosen depending on the vectors in the recombinant DNA, can be used. The microorganisms as hosts include those of the genera *Escherichia*, *Bacillus*, and *Arthrobacter*, and another actinomycetes, yeasts, fungi, etc. To introduce the present DNA into these host microorganisms, conventional competent cell method and protoplast method can be used. The present DNA, which encodes the non-reducing saccharide-forming enzyme introduced into the transformants in the present invention, may be present in a separatory form from chromosomes or in an incorporated form into chromosomes. The DNA incorporated into hosts' chromosomes has a character of being stably retained therein and may be advantageously used in producing the present recombinant protein.

The present non-reducing saccharide-forming enzyme can be obtained in a desired amount by a process for producing the enzyme characterized in that it comprises the steps of culturing microorganisms capable of producing the enzyme, and collecting the produced enzyme from the culture. The microorganisms used in the process can be used independently of the genus or the species as long as they produce the enzyme. Examples of such microorganisms are microorganisms of the genus *Arthrobacter*, *Arthrobacter* sp. S34, FERM BP-6450, and mutants thereof, as well as transformants obtainable by introducing the present DNA encoding the enzyme into appropriate hosts.

Any nutrient culture media used in culturing the process for producing the present non-reducing saccharide-forming enzyme can be used as long as the aforesaid microorganisms grow therein and produce the enzyme without restriction to a specific nutrient culture medium. Generally, the nutrient culture media contain carbon and nitrogen sources, and if necessary minerals may be added. Examples of the carbon sources are saccharides such as dextrins, starches, partial starch hydrolysates, glucose, etc., and are saccharide-containing substances such as molasses and yeast extracts, and organic acids such as glucuronic acid and succinic acid. The concentration of the carbon sources is chosen depending on the types used, usually 30 w/v %, and preferably 15 w/w % or lower. Examples of the nitrogen sources appropriately used in the present invention are inorganic-nitrogen-containing substances such as ammonium salts, nitrate, etc.; organic-nitrogen-containing substances such as urea, corn steep liquor, casein, peptone, yeast extract, beef extract, etc. Depending on use, it is selectively used among inorganic ingredients such as salts of calcium, magnesium, potassium, sodium, phosphoric acid, manganese, zinc, iron, copper, molybdenum, cobalt, etc.

The culture conditions used for producing the present enzyme can be used selectively from appropriate conditions suitable for growing respective microorganisms used. For example, in the case of using microorganisms of the genus *Arthrobacter* including *Arthrobacter* sp. S34, FERM BP-6450, the cultivation temperature is usually in the range of 20-50° C., and preferably 25-37° C.; the cultivation pH is usually in the range of pH 4-10, and preferably pH 5-9; and the cultivation time is in the range of 10-150 hours. With these conditions, the microorganisms are cultured under aerobic conditions. When used transformants prepared by introducing into appropriate hosts the present DNA encoding the present non-reducing saccharide-forming enzyme, the transformants are cultured under aerobic conditions at conditions selected from the culture conditions such as the culture temperatures of 20-65° C., the culture pH of 2-9, and the culture time of 1-6 days, although they vary depending on the genus, species, strains or types of microorganisms and vectors. The cultures thus obtained generally contain the present enzyme in cell fractions. In the case of culturing transformants obtained by using as hosts the microorganisms of the genus *Bacillus*, the resulting cultures may contain the present enzyme in supernatant fractions depending on vectors used to transform the hosts. The content of the present enzyme in the cultures thus obtained is usually 0.01-1,000 units per ml of the culture, though it varies depending on the genus, species or strains of the microorganisms and culture conditions used.

The present non-reducing saccharide-forming enzyme is collected from the resulting cultures. The collection method is not restricted; The present enzyme can be obtained by separating and collecting any one of fractions of cells and culture supernatants found with a major activity of the enzyme, and if necessary subjecting the collected fraction to an appropriate purification method to collect a purified fraction containing the enzyme. To separate the fractions of cells and culture supernatants of the cultures, conventional solid-liquid separation methods such as centrifugation and filtration using precoat filters and plain- and hollow fiber-membranes can be arbitrarily used. The desired fractions are collected from the separated fractions of cells and culture supernatant. For the fraction of cells, the cells are disrupted into a cell disruptant which is then separated into a cell extract and an insoluble cell fraction, followed by collecting either of the desired fractions. The insoluble cell fraction can be solubilized by conventional methods, if necessary. As a method to disrupt cells, any one of techniques of ultrasonication, treatment with cell-wall-lysing enzymes such as lysozyme and glucanase, and load of mechanical press can be arbitrarily used. To disrupt cells the cultures can be directly treated with any one of the above techniques, and then resulting mixtures are treated with any one of the above solid-liquid separation methods to collect a liquid fraction. Thus a cell extract can be arbitrarily obtained.

The methods used for more purifying the present non-reducing saccharide-forming enzyme include conventional ones to purify saccharide-related enzymes in general such as salting out, dialysis, filtration, concentration, gel filtration chromatography, ion-exchange chromatography, hydrophobic chromatography, reverse-phase chromatography, affinity chromatography, gel electrophoresis and, isoelectric point electrophoresis. These methods can be used in combination depending on purposes. From the resulting fractions separated by these methods, fractions with a desired activity assayed by the method for non-reducing saccharide-forming enzyme are collected to obtain the present non-reducing saccharide-forming enzyme purified to a desired level. According to the methods in the later described Examples, the present enzyme can be purified up to an electrophoretically homogenous level. As described above, the present method provide the present non-reducing saccharide-forming enzyme in the form of a culture, cell fraction, fraction of culture supernatant, cell disruptant, cell extract, soluble and insoluble cell-fraction, partially purified enzyme fraction, and purified enzyme fraction. These fractions may contain another type of the present trehalose-releasing enzyme. The non-reducing saccharide-forming enzyme thus obtained can be immobilized in a usual manner before use. The methods for immobilization are, for example, binding method to ion exchangers, covalent bonding/adsorption to and on resins and membranes, and entrapping immobilization method using high molecular weight substances. The non-reducing saccharide-forming enzyme thus obtained can be arbitrarily used in processes for producing saccharides including the later described present process for producing saccharide. Particularly, since the present non-reducing saccharide-forming enzyme has an optimum temperature in a medium temperature range and preferably has an optimum pH in an acid pH range, it can be advantageously used to produce saccharides when used in combination with the later described present trehalose-releasing enzyme, starch-debranching enzyme having an optimum pH in an acid pH range, and cyclomaltodextrin glucanotransferase that effectively acts at medium temperature range.

Explaining the present trehalose-releasing enzyme based on the amino acid sequence, the enzyme has the amino acid sequence of SEQ ID NO:9 as a whole, and has the amino acid sequences of SEQ ID NOs:10 to 16 as partial amino acid sequences in some cases. In addition to these enzymes having the whole of the above-identified amino acid sequences, the present invention includes another types of enzymes which comprise a part of any one of the amino acid sequences selected therefrom or which have both the action as the present trehalose-releasing enzyme and the above-identified optimum temperature. Examples of the amino acid sequences of such enzymes are those which contain, within the amino acid sequences, a partial amino acid sequence or an amino acid residue which relate to the expression of the properties of the present non-reducing saccharide-forming enzyme, and which one or more amino acids are replaced with different amino acids, added thereunto and/or deleted therefrom other than the above partial amino acid sequence or the amino acid residue. Examples of amino acid sequences replaced with different amino acids as referred to in the present invention include those which less than 30% and preferably less than 20% of the amino acid sequences composing the amino acid sequence of SEQ ID NO:9 are replaced with another amino acids which have similar properties and structures to respective ones to be replaced. Examples of groups of such amino acids are a group of aspartic acid and glutamic acid as acid amino acids, one of lysine, arginine, and histidine as basic amino acids, one of asparagine and glutamine as amid-type amino acids, one of serine and threonine as hydroxyamino acids, and one of valine, leucine and isoleucine as branched-chain amino acids. Examples of another amino acid sequences of the enzyme containing a part of any one of the amino acid sequences selected from SEQ ID NOs:9 to 16 are those which might have a substantially similar stereo-structure to the one of the amino acid sequence of SEQ ID NO:9, i.e., replacement, deletion and/or addition of amino acid(s) are introduced into the amino acid sequence of SEQ ID NO:9. The stereo-structure of proteins is estimable by screening commercially available databases for stereo-structures of proteins which have amino acid sequences related to the aiming ones and have revealed stereo-structures, referencing the screened stereo-structures, and using commercially available soft wares for visualizing stereo-structures. The above-identified amino acid sequence of the present trehalose-releasing enzyme has a homology of at least 60%, preferably at least 70%, and more preferably at least 80% to SEQ ID NO:9.

As described above, the trehalose-releasing enzyme should not be restricted to a specific origin/source. Examples of such are those derived from microorganisms, i.e., those of the genus *Arthrobacter, Arthrobacter* sp. S34, FERM BP-6450, and mutants thereof. The mutants can be obtained by treating in a usual manner *Arthrobacter* sp. S34, FERM BP-6450, with known mutagens such as N-methyl-N'-nitro-N-nitrosoguanidine, ethyl methanesulfonate, ultraviolet, and transposon; screening the desired mutants capable of producing a non-reducing saccharide-forming enzyme and having an optimum temperature at temperatures in a medium temperature range, and usually at temperatures in the range of over 45° C. but below 60° C. The enzyme from *Arthrobacter* sp. S34, FERM BP-6450, usually has the amino acid sequences of SEQ ID NOs:9 to 16. Another non-reducing saccharide-forming enzymes from microorganisms of mutants *Arthrobacter* sp. S34, FERM BP-6450, and another microorganisms comprise the whole or a part of any one of the amino acid sequences of SEQ ID NOs:9 to 16. Concrete examples of another enzymes include recombinant enzymes which act as the present trehalose-releasing enzyme and have an optimum temperature at temperatures in a medium temperature range, and usually at temperatures of over 45° C. but below 60° C. The recombinant enzymes can be obtainable by applying the recombinant DNA technology for the DNA encoding the present trehalose-releasing enzyme, and have the whole or a part of any one of the amino acid sequences of SEQ ID NOs:9 to 16.

Most of the trehalose-releasing enzyme according to the present invention has the following physicochemical properties:
(1) Action
  Specifically hydrolyses a non-reducing saccharide having a trehalose structure as an end unit to release trehalose from the rest of the non-reducing saccharide;
(2) Molecular weight
  About 62,000±5,000 daltons on sodium dodecyl sulfate-polyacrylamide gel electrophoresis (SDSPAGE);
(3) Isoelectric point (PI)
  About 4.7±0.5 on isoelectrophoresis using ampholyte;
(4) Optimum temperature
  About 50° C. to about 55° C. when incubated at pH 6.0 for 30 min;
(5) Optimum pH
  About 6.0 when incubated at 50° C. for 30 min;
(6) Thermal stability
  Stable up to a temperature of about 50° C. when incubated at pH 7.0 for 60 min; and
(7) pH Stability
  Stable at pHs of about 4.5 to about 10.0 when incubated at 4° C. for 24 hours.

The present trehalose-releasing enzyme can be obtained in a prescribed amount by the later described present process for producing the same.

The present invention provides a DNA encoding the present trehalose-releasing enzyme. Such a DNA is quite useful in producing the enzyme in the form of a recombinant protein. In general, the DNA includes those which encode the enzyme independently of its origin/source. Examples of such a DNA are those which contain the whole or a part of the nucleotide sequence of SEQ ID NO:17 or complementary ones thereunto. The DNA comprising the whole of the nucleotide sequence of SEQ ID NO:17 encodes the amino acid sequence of SEQ ID NO:9. The DNAs, which contain the whole or a part of the nucleotide sequence of SEQ ID NO:17, include those which have a nucleotide sequence corresponding to an amino acid sequence relating to the expression of the properties of the present non-reducing saccharide-forming enzyme, and have the nucleotide sequence of SEQ ID NO:17 introduced with a replacement, deletion and/or addition of one or more bases while retaining the nucleotide sequence relating to the expression of the properties of the present trehalose-releasing enzyme. The DNAs according to the present invention should include those which one or more bases are replaced with different ones based on the degeneracy of genetic code. Also the DNAs according to the present invention include those which comprise the nucleotide sequences that encode the present trehalose-releasing enzyme and further comprise additional one or more another nucleotide sequences selected from the group consisting of ribosome-binding sequences such as an initiation codon, termination codon, and Shine-Dalgarno sequence; nucleotide sequences encoding signal peptides, recognition sequences for appropriate restriction enzymes; nucleotide sequences to regulate the expression of genes for promotor and enhancers; and terminators, all of which are generally used in recombinant DNA technology for producing recombinant proteins. For example, since a part of and the whole of the nucleotide sequence of SEQ ID NO:8 function as ribosome-binding sequences, DNAs to which the part of and the whole of the nucleotide sequence of SEQ ID NO:8 are ligated upstream of the nucleotide sequences encoding the present trehalose-releasing enzyme can be arbitrarily used in producing enzyme as a recombinant protein.

As described above, the DNAs encoding the present trehalose-releasing enzyme should not be restricted to their origins/sources, and they are preparable by screening DNAs from different sources based on hybridization with a DNA comprising a nucleotide sequence which encodes at least a part of the amino acid sequence of the enzyme, eg., the amino acid sequence of SEQ ID NO:9. Actual examples of these sources are microorganisms of the genus *Arthrobacter*, and preferably, *Arthrobacter* sp. S34, FERM BP-6450, and its mutants, all of which produce the non-reducing saccharide-forming enzyme. To screen the microorganisms, conventional methods used in this field for screening or cloning DNAs such as screening methods of recombinant libraries, PCR method, and their modified methods. As a result of screening, the desired DNAs can be obtained by collecting in a usual manner DNAs confirmed with the expected hybridization. Generally, the DNAs thus obtained comprise a part of or the whole of the nucleotide sequence of SEQ ID NO:17. For example, a DNA which comprises the whole of the nucleotide sequence of SEQ ID NO:17 is generally obtained from *Arthrobacter* sp. S34, FERM BP-6450. DNAs comprising a part of the nucleotide sequence of SEQ ID NO:17 can be obtained by similarly screening DNAs from microorganisms as sources other than the above strain, capable of producing the trehalose-releasing enzyme. Such DNAs can be prepared by selecting DNAs, which encode the enzymes having the properties of the enzyme, from DNAs into which have been introduced a replacement, addition and/or deletion of one or more bases of the above-mentioned DNAs by using one or more conventional mutation-introducing methods. The DNAs can be also obtained by applying conventional chemical syntheses based on the nucleotide sequence encoding the present trehalose-releasing enzyme, e.g., one of SEQ ID NO:17. Once in hand, the DNAs according to the present invention can be easily amplified to the desired level by applying or using PCR method and autonomously-replicable vectors.

The present DNA encoding the trehalose-releasing enzyme include those in the form of recombinant DNAs which the DNAs have been introduced into appropriate vectors. The recombinant DNAs can be relatively-easily preparable by recombinant DNA technology in general if only the DNAs are available. Any types of vectors can be used in the present invention as long as they autonomously replicable in appropriate hosts. Examples of such vectors are pUC18, pBluescript II SK(+), pKK223-3, λgt·λC, etc., which use *Escherichia coli* as a host; pUB110, pTZ4, pC194, ρ11, φ1, φ105, etc., which use microorganisms of the genus *Bacillus*; and pHY300PLK, pHV14, TRp7, YEp7, pBS7, etc., which use two or more microorganisms as hosts. The methods to insert the present DNA into such vectors in the present invention may be conventional ones generally used in this field. A gene containing the present DNA and an autonomously-replicable vector are first digested with a restriction enzyme and/or ultrasonic disintegrator, then the resultant DNA fragments and vector fragments are ligated. The ligation is facilitated by the use of restriction enzymes which specifically act on the cleavage of the DNA, especially, KpnI, AccI, BamHI, BstXI, EcoRI, HindIII, NotI, PstI, SacI, SalI, SmaI, SpeI, XbaI, XhoI, etc. To ligate DNA fragments and vectors, firstly they may be annealed if necessary, then subjected to the action of a DNA ligase in vivo or in vitro. The recombinant DNA thus obtained can be replicable without substantial limitation in an appropriate host.

The present DNA encoding the trehalose-releasing enzyme further includes transformants which the DNA has been introduced into appropriate vectors. The transformants can be easily preparable by introducing the DNA or recombinant DNA obtained in the above into appropriate hosts to transform them. As the hosts, microorganisms and cells from plants and animals, which are used conventionally in this field and chosen depending on the vectors in the recombinant DNA, can be used. The microorganisms as hosts include those of the genera *Escherichia, Bacillus*, and *Arthrobacter*, and another actinomycetes, yeasts, fungi, etc. To introduce the present DNA into these host microorganisms, conventional competent cell method and protoplast method can be used. The present DNA, which encodes the trehalose-releasing enzyme introduced into the transformants in the present invention, may be present in a separatory form from chromosomes or in an incorporated form into chromosomes. The DNA incorporated into hosts' chromosomes has a character of being stably retained therein and may be advantageously used in producing the present recombinant protein.

The aforesaid techniques used for obtaining the present DNAs including recombinant DNAs and transformants, and the techniques for obtaining the DNAs and recombinant proteins are commonly used in the art; For example, J. Sumbruck et al. in *"Molecular Cloning A Laboratory Manual"*, 2nd edition, published by Cold Spring Harbor Laboratory Press (1989), discloses in detail methods for obtaining desired DNAs and applications for production use of the obtained DNAs. For example, Japanese Patent No. 2,576,970 discloses a method for stabilizing a transformed DNA, which uses as a host a microorganism defective in an aiming gene. Japanese Patent Kokai No. 157,987/88 discloses a vector which effectively expresses an aiming DNA in microorganisms of the genus *Bacillus*. Japanese Patent Kohyo No. 502,162/93 discloses a method for stably introducing a desired DNA into a bacterial chromosome. Japanese Patent Kohyo No. 506,731/96 discloses an efficient production method of a starch hydrolysing enzyme, using recombinant DNA technology. Japanese Patent Kohyo Nos. 500,543/97 and 500,024/98 disclose a host-vector system using fungi for efficient production of recombinant proteins. These methods conventionally used in the art are arbitrarily applicable for the present invention.

In the art, when the desired DNAs are available by the above methods, there have been commonly provided transformants which the DNAs are introduced into appropriate plants and animals, i.e., transgenic plants and animals. The present DNA, which encodes the non-reducing saccharide-forming enzyme and the trehalose-releasing enzyme in the form of a DNA introduced into appropriate hosts, also includes the transgenic plants and animals. To obtain the transgenic animals, it is obtained as a whole by a process comprising the DNA which encodes either of the present enzymes alone or together with other desired DNA such as a promotor and enhancer into an appropriate vector selected depending on the species of the host animal, introducing the resulting recombinant DNA into a fertilized egg or embryonic stem cell from the host animal by a method such as microinjection and electroporation, or by an infection method using recombinant viruses containing the recombinant DNA. Examples of the host animals are conventional experimental rodents such as mice, rats, and hamsters; and mammals conventionally used as domestic animals such as goats, sheep, pigs, and cows, all of which have an advantage of being bred easily. The resulting cells introduced with the DNA are transplanted in uterine tube or uterus of a pseudopregnancy female animal of the same species as the cells. Thereafter, transgenic animals, which have been introduced with the DNA encoding the present enzymes by applying hybridization or PCR method, are obtained from newborns in a natural or cesarean sectional manner. Thus the present DNA in the form of a transgenic animal can be obtained. Referring to transgenic animals, they are disclosed in detail in *"Jikken-Igaku-Bessatsu-Shin-Idennshi-Kogaku-Handbook"* (Handbook of Genetic Engineering), pp. 269-283 (1996), edited by Masami MATSUMURA, Hiroto OKAYAMA, and Tadashi YAMAMOTO, published by Yodosha Co., Ltd., Tokyo, Japan. The method for obtaining transgenic plants comprises, for example, providing a plasmid as a vector of a microorganism of the genus *Agrobacterium* infectious to plants, introducing the DNA encoding either of the present enzymes into the vector, and either introducing the resulting recombinant DNA into plant bodies or protoplasts, or coating heavy metal particles with a DNA including nucleotide sequence encoding either of the present enzymes and directly injecting the coated particles into plant bodies or protoplasts using a particle gun. Although various types of plants can be used as host plants, they generally include edible plants such as potato, soybean, wheat, burley, rice, corn, tomato, lettuce, alfalfa, apple, peach, melon, etc. By applying hybridization or PCR method for the above transformed plant bodies and protoplasts, transformants containing the desired DNA are selected. The transformed protoplasts can be regenerated into plant bodies as the present DNA in the form of transgenic plants. The techniques of transgenic plants are generally disclosed in *Genetic Engineering*, edited by Jane K. Setlow, published by Plenum Publishing Corporation, NY, USA, Vol. 16, pp. 93-113 (1994). The DNA in the form of the aforesaid transgenic animals and plants can be used as sources of the present non-reducing saccharide-forming enzyme and/or trehalose-releasing enzyme, and used as edible plants and animals which contain trehalose or non-reducing saccharide having a trehalose structure.

The present trehalose-releasing enzyme can be obtained in a desired amount by the present process for producing the enzyme which is characterized in that it comprises culturing a microorganism capable of producing the enzyme in a nutrient culture medium, and collecting the produced enzyme from the resulting culture. Any microorganisms can be used in the present process independently of their genus and species as long as they produce the present trehalose-releasing enzyme. Examples of such microorganisms are those of the genus *Arthrobacter, Arthrobacter* sp. S34, FERM BP-6450, and mutants thereof, as well as transformants obtainable by introducing the present DNA encoding the enzyme into appropriate host microorganisms.

Any nutrient culture media for culturing the process for producing the present trehalose-releasing enzyme can be used as long as the aforesaid microorganisms grow therein and produce the enzyme without restriction to a specific nutrient culture medium. Generally, the nutrient culture media contain carbon and nitrogen sources, and if necessary minerals may be added. Examples of the carbon sources are saccharides such as dextrins, starches, partial starch hydrolysates, glucose, etc., and are saccharide-containing substances such as molasses and yeast extracts, and organic acids such as glucuronic acid and succinic acid. The concentration of the carbon sources is chosen depending on the types used, usually 30 w/v %, and preferably 15 w/w % or lower. Examples of the nitrogen sources appropriately used in the present invention are inorganic-nitrogen-containing substances such as ammonium salts, nitrate, etc.; organic-nitrogen-containing substances such as urea, corn steep liquor, casein, peptone, yeast extract, beef extract, etc. Depending on use, it is selectively used among inorganic ingredients such as salts of calcium, magnesium, potassium, sodium, phosphoric acid, manganese, zinc, iron, copper, molybdenum, cobalt, etc.

The culture conditions used for producing the present trehalose-releasing enzyme can be used selectively from appropriate conditions suitable for growing respective microorganisms used. For example, in the case of using microorganisms of the genus *Arthrobacter* including *Arthrobacter* sp. S34, FERM BP-6450, the cultivation temperature is usually in the range of 20-50° C., and preferably 25-37° C.; the cultivation pH is usually in the range of pH 4-10, and preferably pH 5-9; and the cultivation time is in the range of 10-150 hours. With these conditions, the microorganisms are cultured under aerobic conditions. When used transformants prepared by introducing into appropriate hosts the present DNA encoding the trehalose-releasing enzyme, the transformants are cultured under aerobic conditions at conditions selected from the culture conditions such as the culture temperatures of 20-65° C., the culture pH of 2-9, and the culture time of 1-6 days, although they vary depending on the genus, species, strains or types of microorganisms and vectors. The cultures thus obtained generally contain the enzyme in cell fractions. In the case of culturing transformants obtained by using as hosts the microorganisms of the genus *Bacillus*, the resulting cultures may contain the enzyme in supernatant fractions depending on vectors used to transform the hosts. The content of the enzyme in the cultures thus obtained is usually 0.01-3,000 units per ml of the culture, though it varies depending on the genus, species or strains of the microorganisms and culture conditions used.

The present trehalose-releasing enzyme is collected from the resulting cultures. The collection method is not restricted; The enzyme can be obtained by separating and collecting any one of fractions of cells and culture supernatants found with a major activity of the enzyme, and if necessary subjecting the collected fraction to an appropriate purification method to collect a purified fraction containing the enzyme. To separate the fractions of cells and culture supernatants of the cultures, conventional solid-liquid separation methods such as centrifugation and filtration using precoat filters and plain- and hollow fiber-membranes can be arbitrarily used. The desired fractions are collected from the separated fractions of cells and culture supernatant. For the fraction of cells, the cells are disrupted into a cell disruptant which is then separated into a cell extract and an insoluble cell fraction, followed by collecting either of the desired fractions. The insoluble cell fraction can be solubilized by conventional methods, if necessary. As a method to disrupt cells, any one of techniques of ultrasonication, treatment with cell-wall-lysing enzymes such as lysozyme and glucanase, and load of mechanical press can be arbitrarily used. To disrupt cells the cultures can be directly treated with any one of the above techniques, and then resulting mixtures are treated with any one of the above solid-liquid separation methods to collect a liquid fraction. Thus a cell extract can be arbitrarily obtained.

The methods used for more purifying the present trehalose-releasing enzyme include conventional ones to purify saccharide-related enzymes in general such as salting out, dialysis, filtration, concentration, gel filtration chromatography, ion-exchange chromatography, hydrophobic chromatography, reverse-phase chromatography, affinity chromatography, gel electrophoresis and, isoelectric point electrophoresis. These methods can be used in combination depending on purposes. From the resulting fractions separated by these methods, fractions with a desired activity assayed by the method for trehalose-releasing enzyme are collected to obtain the enzyme purified to a desired level. According to the methods in the later described Examples, the present enzyme can be purified up to an electrophoretically homogenous level. As described above, the present method provide the present trehalose-releasing enzyme in the form of a culture, cell fraction, fraction of culture supernatant, cell disruptant, cell extract, soluble and insoluble cell-fraction, partially purified enzyme fraction, and purified enzyme fraction. These fractions may contain another type of the present non-reducing saccharide-forming enzyme. The present trehalose-releasing enzyme thus obtained can be immobilized in a usual manner before use. The methods for immobilization are, for example, binding method to ion exchangers, covalent bonding/adsorption to and on resins and membranes, and entrapping immobilization method using high molecular weight substances. The trehalose-releasing enzyme thus obtained can be arbitrarily used in processes for producing saccharides including the later described present process for producing saccharide. Particularly, since the trehalose-releasing enzyme has an optimum temperature in a medium temperature range and preferably has an optimum pH in an acid pH range, it can be advantageously used to produce saccharides when used in combination with the later described present trehalose-releasing enzyme, starch-debranching enzyme having an optimum pH in an acid pH range, and cyclomatodextrin glucanotransferase that effectively acts at temperatures in a medium temperature range.

The present invention provides a process for producing saccharides comprising non-reducing saccharides by using the aforesaid present enzymes; the process comprising the steps of allowing the non-reducing saccharide-forming enzyme and/or the trehalose-releasing enzyme to act on reducing partial starch hydrolysates to form non-reducing saccharides, and collecting the resulting non-reducing saccharides or saccharide compositions with a lesser reducibility. In the process, the use of one or more another types of non-reducing saccharide-forming enzymes and trehalose-releasing enzymes other than the present enzymes, and other saccharide-related enzymes should not be excluded from the present invention. The reducing partial starch hydrolysates used in the process can be used independently of their origins/sources. The non-reducing saccharides as referred to in the present invention include non-reducing saccharides in general such as trehalose and those having a trehalose structure.

The reducing partial starch hydrolysates used in the present process for producing saccharides can be obtained, for example, by liquefying starches or amylaceous substances by conventional methods. The starches include terrestrial starches such as corn starch, rice starch, and wheat starch; and subterranean starches such as potato starch, sweet potato starch, and tapioca starch. To liquefy these starches, they are generally suspended in water into starch suspensions, preferably, those with a concentration of at least 10 w/w %, and more preferably those with a concentration of about 20 to about 50 w/w %, and treated with mechanical, acid and/or enzymatic treatments. Relatively-lower degree of liquefaction is satisfactorily used, preferably, DE (dextrose equivalent) of less than 15, and more preferably DE of less than 10. When liquefied with acids, the starches are treated with hydrochloric acid, phosphoric acid, oxalic acid, etc., and then the resulting mixtures are neutralized with calcium carbonate, calcium oxide, sodium carbonate, etc., to desired pHs before use. To liquefy the starches with enzymes, α-amylase, particularly, and thermostable liquefying α-amylase are satisfactorily used. The liquefied starches thus obtained can be further subjected to the action of α-amylase, maltotriose-forming amylase, maltotetraose-forming amylase, maltopentaose-forming amylase, maltohexaose-forming amylase, etc., and the resulting reaction mixtures can be used as the reducing partial starch hydrolysates. The properties of the starch-related enzymes are described in detail in *Handbook of Amylases and Related Enzymes*, pp. 18-81, and pp. 125-142 (1988), published by Pergamon Press.

The reducing partial starch hydrolysates thus obtained are subjected to the action of the present non-reducing saccharide-forming enzyme and/or trehalose-releasing enzyme, and if necessary further subjected to the action of one or more starch-related enzymes such as α-amylase, β-amylase, glucoamylase, starch debranching enzymes such as isoamylase and pullulanase, cyclomaltodextrin glucanotransferase, α-glucosidase, and β-fructofuranosidase. Conditions used for enzymatic reactions are those suitable for enzymes used; Usually they are selected from pHs 4-10 and temperatures of 20-70° C., and preferably pHs 5-7 and temperatures of 30-60° C. Particularly, non-reducing saccharides can be effectively produced by enzymatic reactions at temperatures in a medium temperature range, i.e., temperatures of over 40° C. but below 60° C. or over 45° C. but below 60° C., and pHs of slight acid or acid pH conditions. The order of allowing the enzymes to act on reducing partial starch hydrolysates is not restricted; one proceeds or follows another one, or plural enzymes can be arbitrarily allowed to act on substrates simultaneously.

The amount of enzymes is appropriately set depending on enzymatic conditions and reaction times, and final uses of non-reducing saccharides or less-reducible saccharide compositions containing thereof. For the present non-reducing saccharide-forming enzyme and trehalose-releasing enzyme, the former is used in an amount of about 0.01 to about 100 units/g solid of reducing partial starch hydrolysates, and the latter is used in an amount of about 1 to about 10,000 units/g solid of reducing partial starch hydrolysates. Cyclomatodextrin glucanotransferase is used in an amount of about 0.05 to about 500 units/g reducing partial starch hydrolysates, d.s.b. The reaction mixtures obtained with these enzymes usually contain trehalose, α-glucosyltrehalose, α-maltosyltrehalose, α-maltotriosyltrehalose, α-maltotetraosyltrehalose, or α-maltopentaosyltrehalose. In the above process, when used in combination, the present non-reducing saccharide-forming enzyme and trehalose-releasing enzyme along with a starch debranching enzyme and cyclomatodextrin glucanotransferase characteristically more produce a large amount of trehalose and a relatively-lower molecular weight of non-reducing saccharide having a trehalose structure.

From the resulting reaction mixtures, non-reducing saccharides and saccharide compositions with a lesser reducibility are collected. In these production steps, conventionally used processed for saccharides can be appropriately selected. The resulting reaction mixtures are subjected to filtration and centrifugation to remove insoluble substances, and then the resultant solutions are purified by decoloration with an activated charcoal, desalted with ion exchangers in H— and OH-form, and concentrated into syrupy products. If necessary, the syrupy products can be further purified into non-reducing saccharides with a relatively-high purity; In the purification, one or more methods, for example, column chromatographic fractionations such as ion-exchange column chromatography, column chromatography using an activated charcoal or a silica gel; separatory sedimentation using organic acids such as acetone and alcohol; separation using membranes with an appropriate separability; and alkaline treatments to decompose and remove the remaining reducing saccharides. In particular, ion-exchange column chromatography can be suitably used in the present invention as an industrial-scale preparation of the object saccharides. Non-reducing saccharides with an improved purity can be arbitrary prepared by, for example, column chromatography using a strongly-acid cation exchange resin as described in Japanese Patent Kokai Nos. 23,799/83 and 72,598/83 to remove concomitant saccharides. In this case, any of fixed-bed, moving bed, and semi-moving methods can be employed.

If necessary, the resulting non-reducing saccharides or a relatively-low reducing saccharides containing the non-reducing saccharides can be hydrolyzed by amylases such as α-amylase, β-amylase, glucoamylase and α-glucosidase to control their sweetness and reducing power or to lower their viscosity; and the products thus obtained can be further treated with processings where the remaining reducing saccharides are hydrogenated into sugar alcohols to diminish their reducing powder. Particularly, trehalose can be easily prepared by allowing glucoamylase or α-glucosidase to act on the non-reducing saccharides or relatively-low reducing saccharides containing the non-reducing saccharides. A high trehalose content fraction is obtainable by allowing glucoamylase or α-glucosidase to act on these saccharides to form a mixture of trehalose and glucose, and subjecting the mixture to the aforesaid purification methods such as column chromatography using ion exchangers to remove glucose. The high trehalose content fraction can be arbitrary purified and concentrated into a syrupy product. If necessary, the syrupy product can be concentrated into a supersaturated solution, followed by crystallizing hydrous or anhydrous crystalline trehalose and recovering the resultant crystal.

To produce hydrous crystalline trehalose, an about 65-90 w/w % solution of trehalose with a purity of about 60 w/w % or higher is placed in a crystallizer, and if necessary in the presence of 0.1-20 w/v % seed crystal, gradually cooled while stirring at a temperature of 95° C. or lower, and preferably at a temperature of 10-90° C. to obtain a massecuite containing hydrous crystalline trehalose. Continuous crystallization method to effect crystallization under concentrating conditions in vacuo can be arbitrarily used.

Conventional methods such as separation, block pulverization, fluidized-bed granulation, and spray drying can be employed in the invention to prepare from the massecuite hydrous crystalline trehalose or crystalline saccharides containing the trehalose crystal.

In the case of separation, massecuites are usually subjected to a basket-type centrifuge to separate hydrous crystalline trehalose from a mother liquor, and if necessary the hydrous crystalline trehalose is washed by spraying with a small amount of cold water to facilitate the preparation of hydrous crystalline trehalose with a higher purity. In the case of spray drying, crystalline saccharides with no or substantially free of hygroscopicity are easily prepared by spraying massecuites with a concentration of 70-85 w/w %, on a dry solid basis (d.s.b.), and a crystallinity of about 20-60%, d.s.b., from a nozzle by a high-pressure pump; drying the resultant products with air heated to 60-100° C. which does not melt the resultant crystalline powders; and aging the resultant powders for about 1 to about 20 hours while blowing thereto air heated to 30-60° C. In the case of block pulverization, crystalline saccharides with no or substantially free of hygroscopicity are easily prepared by allowing massecuites with a moisture content of 10-20 w/w % and a crystallinity of about 10-60%, d.s.b., to stand for about 0.1 to about 3 days to crystallize and solidify the whole contents into blocks; and pulverizing or cutting the resultant blocks.

To produce anhydrous crystalline trehalose, the hydrous crystalline trehalose obtained in the above is dried at a normal or reduced pressure at temperatures of 70-160° C., and preferably at 80-100° C.; or a relatively-high concentration and content trehalose solution with a moisture content of less than 10% is placed in a crystallizer, stirred in the presence of a seed crystal at temperatures of 50-160° C., and preferably 80-140° C. to produce a massecuite containing anhydrous crystalline trehalose, and treating the massecuite with methods such as block pulverization, fluidized-bed granulation, and spray drying under relatively-high temperatures and drying conditions.

The non-reducing saccharides or saccharide composition, containing thereof with a relatively-low reducibility, thus obtained are low in reducibility and satisfactory in stability; they do not become browning, form indisagreeable smell, and deteriorate the following another materials when mixed and processed with another materials, for example, amino-acid-containing substances such as amino acids, oligopeptides, and proteins. Even with a relatively-low reducibility, the above-identified saccharides have a relatively-low viscosity, and those with a relatively-low average glucose polymerization degree have a relatively-high quality and sweetness. These saccharides can be arbitrarily used in the fields of foods, cosmetics, and pharmaceuticals, etc., as disclosed in Japanese Patent Kokai Nos. 66,187/96, 66,188/96, 73,482/96, 73,506/96, 73,504/96, 336,363/96, 9,986/97, 154,493/97, 252,719/97, 66,540/98, and 168,093/98; and Japanese Patent Application Nos. 236,441/97, 256,219/97, 268,202/97, 274, 962/97, 320,519/97, 338,294/97, 55,710/98, 67,628/98, 134, 553/98 and 214,375/98, which were all applied for by the same applicant as the present applicant.

The following examples describe the present invention in more detail:

EXAMPLE 1

Microorganism Capable of Producing Non-reducing Saccharide-forming Enzyme and Trehalose-releasing Enzyme The present inventors widely screened soils to isolate a microorganism capable of producing non-reducing saccharide-forming enzyme and trehalose-releasing enzyme. As a result, they isolated a microorganism with such a property from a soil in Ako, Hyogo, Japan, and identified the microorganisms in accordance with the method as described in "*Biseibutsu-no-Bunrui-to-Dotei*" (Classification and Identification of Microorganisms), edited by Takeji Hasegawa, published by Japan Scientific Societies Press, Tokyo, Japan (1985). The results were as follows:

Results on Cell Morphology
(1) Characteristics of cells when incubated at 37° C. in nutrient agar broth
  Usually existing a rod form of 0.4-0.5×0.8-1.2 μm; Existing in a single form but uncommonly existing in a polymorphic form;
  Free of motility;
  Asporogenic;
  Non-acid fast; and
  Gram stain: Positive.
(2) Characteristics of cells when incubated at 37° C. in EYG nutrient agar
  Exhibiting a growth cycle of rods and cocci.

Results on Cultural Property
(1) Characteristics of colony formed when incubated at 37° C. in nutrient agar broth plate
  Shape: Circular colony having a diameter of about 1-2 mm after 2-days incubation;
  Rim: Entire;
  Projection: Convex;
  Gloss: Moistened gloss;
  Surface: Plain; and
  Color: Semi-transparent or cream.
(2) Characteristics of colony formed when incubated at 37° C. in nutrient agar broth slant
  Growth: Satisfactory; and
  Shape: Thread-like.
(3) Characteristics of colony formed when incubated at 37° C. in agar slant with yeast extract and peptone
  Growth: Satisfactory; and
  Shape: Thread-like.
(4) Characteristics of colony formed when stab-cultured at 27° C. in nutrient gelatin broth Not liquefying gelatin.

Results on Physiological Properties
(1) Methyl red test: Negative
(2) VP-test: Positive
(3) Formation of indole: Negative
(4) Formation of hydrogen sulfide: Negative
(5) Hydrolysis of starch: Positive
(6) Liquefaction of gelatin: Negative
(7) Utilization of citric acid: Positive
(8) Utilization of inorganic nitrogen source: Utilizing nitrate but not ammonium salts
(9) Formation of pigment: Non
(10) Urease: Negative
(11) Oxidase: Negative
(12) Catalase: Positive
(13) Growth range: Growing at pHs of 4.5-8.0 and temperatures of 20-50° C.; and Optimum temperatures of 30-45° C.
(14) Oxygen requirements: Aerobic
(15) Utilization of carbon sources
  L-Arabinose: Assimilated
  D-Glucose: Assimilated
  D-Fructose: Not assimilated
  D-Galactose: Not assimilated
  L-Rhamnose: Not assimilated
  D-Xylose: Not assimilated
  D-Mannose: Assimilated
  Raffinose: Not assimilated
  Trehalose: Not assimilated
  Sucrose: Not assimilated
  Maltose: Not assimilated
  Lactose: Not assimilated
  D-Dulcitol: Not assimilated
  D-Mannitol: Not assimilated
  Gluconic acid: Assimilated
  Succinic acid: Assimilated
  Nicotinic acid: Not assimilated
  L-Maleic acid: Assimilated
  Acetic acid: Assimilated
  Lactic acid: Assimilated
(16) Acid formation from sugars
  L-Arabinose: Slightly formed
  D-Glucose: Slightly formed
  D-fructose: Not formed
  D-Galactose Slightly formed
  L-Rhamnose Slightly formed
  D-Xylose: Slightly formed
  Glycerol: Slightly formed Raffinose: Not formed
Trehalose: Slightly formed
Sucrose: Slightly formed
Maltose: Slightly formed
Lactose: Not formed

(17) Utilization of amino acid
   Not utilizing sodium L-glutamate, sodium L-aspartate, L-histidine and L-arginine,
(18) Decarboxylase test on amino acid
   Negative against L-lysine, L-ornithine and L-arginine.
(19) DNase: Negative
(20) N-Acyl type of cell wall: Acetyl
(21) Main diamino acid of cell wall: Lysine
(22) Mol % of guanine (G) plus cytosine (C) of DNA: 71.2%

These bacteriological properties were compared with those of known microorganisms with reference to *Bergey's Manual of Systematic Bacteriology*, Vol. 2 (1984). As a result, it was revealed that the microorganism was identified as a novel one of the genus *Arthrobacter*. Based on the results, the present inventors named this microorganism "*Arthrobacter* sp. S34". The microorganisms was deposited and accepted on Aug. 6, 1998, under the accession number of FERM BP-6450 in and by the Patent Microorganism Depository, National Institute of Bioscience and Human-Technology Agency of Industrial Science & Technology, Ministry of International Trade & industry, 1-3, Higashi, 1 chome, Tsukuba-shi, Ibaraki-ken 305-8566, Japan.

The homology of DNA between the identified microorganism and type-strains of the genus *Arthrobacter*, deposited in American Type Culture Collection (ATCC), an international depository of microorganism in USA, was examined in accordance with the DNA-DNA hybridization method in *Bergey's Manual of Systematic Bacteriology*, Vol. 1 (1984). Twelve type-strains shown in Table 1 in the below were respectively cultured in a usual manner, and proliferated cells were collected from the resulting cultures. *Arthrobacter* sp. S34, FERM BP-6450, was cultured by the seed culture method in the later described Example 2-1, followed by collecting the proliferated cells. According to conventional method, DNAs were obtained from each type-strain of microorganisms, two micrograms aliquots of the DNAs were digested with a restriction enzyme, Pst I. The resulting digested mixtures were respectively spotted on "Hybond-N+", a nylon membrane commercialized by Amersham International, Arlington Heights, Ill., USA, and in a usual manner, treated with alkali, neutralized, and dried to fix the DNAs on the nylon membrane. One microgram of the DNA obtained from *Arthrobacter* sp. S34, FERM BP-6450, was provided and digested with Pst I. Using [$\alpha$-$^{32}$P] dCTP commercialized by Amersham International, Arlington Heights, Ill., USA, and "READY-TO-GO DNA-LABELLING KIT", a DNA-labelling kit commercialized by Pharmacia LKB Biotechnology AB, Uppsala, Sweden, the digestant was labelled with an isotope to obtain a probe. The probe and the above DNA fixed on nylon film were hybridized for two hours under shaking conditions at 65° C. in "RAPID HYBRIDIZATION BUFFER", a buffer for hybridization commercialized by Amersham Corp., Div., Amersham International, Arlington Heights, Ill., USA. The nylon film after hybridization was washed in a usual manner, dried and subjected to autoradiography in a usual manner. Signals of hybridization observed on radiography were analyzed on "IMAGE MASTER", an image analyzing system commercialized by Pharmacia LKB Biotechnology AB, Uppsala, Sweden, followed by expressing numerically the intensity of the signals for hybridization. Based on the numerals, the relative intensities (%) of spots for the DNAs derived from the type-strains were calculated by regarding the signal intensity of a spot for the DNA from *Arthrobacter* sp. S34, FERM BP-6450, as 100 and used as an index for the DNA homology between the microorganism and the type-strains. The results are in Table 1.

TABLE 1

| Strain of microorganism | Signal intensity of hybridization |
|---|---|
| *Arthrobacter atrocyaneus*, ATCC 13752 | 42.0 |
| *Arthrobacter aurescens*, ATCC 13344 | 12.4 |
| *Arthrobacter citreus*, ATCC 11624 | 36.2 |
| *Arthrobacter crystallpoietes*, ATCC 15481 | 31.6 |
| *Arthrobacter globiformis*, ATCC 8010 | 55.1 |
| *Arthrobacter nicotianae*, ATCC 15236 | 18.8 |
| *Arthrobacter oxydans*, ATCC 14358 | 28.3 |
| *Arthrobacter pascens*, ATCC 13346 | 24.6 |
| *Arthrobacter protophormiae*, ATCC 19271 | 29.3 |
| *Arthrobacter ramosus*, ATCC 13727 | 98.6 |
| *Arthrobacter ureafaciens*, ATCC 7562 | 42.3 |
| *Arthrobacter viscous*, ATCC 19584 | 0.0 |
| *Arthrobacter* sp. S34, FERM BP-6450 | 100 |

As shown in Table 1, the signal intensity of hybridization for the spot of DNA from *Arthrobacter ramosus* type strain, ATCC 13727, was as high as 98.6%. The data revealed that *Arthrobacter* sp. S34, FERM BP-6450, had the highest homology with *Arthrobacter ramosus* type-strain, ATCC 13727, among the 12 type strains used in this Example. The results in the above shows that *Arthrobacter* sp. S34, FERM BP-6450, is a novel microorganism nearly related to *Arthrobacter ramosus* type-strain, ATCC 13727.

EXAMPLE 2

Non-reducing Saccharide-forming Enzyme

Experiment 2-1

Preparation of Enzyme

A nutrient culture medium, consisting of 1.0 w/v % "PINE-DEX #4", a dextrin commercialized by Matsutani Chemical Ind., Tokyo, Japan, 0.5 w/v % peptone, 0.1 w/v % yeast extract, 0.1 w/v % monosodium phosphate, 0.06 w/v % dipotassium hydrogen phosphate, 0.05 w/v % magnesium sulfate, and water, was prepared and adjusted to pH 7.0. About 100 ml aliquots of the medium were placed in 500-ml Erlenmeyer flasks which were then autoclaved at 120° C. for 20 min and cooled, followed by an inoculation of a seed of *Arthrobacter* sp. S34, FERM BP-6450 and a culture at 37° C. for 48 hours under stirring conditions of 260 rpm for obtaining a seed culture.

Except for containing 0.05 w/v % of "KM-75", a anti-foamer commercialized by Shin-Etsu Chemical, Co., Ltd, Tokyo, Japan, an about 20 l of the same nutrient culture medium as used in the seed culture was placed in a 30-l fermenter, sterilized, cooled to 37° C., and inoculated with one v/v % of the seed culture to the medium, followed by an incubation at 37° C. and pHs of 5.5-7.5 for about 72 hours under aeration-agitation conditions.

A portion of the resultant culture was sampled, centrifuged to separate into cells and a culture supernatant. The cells were ultrasonically disrupted and centrifuged to collect supernatant for a cell extract. Assay for non-reducing saccharide-forming enzyme activity in each culture supernatant and cell extract revealed that the former showed a relatively-low enzyme activity and the latter exhibited an about 0.1 unit with respect to one milliliter of the culture.

EXAMPLE 2-2

Purification of Enzyme

An about 80 l of a culture, obtained according to the method in Example 2-1, was centrifuged at 8,000 rpm for 30 min to obtain an about 800 g cells by wet weight. The wet cells were suspended in two liters of 10 M phosphate buffer (pH 7.0) and treated with "MODEL UH-600", an ultrasonic homogenizer commercialized by SMT Co., Tokyo, Japan. The resulting solution was centrifuged at 10,000 rpm for 30 min to yield an about 2 l of a culture supernatant. To and in the culture supernatant was added and dissolved ammonium sulfate to give a saturation degree of 0.7, and the mixture was allowed to stand at 4° C. for 24 hours and centrifuged at 10,000 rpm for 30 min to obtain a precipitate. The precipitate thus obtained was dissolved in 10 mM phosphate buffer (pH 7.0) and dialyzed against a fresh preparation of the same buffer as above for 48 hours, followed by centrifuging the dialyzed inner solution at 10,000 rpm for 30 min to remove insoluble substances. An about one liter of the resulting solution was subjected to an ion-exchange column chromatography using a column packed with about 1.3 l of "SEPABEADS FP-DA13 GEL", an anion exchanger commercialized by Mitsubishi Chemical Industries Ltd., Tokyo, Japan. The elution step was carried out using a linear gradient buffer of 10 mM phosphate buffer (pH 7.0) containing salt which increased from 0 M to 0.6 M. The eluate from the column was fractionated, and the fractions were respectively assayed for non-reducing saccharide-forming enzyme activity. As a result, the enzyme activity was remarkably found in fractions eluted with buffer having a salt concentration of about 0.2 M, followed by pooling the fractions.

Ammonium sulfate was added to the resulting solution to give a concentration of 1 M, and the mixture was allowed to stand at 4° C. for 12 hours, centrifuged at 10,000 rpm for 30 min to collect a supernatant. The supernatant thus obtained was subjected to hydrophobic column chromatography using a column packed with "BUTYL TOYOPEARL 650M GEL", a hydrophobic gel commercialized by Tosoh Corporation, Tokyo, Japan. The gel volume used was about 300 ml and used after equilibrated with 10 mM phosphate buffer (pH 7.0) containing 1 M ammonium sulfate. The elution step was carried out using a linear gradient buffer of 10 mM phosphate buffer (pH 7.0) containing ammonium sulfate which decreased from 1 M to 0 M during the feeding. The eluate from the column was fractionated, and the fractions were respectively assayed for non-reducing saccharide-forming enzyme activity. As a result, the enzyme activity was remarkably found in fractions eluted with buffer having a salt concentration of about 0.75 M, followed by pooling the fractions.

The resulting solution was dialyzed against 10 mM phosphate buffer (pH 7.0), and the resulting dialyzed inner solution was centrifuged at 10,000 rpm for 30 min to collect a supernatant, followed by subjecting the supernatant to ion-exchange column chromatography using a column packed with about 40 ml of "DEAE TOYOPEARL 650S GEL", an anion exchanger commercialized by Tosoh Corporation, Tokyo, Japan. The elution step was carried out using a linear aqueous salt solution which increased from 0 M to 0.2 M during the feeding. The eluate from the column was fractionated, and the fractions were respectively assayed for non-reducing saccharide-forming enzyme activity. As a result, the enzyme activity was remarkably found in fractions eluted with buffer having a salt concentration of about 0.15 M, followed by pooling the fractions. The resulting solution was further subjected to gel filtration column chromatography using a column packed with about 380 ml of "ULTROGEL® AcA44 GEL", a gel for gel filtration column chromatography commercialized by Sepracor/IBF s.a. Villeneuve la Garenne, France, followed by collecting fractions with the desired enzyme activity. The level of the non-reducing saccharide-forming enzyme activity, specific activity, and yields in the above purification steps are in Table 2.

TABLE 2

| Purification step | Enzyme activity of non-reducing saccharide-forming enzyme | Specific activity (unit/mg protein) | Yield (%) |
| --- | --- | --- | --- |
| Cell extract | 8,000 | — | 100 |
| Dialyzed inner-solution after salting out with ammonium salt | 7,500 | 0.2 | 94 |
| Eluate from SEPABEADS column | 5,200 | 0.7 | 65 |
| Eluate from hydrophobic column | 2,600 | 6.3 | 33 |
| Eluate from TOYO PEARL | 910 | 67.4 | 11 |
| Eluate of gel filtration | 59.0 | 168 | 0.7 |

The solution eluted and collected from the above gel filtration chromatography was in a usual manner subjected to electrophoresis using 7.5 w/v % polyacrylamide gel and resulted in a single protein band. The data shows that the eluate from gel filtration chromatography was a purified specimen of a non-reducing saccharide-forming enzyme purified up to an electrophoretically homogeneous form.

EXAMPLE 2-3

Property of Enzyme

EXAMPLE 2-3(a)

Action

A 20% aqueous solution containing glucose, maltose, maltotriose, maltotetraose, maltopentaose, maltohexaose or maltoheptaose as a substrate for enzyme was prepared, mixed with two units/g substrate, d.s.b., of a purified specimen of a non-reducing saccharide-forming enzyme obtained by the method in Example 2-2, and enzymatically reacted at 50° C. and pH 6.0 for 48 hours. The reaction mixture was desalted and analyzed on high-performance liquid chromatography (abbreviated as "HPLC" hereinafter) using two columns of "MCI GEL CK04SS COLUMN", commercialized by Mitsubishi Chemical Industries Ltd., Tokyo, Japan, which were cascaded in series, followed by determining the saccharide composition of the reaction mixture. The conditions and apparatus used in HPLC were as follows: The column was kept at 85° C. using "Co-8020", a column oven commercialized by Tosoh Corporation, Tokyo, Japan. Water as a moving phase was fed at a flow rate of 0.4 ml/min. The eluate was analyzed on "RI-8020", a differential refractometer commercialized by Tosoh Corporation, Tokyo, Japan. The results were in Table 3.

TABLE 3

| Substrate | Reaction product | Elution time (min) | Percentage (%) |
|---|---|---|---|
| Glucose | Glucose | 57.2 | 100.0 |
| Maltose | Maltose | 50.8 | 100.0 |
| Maltotriose | Glucosyltrehalose | 43.2 | 36.2 |
|  | Maltotriose | 46.2 | 63.8 |
| Maltotetraose | Maltosyltrehalose | 38.9 | 87.2 |
|  | Maltotetraose | 42.3 | 12.8 |
| Maltopentaose | Maltotriosyltrehalose | 35.4 | 93.0 |
|  | Maltopentaose | 38.4 | 7.0 |
| Maltohexaose | Maltotetraosyltrehalose | 32.7 | 93.8 |
|  | Maltohexaose | 35.2 | 6.2 |
| Maltoheptaose | Maltopentaosyltrehalose | 30.2 | 94.2 |
|  | Maltoheptaose | 32.4 | 5.8 |

As evident form the results in Table 3, each reaction product consisted essentially of the remaining substrate and a newly formed non-reducing saccharide of α-glucosyltrehalose, α-maltosyltrehalose, α-maltotriosyltrehalose, α-maltotetraosyltrehalose, or α-maltopentaosyltrehalose (in Table 3, it is expressed as glucosyltrehalose, maltosyltrehalose, maltotriosyltrehalose, maltotetraosyltrehalose, or maltopentaosyltrehalose). Substantially no other saccharide was detected in the reaction mixture. Regarding and evaluating the percentage of non-reducing saccharide in each reaction product as a production yield, it was revealed that the yield of α-glucosyltrehalose having a glucose polymerization degree of 3 was relatively low and the yield of those having a glucose polymerization degree of 4 or higher such as α-maltosyltrehalose, α-maltotriosyltrehalose, α-maltotetraosyltrehalose, and α-maltopentaosyltrehalose was as high as about 85% or higher. No formation of non-reducing saccharide from glucose and maltose was observed.

EXAMPLE 2-3(b)

Molecular Weight

A purified specimen of a non-reducing saccharide-forming enzyme, obtained by the method in Example 2-2, was subjected to SDS-PAGE using 10 w/v % polyacrylamide gel in a usual manner in parallel with molecular markers commercialized by Japan Bio-Rad Laboratories, Tokyo, Japan. Comparing with the positions of the molecular markers after electrophoresis, the non-reducing saccharide-forming enzyme exhibited a molecular weight of about 75,000±10,000 daltons.

EXAMPLE 2-3(c)

Isoelectric Point

A purified specimen of a non-reducing saccharide-forming enzyme, obtained by the method in Example 2-2, was isoelectrophoresed using a polyacrylamide gel containing 2 w/v % "AMPHOLINE", an ampholyte, commercialized by Pharmacia LKB Biotechnology AB, Uppsala, Sweden. After isoelectrophoresis, the measurement of the pH of gel revealed that the non-reducing saccharide-forming enzyme had an isoelectric point of about 4.5±0.5.

EXAMPLE 2-3(d)

Optimum Temperature and pH

Figure 1:
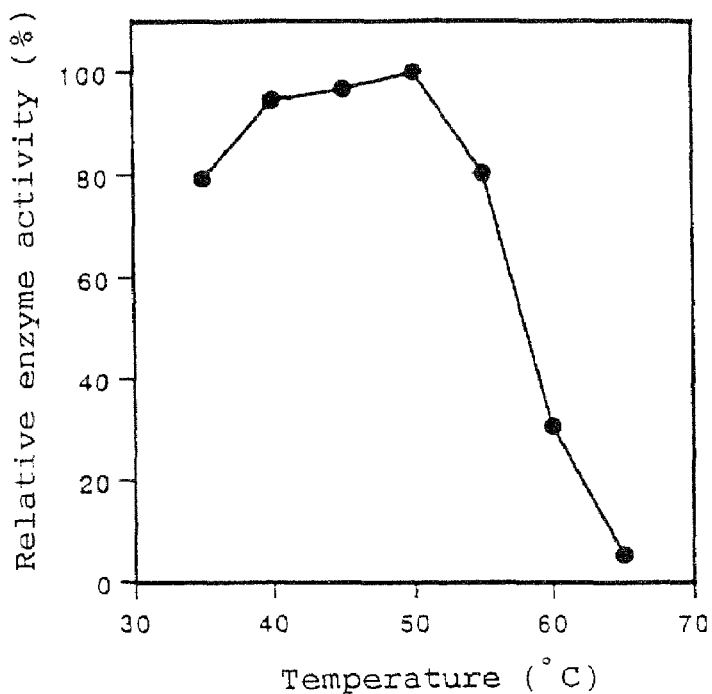
FIG. 1 is a figure that shows the influence of temperature on the activity of a non-reducing saccharide-forming enzyme from *Arthrobacter* sp. S34, FERM BP-6450, according to the present invention.
Figure 2:
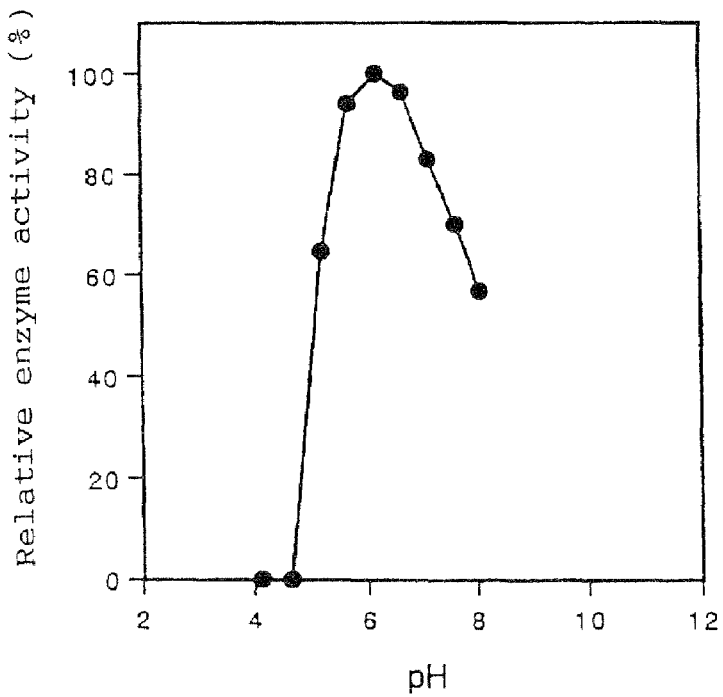
FIG. 2 is a figure that shows the influence of pH on the activity of a non-reducing saccharide-forming enzyme from *Arthrobacter* sp. S34, FERM BP-6450, according to the present invention.

Using a purified specimen of a non-reducing saccharide-forming enzyme, obtained by the method in Example 2-2, it was examined the influence of temperature and pH on the activity of the non-reducing saccharide-forming enzyme. When examining the influence of temperature, it was conducted similarly as in the assay for enzyme activity except for reacting the enzyme at different temperatures. In the examination of the influence of pH, it was conducted similarly as in the assay for enzyme activity except for reacting the enzyme at different pHs using appropriate 20 mM buffers. In each examination, a relative value (%) of a lowered level of reducing power of substrate in each reaction system was calculated into its corresponding relative enzyme activity (%). FIG. 1 shows a result of the influence of temperature, and FIG. 2 is of pH. The cross axles in FIGS. 1 and 2 show reaction temperatures and reaction pHs, respectively. As shown in FIG. 1, the optimum temperature of the enzyme was about 50° C. when incubated at pH 6.0 for 60 min. Also as shown in FIG. 2, the optimum pH of the enzyme was a pH of about 6.0 when incubated at 50° C. for 60 min.

EXAMPLE 2-3(e)

Thermal and pH Stabilities

Figure 3:
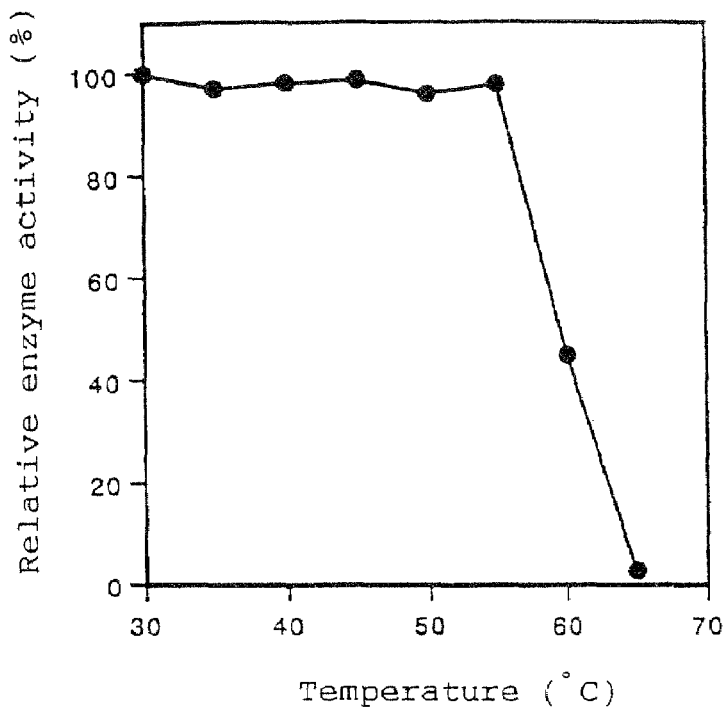
FIG. 3 is a figure that shows the influence of temperature on the stability of a non-reducing saccharide-forming enzyme from *Arthrobacter* sp. S34, FERM BP-6450, according to the present invention.
Figure 4:
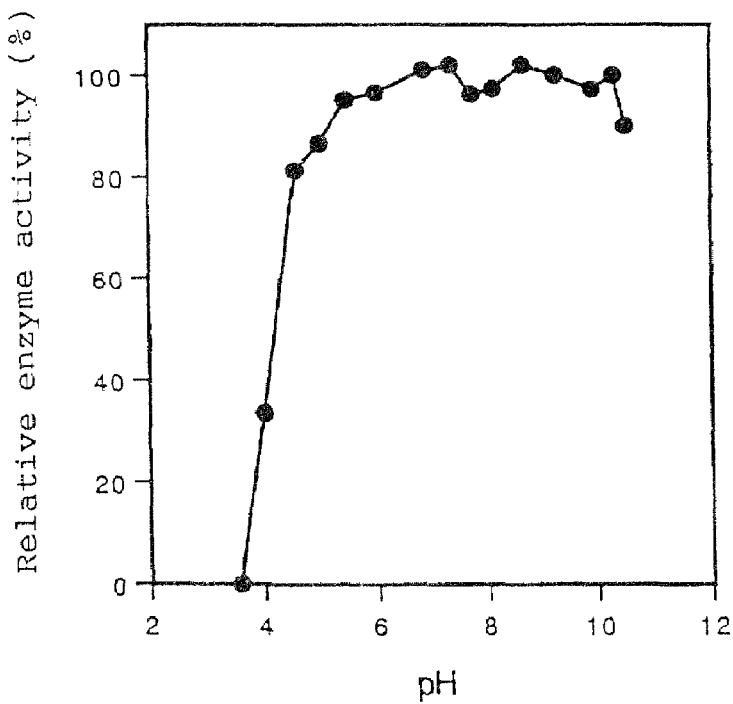
FIG. 4 is a figure that shows the influence of pH on the stability of a non-reducing saccharide-forming enzyme from *Arthrobacter* sp. S34, FERM BP-6450, according to the present invention.

Using a purified specimen of a non-reducing saccharide-forming enzyme, obtained by the method in Example 2-2, it was examined the thermal and pH stabilities of the enzyme. The thermal stability was examined by diluting the specimen with 20 mM phosphate buffer (pH 7.0), incubating the dilutions at prescribed temperatures for 60 min, cooling the incubated dilutions, and determining the remaining enzyme activity in the dilutions according to the method of the assay for the enzyme activity. The pH stability of the enzyme was examined by diluting the specimen with 50 mM buffers with appropriate different pHs, incubating the dilutions at 4° C. for 24 hours, adjusting the dilutions to pH 6, and determining the remaining enzyme activity in the dilutions according to the method of the assay for the enzyme activity. The results of the thermal and pH stabilities of the enzyme are respectively shown in FIGS. 3 and 4. The cross axles in FIGS. 3 and 4 show incubation temperatures and pHs for the enzyme, respectively. As shown in FIG. 3, the enzyme was stable up to about 55° C. and was stable at pHs in the range of about 5.0 to about 10.0 as shown in FIG. 4.

These results evidence that the non-reducing saccharide forming-enzyme, obtained by the method in Example 2-2, is the present non-reducing saccharide-forming enzyme having an optimum temperature in a medium temperature range.

EXAMPLE 2-4

Partial Amino Acid Sequence

A portion of a purified specimen of a non-reducing saccharide-forming enzyme, obtained by the method in Example 2-2, was dialyzed against distilled water to obtain an about 80 μg of a sample by weight as a protein for analyzing the N-terminal amino acid sequence. Using "PROTEIN SEQUENCER MODEL 473A", a protein sequencer commercialized by Applied Biosystems, Inc., Foster City, USA, the N-terminal amino acid sequence was analyzed up to 20 amino acid residues from the N-terminus. The revealed N-terminal amino acid sequence was the partial amino acid sequence of SEQ ID NO:4. A portion of a purified specimen of a non-reducing saccharide-forming enzyme, obtained by the method in Example 2-2, was dialyzed against 10 mM Tris-HCl buffer (pH 9.0) and in a usual manner concentrated up to an about one mg/ml solution using "ULTRACENT-30", an ultrafiltration membrane commercialized by Tosoh Corporation, Tokyo, Japan. To 0.2 ml of the concentrate was added 10 μg "TPCK-TRYPSIN", a reagent trypsin commercialized by Wako Pure Chemical Industries, Ltd., Tokyo, Japan, allowed to react at 30° C. for 22 hours to digest the enzyme to form peptides. The peptides were separated by subjecting the reaction mixture to reverse-phase HPLC using "μ BONDASPHERE C18 COLUMN" having a diameter of 3.9 mm and a length of 150 mm, a product of Waters Chromatography Div., MILLIPORE Corp., Milford, USA. The elution step was carried out at ambient temperature by feeding to the column an aqueous solution containing 0.1 v/v % trifluoro acetate and acetonitrile increasing from 24 to 48 v/v % for 60 min during the feeding at a flow rate of 0.9 ml/min. The peptides eluted from the column were detected by monitoring the absorbance at a wavelength of 210 nm. Two peptides, which were well separated from others, i.e., "S5" eluted at a retention time of about two hours and "S8" eluted at a retention time of about 30 min were separated, respectively dried in vacuo, and dissolved in 50 v/v % aqueous acetonitrile solutions containing 50 μl of 0.1 v/v % trifluoro acetate. The peptide solutions were subjected to the protein sequencer to analyze up to 20 amino acid residues. From peptides "S5" and "S8" the amino acid sequences of SEQ ID Nos:5 and 6 were obtained.

EXAMPLE 3

DNA Encoding Non-reducing Saccharide-forming Enzyme

EXAMPLE 3-1

Construction and Screening of Gene Library

Except for setting temperature and time for culture were respectively set to 27° C. and 24 hours, *Arthrobacter* sp. S34, FERM BP-6450, was cultured similarly as in Example 2-1.

The culture was centrifuged to remove cells which were then suspended in an adequate amount of Tris-EDTA-salt bufferred saline (hereinafter designated as "TES buffer") (pH 8.0), admixed with lysozyme in an amount of 0.05 w/v % to the cell suspension by volume, followed by an incubation at 37° C. for 30 min. The resultant mixture was freezed by standing at –80° C. for one hour, and then admixed and sufficiently stirred with a mixture of TES buffer and phenol preheated to 60° C., cooled, and centrifuged to collect the formed supernatant. To the supernatant was added cold ethanol was added, and then the formed sediment was collected, dissolved in an adequate amount of SSC buffer (pH 7.1), admixed with 7.5 μg ribonuclease and 125 μg protease, and incubated at 37° C. for one hour. The resulting mixture was admixed and stirred with chloroform/isoamyl alcohol, and allowed to stand, followed by collecting the formed upper layer, adding cold ethanol to the layer, and collecting the formed sediment. The sediment was rinsed with a cold 70 v/v ethanol, dried in vacuo to obtain a DNA, followed by dissolving in SSC buffer (pH 7.1) to give a concentration of about one mg/ml, and freezing at –80° C.

Fifty microliters of the DNA was provided, admixed with an abut 50 units of KpnI as an restriction enzyme, and incubated at 37° C. for one hour to digest the DNA. Three micrograms of the digested DNA and 0.3 microgram of "pBluescript II SK (+)", a plasmid vector commercialized by Stratagene Cloning Systems, California, USA, was weighed, subjected to the action, were ligated using "DNA LIGATION KIT", commercialized by Takara Shuzo Co., Ltd., Tokyo, Japan, according to the protocol affixed to the kit. According to conventional competent cell method, 100 μl of "Epicurian Coli XL1-Blue", an *Escherichia coli* strain commercialized by Stratagene Cloning Systems, California, USA, was transformed with the ligated product. Thus a gene library was obtained.

The gene library thus obtained was inoculated to a agar nutrient plate medium (pH 7.0) containing 10 g/l tryptone, 5 g/l yeast extract, 5 g/l sodium chloride, 75 mg ampicillin sodium salt, and 50 mg/l 5-bromo-4-chloro-indolyl-β-galactoside, and incubated at 37° C. for 18 hours. About 5,000 white colonies formed on the medium were in a usual manner fixed on "HYBOND-N-+", a nylon film commercialized Amersham Corp., Div. Amersham International, Arlington Heights, Ill., USA. Based on 1-8 amino acid residues in the amino acid sequence of SEQ ID NO:5 revealed in Example 2-4, an oligonucleotide having the nucleotide sequence of SEQ ID NO:18 was chemically synthesized, and in a usual manner labelled with [γ-$^{32}$P] ATP and T4 polynucleotide kinase to obtain a probe. Using the probe, the colonies, which had been fixed on the nylon film and obtained previously, were screened by conventional colony hybridization method. The hybridization was carried out at 65° C for 16 hours in a solution for hybridization containing 6×SSC, 5× Denhalt solution, and 100 mg/l of denatured salmon sperm DNA. The above nylon film after the hybridization was washed with 6×SSC at 65° C. for 30 min, and further washed with 2×SSC containing 0.1 w/v % SDS at 65° C. for two hours. The resulting nylon film was in a usual manner subjected to autoradiography, and then, based on the signals observed on the autoradiography, a colony which strongly hybridized with the probe was selected and named "GY1" as a transformant.

EXAMPLE 3-2

Decoding of Nucleotide Sequence

According to conventional manner, the transformant GY1 was inoculated to L-broth (pH 7.0) containing 100 μg/ml ampicillin in a sodium form, and cultured at 37° C. for 24 hours under shaking conditions. After completion of the culture, the proliferated cells were collected from the culture by centrifugation and treated with conventional alkali-SDS method to extract a recombinant DNA. The recombinant DNA was named pGY1. Using the above probe, the recombinant DNA, pGY1, was analyzed on conventional Southern blot technique, and based on the analytical data a restriction map was constructed as shown in FIG. 5. As shown in FIG. 5, it was revealed that the recombinant DNA, pGY1, contained a nucleotide sequence consisting of bases of about 5,500 base-pairs (bp) from *Arthrobacter* sp. S34, FERM BP-6450, expressed with a bold line, and that the recombinant DNA contained a nucleotide sequence encoding the present non-reducing saccharide-forming enzyme, as indicated with a black arrow within the area of the bold line, in the area consisting bases of about 4,000 bp between two recognition sites by a restriction enzyme, EcoRI. Based on the result, the recombinant DNA, pGY1, was completely digested with EcoRI, and then a DNA fragment of about 4,000 bp was separated and purified using conventional agarose gel electrophoresis. The DNA fragment and "pBluescript II SK (+)", a plasmid vector commercialized by Stratagene Cloning Systems, California, USA, which had been previously digested with EcoRI, were ligated with conventional ligation method. With the ligated product, "XL1-BLUE", an *Escherichia coli* strain commercialized by Stratagene Cloning Systems, California, USA, was transformed to obtain a transformant. A recombinant DNA was extracted from the transformant in a usual manner, confirming in a usual manner that it contained the aforesaid DNA fragment consisting of about bases of 4,000 bp, and named it "pGY2". The transformant introduced with "pGY2" was named "GY2".

The analysis of the nucleotide sequence of the recombinant DNA pGY2 on conventional dideoxy method revealed that it contained the nucleotide sequence of SEQ ID NO:19 consisting bases of 3252 bp derived from *Arthrobacter* sp. S34, FERM BP-6450. The nucleotide sequence encodes the amino acid sequence as shown in parallel in SEQ ID NO:19. Comparing the amino acid sequences of SEQ D NOs:4 to 6 as partial amino acid sequences of the present non-reducing saccharide-forming enzyme confirmed in Example 2-4, the amino acid sequences of SEQ ID Nos:4 to 6 were perfectly coincided with the amino acids 2-21, 619-638, and 98-117 in SEQ ID NO:19. These data indicate that the present non-reducing saccharide-forming enzyme obtained in Example 2 consists of the amino acids 2-757 of SEQ ID NO:19, or has the amino acid Sequence of SEQ ID NO:1, and that the enzyme of *Arthrobacter* sp. S34, FERM BP-6450, is encoded by a nucleotide sequence of bases 746-3013 of SEQ ID NO:19, or encoded by the nucleotide sequence of SEQ ID NO:7. The structure of the recombinant DNA pGY2 is in FIG. 6.

The above-identified amino acid sequence of the present non-reducing saccharide-forming enzyme obtained by the method in Example 2, and amino acid sequences of known enzymes having a non-reducing saccharide-forming activity were compared using "GENETYX-MAC, VER. 8", a commercially available computer program commercialized by Software Development Co., Ltd., Tokyo, Japan, according to the method by Lipman, David J. in *Science*, Vol. 227, pp. 1,435-1,441 (1985) to calculate their homology (%). The enzymes used as known enzymes were those from *Arthrobacter* sp. Q36 and *Rhizobium* sp. M-11 disclosed in Japanese Patent Kokai No. 322,883/95; *Sulfolobus acidocaldarius*, ATCC 33909, disclosed in Japanese Patent Kokai No. 84,586/96; and *Sulfolobus solfataricus* KM1 disclosed in Sai-Kohyo No. WO 95/34642. As disclosed in the above publications, the conventional enzymes have optimum temperatures other than a medium temperature range. The information of amino acid sequences of conventional enzymes is obtainable from the GeneBank, a DNA database produced by the National Institutes of Health (NIH), USA, under the accession numbers of D63343, D64128, D78001 and D83245. The obtained homologies are in Table 4.

TABLE 4

| Origin of enzyme for amino acid sequence(*) comparison | Homology on amino acid sequence |
|---|---|
| *Rhizobium* sp. M-11 (D78001) | 56.9% |
| *Arthrobacter* sp. Q36 (D63343) | 56.6% |
| *Sulfolobus solfataricus* KM1 (D64128) | 33.2% |
| *Sulfolobus acidocaldarius*, ATCC 33909 (D83245) | 31.4% |

*Numerals in parentheses are access numbers to the GeneBank.

As shown in Table 4, the present non-reducing saccharide-forming enzyme in Example 2 showed a highest amino acid homology of 56.9% with the enzyme from *Rhizobium* sp. M-11 among conventional enzymes with optimum temperatures out of a medium temperature range. The data indicates that the present non-reducing saccharide-forming enzyme generally comprises an amino acid sequence with a homology of at least 57% with the amino acid sequence of SEQ ID NO:1. The comparison result on amino acid sequence revealed that the enzyme in Example 2 and the above-identified four types of conventional enzymes have common amino acid sequences of SEQ ID NOs:2 and 3. The enzyme in Example 2 has partial amino acid sequences of SEQ ID NOs:2 and 3 as they correspond to amino acids 84-89 and 277-282 in SEQ ID NO:1. The four types of enzymes used as references have the above partial amino acid sequences which are positioned at their corresponding parts. Based on the fact that any of the present enzyme in Example 2 and the enzymes as references have a common activity of forming non-reducing saccharides having a trehalose structure as an end unit from reducing partial starch hydrolysates, it was indicated that the partial amino acid sequences of SEQ ID NOs:2 and 3 correlated to the expression of such an enzyme activity. These results show that the present non-reducing saccharide-forming enzyme can be characterized in that it comprises the amino acid sequences of SEQ ID NOs:2 and 3, and has an optimum temperature in a medium temperature range.

EXAMPLE 3-3

Transformant Introduced with DNA

Based on the 5'- and 3'-termini of the nucleotide sequence of SEQ ID NO:7, an oligonucleotide of the nucleotide sequences of SEQ ID NOs:20 and 21 were chemically synthesized in a usual manner. As sense- and anti-sense-primers, 85 ng of each of the oligonucleotide and 100 ng of the recombinant DNA pGY2 in Example 3-2 as a template were mixed in a reaction tube, and the mixture was admixed with 1.25 units of "PYROBEST", a thermostable DNA polymerase specimen commercialized by Takara Shuzo Co., Ltd., Tokyo, Japan, together with 5 μl of a buffer affixed with the specimen and 4 μl of a dNTP mixture. The resulting mixture was brought up to a volume of 50 μl with sterilized distilled water to effect PCR. The temperature for PCR was controlled in such a manner that the mixture was treated with 25 cycles of successive incubations of 95° C. for one minute, 98° C. for 20 seconds, 70° C. for 30 seconds, and 72° C. for four minutes, and finally incubated at 72° C. for 10 min. A DNA as a PCR product was collected in a usual manner to obtain an about 2,300 bp DNA. The DNA thus obtained was admixed with "pKK223-3", a plasmid vector commercialized by Pharmacia LKB Biotechnology AB, Uppsala, Sweden, which had been previously cleaved with a restriction enzyme, EcoRI, and blunted by "DNA BLUNTING KIT" commercialized by Takara Shuzo Co., Ltd., Tokyo, Japan, and ligated by conventional ligation method. Thereafter, the ligated product was treated in a usual manner to obtain a recombinant DNA introduced with the above DNA consisting of bases of about 2,300 bp. Decoding of the recombinant DNA showed that it comprised a nucleotide sequence which two nucleotide sequences of 5'-ATG-3' and 5'-TGA-3' were respectively added to the 5'- and 3'-termini of the nucleo-tide sequence of SEQ ID NO:7. The DNA was named "pGY3". The structure of the recombinant DNA pGY3 was in FIG. 7.

The recombinant DNA pGY3 was in a usual manner introduced into an *Escherichia Coli* LE 392 strain, ATCC 33572, which had been competented in conventional manner, to obtain a transformant. Conventional alkali-SDS method was applied for the transformant to extract a DNA, and then the extracted DNA was confirmed to be pGY3 in a usual manner and named "GY3". Thus a transformant introduced with a DNA encoding the present non-reducing saccharide-forming enzyme.

EXAMPLE 3-4

Transformant Introduced with DNA

Based on a nucleotide sequence in the downstream of the 3'-terminus of a promotor in "pKK223-3", a plasmid vector commercialized by Pharmacia LKB Biotechnology AB, Uppsala, Sweden, oligonucleotide having the nucleotide sequences of SEQ ID NOs:22 and 23 were synthesized in conventional manner, and phosphorylated their 5'-termini using T4 polynucleotide kinase. The phosphorylated oligonucleotide were annealed, ligated with "pKK223-3", a plasmid vector commercialized by Pharmacia LKB Biotechnology AB, Uppsala, Sweden, which had been previously cleaved with restriction enzymes of EcoRI and PstI, by conventional ligation method. According to conventional method, the ligated product was introduced into an *Escherichia coli* strain which was then cultured and treated with alkali-SDS method to extract a DNA. The DNA thus obtained had a similar structure to a plasmid vector "pKK223-3", and had recognition sites by restriction enzymes of EcoRI, XbaI, SpeI, and PstI at the downstream of the promoter. The present inventors named the DNA a plasmid vector "pKK4".

Similarly as in Example 3-3, PCR was done except for using oligonucleotide with the nucleotide sequences of SEQ ID NOs:24 and 25, which had been chemically synthesized based on the 5'- and 3'-terminal partial nucleotide sequences of SEQ ID NO:7. A DNA as a PCR product was collected in a usual manner to obtain an about 2,300 bp DNA. The DNA thus obtained was cleaved with restriction enzymes, XbaI and SpeI, and the above plasmid vector pKK4, which had been cleaved with XbaI and SpeI, were ligated by conventional ligation method. Thereafter, the ligated product was treated in a usual manner to obtain a recombinant DNA with the nucleotide sequence of SEQ ID NO:7. The recombinant DNA was named "pKGY1".

Using overlap extension method, which two steps PCR were applied for and reported by Horthon, Robert M. in *Methods in Enzymology*, Vol. 217, pp. 270-279 (1993), a nucleotide sequence in the upper part of the 5'-terminus of SEQ ID NO:7 in the above DNA pKGY1 was modified. PCR as a first step PCR-A was done similarly as in Example 3-3 except for using, as sense- and anti-sense-primers, oligonucleotide of the nucleotide sequences of SEQ ID NOs:26 and 27, which had been chemically synthesized based on the nucleotide sequence of plasmid vector pKK4; and as a template the above recombinant DNA pKGY1. In parallel, PCR as a first step PCR-B was done similarly as in Example 3-3 except for using, as sense- and anti-sense-primers, oligonucleotide of the nucleotide sequences of SEQ ID NOs:28 and 29, which had been respectively chemically synthesized in a usual manner based on the nucleotide sequence of SEQ ID NO:7; and as a template the above recombinant DNA pKGY1. A DNA as a product of the first step PCR-A was collected in a usual manner to obtain an about 390 bp DNA. A DNA as a product in the first stp PCR-B was collected in conventional manner to obtain an about 930 bp DNA.

PCR, as a second step PCR-A, was done similarly as in Example 3-3 except for using as a template a DNA mixture, i.e., a product of the first PCR-A and the first step PCR-B; as a sense primer the oligonucleotide sequence of the nucleotide sequence of SEQ ID NO:26; and as an anti-sense primer the oligonucleotide of the nucleotide sequence of SEQ ID NO:30, which had been chemically synthesized in conventional manner based on the nucleotide sequence of SEQ ID NO:7. The DNA as a product in the PCR was collected in a usual manner to obtain an about 1,300 bp DNA.

The DNA as a product in the second PCR-A was cleaved with restriction enzymes of EcoRI and BsiWI, and the formed DNA consisting of bases of about 650 bp was collected in a usual manner. An about 6,300 bp DNA, which was formed after cleavage of the above recombinant DNA pKGY1 with restriction enzymes of EcoRI and BsiWI, was collected in conventional manner. These DNAs were ligated in a usual manner, and the ligated product was treated in conventional manner to obtain a recombinant DNA comprising an about 650 bp DNA derived from the second step PCR-A. Decoding of the DNA by conventional dideoxy method revealed that the obtained recombinant DNA comprised a nucleotide sequence which the nucleotide sequence of SEQ ID NO:8, a nucleotide sequence represented by 5'-ATG-3', and a nucleotide sequence represented by 5'-TGA-3' were cascaded in the order as indicated above from the 5'-terminus to the 3'-terminus. The recombinant DNA thus obtained was named "pGY4". The structure of pGY4 is substantially the same as the recombinant DNA pGY3 except for that pGY4 comprises the nucleotide sequence of SEQ ID NO:8.

The recombinant DNA pGY4 was introduced in conventional manner with "BMH71-18mutS", an *Escherichia coli* competent cell commercialized by Takara Shuzo Co., Ltd., Tokyo, Japan to obtain a transformant. The transformant was treated with alkali-SDS method to extract a DNA which was then identified with pGY4 in conventional manner. Thus a transformant introduced with a DNA encoding the present non-reducing saccharide-forming enzyme.

EXAMPLE 4

Preparation of Non-reducing Saccharide-Forming Enzyme

EXAMPLE 4-1

Preparation of Enzyme Using Microorganism of the Genus *Arthrobacter*

In accordance with the method in Example 2-1, *Arthrobacter* sp. S34, FERM BP-6450, was cultured by a fermenter for about 72 hours. After the cultivation, the resulting culture was concentrated with an SF-membrane to yield an about eight liters of a cell suspension. The cell suspension was treated with "MINI-LABO", a supper high-pressure cell disrupter commercialized by Dainippon Pharmaceutical Co., Ltd., Tokyo, to disrupt the cells. The resulting solution was centrifuged to obtain an about 8.5 l of a supernatant. When measured for non-reducing saccharide-forming activity in the supernatant, it showed an about 0.1 unit of the enzyme activity with respect to one milliliter of the culture. Ammonium sulfate was added to the supernatant to brought up to a saturation degree of about 0.7 to salt out, and the sediment was collected by centrifugation, dissolved in 10 mM phosphate buffer (pH 7.0), and dialyzed against a fresh preparation of the same buffer. Except for using an about 2 l of an ion-exchange resin, the resulting dialyzed inner solution was fed to ion-exchange column chromatography using "SEPABEADS FP-DA13 GEL", an anion exchanger commercialized by Mitsubishi Chemical Industries Ltd., Tokyo, Japan, as described in Example 2-2, to collect fractions with non-reducing saccharide-forming enzyme. The fractions were pooled, dialyzed against a fresh preparation of the same buffer but containing 1 M ammonium sulfate, and the resulting dialyzed inner solution was centrifuged to collect the formed supernatant. Except for using an about 300 ml gel, the supernatant was fed to hydrophobic column chromatography in accordance with the method described in Example 2-2 to collect fractions with non-reducing saccharide-forming enzyme. Then it was confirmed that the obtained enzyme had an optimum temperature over 40° C. but below 60° C., i.e., a temperature in a medium temperature range, and an acid pH range of less than 7.

Thus an about 2,600 units of the present non-reducing saccharide-forming enzyme was obtained.

EXAMPLE 4-2

Preparation of Enzyme Using Transformant

One hundred ml of an aqueous solution containing 16 g/l polypeptone, 10 g/l yeast extract, and 5 g/l sodium chloride was placed in a 500-ml Erlenmeyer flask, autoclaved at 121° C. for 15 min, cooled, adjusted aseptically to pH 7.0, and admixed aseptically with 10 mg of ampicillin in a sodium salt to obtain a liquid nutrient medium. The nutrient medium was inoculated with the transformant GY2 in Example 3-2, and incubated at 37° C. for about 20 hours under aeration-agitation conditions to obtain a seed culture. Seven liters of a medium having the same composition as used in the seed culture was prepared as in the case of the seed culture and placed in a 10-l fermenter, and inoculated with 70 ml of the seed culture, followed by the incubation for about 20 hours under aeration-agitation conditions. From the resultant culture cells were collected by centrifugation in a usual manner. The collected cells were suspended in phosphate buffer (pH 7.0), disrupted by the treatment of ultrasonication, and centrifuged to remove insoluble substances, followed by collecting a supernatant to obtain a cell extract. The extract was dialyzed against 10 mM phosphate buffer (pH 7.0). The resulting dialyzed inner solution was collected and confirmed that it exhibited a non-reducing saccharide-forming enzyme activity, had an optimum temperature in a medium temperature range, i.e., a temperature of over 40° C. but below 60° C., and had an optimum pH in an acid pH range, i.e., a pH of less than 7.

Thus the present non-reducing saccharide-forming enzyme was obtained. In the culture of this example, an about 0.2 unit/ml culture of the enzyme was produced.

As a control, "XL1-BLUE", an *Escherichia coli* strain commercialized by Stratagene Cloning Systems, California, USA, was cultured under the same conditions as above in a nutrient culture medium of the same composition as used in the above except that it contained no ampicillin. Similarly as above, a cell extract was obtained and dialyzed. No activity of non-reducing saccharide-forming enzyme was detected in the resulting dialyzed inner solution, meaning that the transformant GY2 is useful in producing the present non-reducing saccharide-forming enzyme.

EXAMPLE 4-3

Preparation of Enzyme Using Transformant

The transformant GY3 in Example 3-3 was cultured similarly as in Example 4-2 except for using a liquid nutrient culture medium consisting of one w/v % maltose, three w/v polypeptone, one w/v % "MEAST PIG", a product of Asahi Breweries, Ltd., Tokyo, Japan, 0.1 w/v % dipotassium hydrogen phosphate, 100 µg/ml ampicillin, and water. The resultant culture was treated with ultrasonication to disrupt cells, and the resulting mixture was centrifuged to remove insoluble substances. When assayed for non-reducing saccharide-forming enzyme activity in the resulting supernatant, the culture contained about 15 units/ml culture of the enzyme. In accordance with the method in Example 2-2, the enzyme in the supernatant was purified, confirming that the resulting purified specimen exhibited a non-reducing saccharide-forming enzyme activity, had an optimum temperature in a medium temperature range, i.e., a temperature of over 40° C. but below 60° C., and had an optimum pH in an acid pH range, i.e., a pH of less than 7. Thus the present non-reducing saccharide-forming enzyme was obtained.

EXAMPLE 4-4

Preparation of Enzyme Using Transformant

The transformant GY4 in Example 3-4 was cultured similarly as in Example 4-2 except for using a liquid nutrient culture medium consisting of two w/v % maltose, four w/v % peptone, one w/v % yeast extract, 0.1 w/v % sodium dihydrogen phosphate, 200 µg/ml ampicillin, and water. The resultant culture was treated with ultrasonication to disrupt cells, and the resulting mixture was centrifuged to remove insoluble substances. When assayed for non-reducing saccharide-forming enzyme activity in the resulting supernatant, the culture contained about 60 units/ml culture of the enzyme. In accordance with the method in Example 2-2, the enzyme in the supernatant was purified, confirming that the resulting purified specimen exhibited a non-reducing saccharide-forming enzyme activity, had an optimum temperature in a medium temperature range, i.e., a temperature of over 40° C. but below 60° C., and had an optimum pH in an acid pH range, i.e., a pH of less than 7. Thus the present non-reducing saccharide-forming enzyme was obtained.

EXAMPLE 5

Trehalose-releasing Enzyme

EXAMPLE 5-1

Production of Enzyme

According to the method in Example 2-1, *Arthrobacter* sp. S34, FERM BP-6450, was cultured by a fermenter. Then, in accordance with the method in Example 2-2, the resulting culture was sampled, followed by separating the sample into cells and a supernatant. From the cells a cell extract was obtained. When assayed for trehalose-releasing activity of the supernatant and the cell extract, the former scarcely exhibited the enzyme activity, while the latter exhibited an about 0.3 uni/ml culture of the enzyme.

EXAMPLE 5-2

Preparation of Enzyme

An about 80 l of a culture, prepared according to the method in Example 2-1, was centrifuged at 8,000 rpm for 30 min to obtain an about 800 g cells by wet weight. Two l of the wet cells was suspended in 10 mM phosphate buffer (pH 7.0) and treated with "MODEL UH-600", an ultrasonic homogenizer commercialized by MST Co., Tokyo, Japan. The resulting suspension was centrifuged at 10,000 rpm for 30 min, followed a collection of an about two liters of a supernatant. The supernatant was admixed with ammonium sulfate to bring to a saturation degree of 0.7, allowed to stand at 4° C. for 24 hours, and centrifuged at 10,000 rpm for 30 min to obtain a precipitate salted out with ammonium sulfate. The precipitate was dissolved in 10 mM phosphate buffer (pH 7.0), dialyzed against a fresh preparation of the same buffer for 48 hours, and centrifuged at 10,000 rpm for 30 min to remove insoluble substances. An about one liter of the resulting dialyzed inner solution was fed to ion-exchange column chromatography using an about 1.3 l of "SEPABEADS FP-DA13 GEL", an anion exchanger commercialized by Mitsubishi Chemical Industries Ltd., Tokyo, Japan. The elution step was carried out using a linear 10 mM phosphate buffer (pH 7.0) containing salt decreasing from 0 M to 0.6 M during the feeding. The eluate from the column was fractionated, and the fractions each were assayed for trehalose-releasing enzyme activity. As a result, the enzyme activity was remarkably found in fractions eluted with buffer having a salt concentration of about 0.2 M, followed by pooling the fractions.

Ammonium sulfate was added to the pooled solution to bring to a concentration of 1 M, and the mixture was allowed to stand at 4° C. for 12 hours, centrifuged at 10,000 rpm for 30 min to collect a supernatant. The supernatant was subjected to hydrophobic column chromatography using a column packed with "BUTYL TOYOPEARL 650M GEL", a hydrophobic gel commercialized by Tosoh Corporation, Tokyo, Japan. Prior to use, the gel volume was set to about 300 ml and equilibrated with 10 mM phosphate buffer (pH 7.0) containing 1 M ammonium sulfate. The elution step was carried out using a linear gradient aqueous solution of ammonium decreasing from 1 M to 0 M during the feeding. The eluate from the column was fractionated, and the fractions were respectively assayed for trehalose-releasing enzyme activity. As a result, the enzyme activity was remarkably found in fractions eluted with buffer having an ammonium concentration of about 0.5 M, followed by pooling the fractions.

The fractions were pooled, dialyzed against 10 mM phosphate buffer (pH 7.0), and the dialyzed inner solution was centrifuged at 10,000 rpm for 30 min. Then the resulting supernatant was collected and subjected to "DEAE-TOYOPEARL 650S GEL", an anion exchanger commercialized by Tosoh Corporation, Tokyo, Japan. The elution step was carried out using a linear gradient aqueous solution of salt increasing from 0 M to 0.2 M during the feeding. The eluate from the column was fractionated, and the fractions were respectively assayed for trehalose-releasing enzyme activity. As a result, the enzyme activity was remarkably found in fractions eluted with buffer having an ammonium concentration of about 0.15 M, followed by pooling the fractions. The pooled solution was subjected to gel filtration chromatography using about 380 ml of "ULTROGEL® AcA44 RESIN", a gel for gel filtration column chromatography commercialized by Sepracor/IBF s.a. Villeneuve la Garenne, France, followed collecting fractions with a remarkable activity of the enzyme. The content, specific activity, and yield of the enzyme in each step are in Table 5.

TABLE 5

| Step | Activity of Trehalose-releasing enzyme (unit) | Specific activity (mg/protein) | Yield (%) |
| --- | --- | --- | --- |
| Cell extract | 24,000 | — | 100 |
| Dialyzed inner solution after salting out with ammonium sulfate | 22,500 | 0.6 | 94 |

TABLE 5-continued

| Step | Activity of Trehalose-releasing enzyme (unit) | Specific activity (mg/protein) | Yield (%) |
| --- | --- | --- | --- |
| Eluate from SEPABEADS column | 15,600 | 2.0 | 65 |
| Eluate from hydrophobic column | 6,400 | 25.3 | 27 |
| Eluate from TOYOPEARL column | 4,000 | 131 | 17 |
| Eluate after gel filtration | 246 | 713 | 1.0 |

When electrophoresed in 7.5 w/v % polyacrylamide gel in conventional manner, the solution eluted and collected from the above gel filtration chromatography gave a single protein band. The data indicates that the eluate from gel filtration chromatography obtained in the above was a purified trehalose-releasing enzyme purified up to an electrophoretically homogeneous level.

EXAMPLE 5-3

Property of Enzyme

EXAMPLE 5-3(a)

Action

Any one of saccharides consisting of α-glucosyltrehalose, α-maltosyltrehalose, α-maltotriosyltrehalose, α-maltotetraosyltrehalose, and α-maltopentaosyltrehalose as non-reducing saccharides having a trehalose structure obtained by the method in the later described Example 8-3; and maltotriose, maltotetraose, maltopentaose, maltohexaose, and maltoheptaose as reducing saccharides was dissolved in water into a 2 w/v % solution as an aqueous substrate solution for substrate. Each aqueous substrate solution was admixed with two units/g substrate, d.s.b., of a purified specimen of trehalose-releasing enzyme obtained by the method in Example 5-2, and enzymatically reacted at 50° C. and pH 6.0 for 48 hours. In accordance with the method in Example 2-3(a), the reaction product was analyzed on HPLC after desalting to calculate the saccharide composition of the reaction products each. The results are in Table 6. In Table 6, α-glucosyltrehalose, α-maltosyltrehalose, α-maltotriosyltrehalose, α-maltotetraosyltrehalose, and α-maltopentaosyltrehalose were respectively expressed as glucosyltrehalose, maltosyltrehalose, maltotriosyltrehalose, maltotetraosyltrehalose, and maltopentaosyltrehalose.

TABLE 6

| Substrate | Reaction product | Elution time (min) | Composition (%) |
| --- | --- | --- | --- |
| Glucosyltrehalose | Trehalose | 48.5 | 16.8 |
|  | Glucose | 57.2 | 8.2 |
|  | Glucosyltrehalose | 43.3 | 75.0 |
| Maltosyltrehalose | Trehalose | 48.5 | 44.1 |
|  | Maltose | 50.8 | 44.4 |
|  | Maltosyltrehalose | 38.9 | 11.5 |
| Maltotriosyltrehalose | Trehalose | 48.5 | 40.5 |
|  | Maltotriose | 46.2 | 59.0 |
|  | Maltotriosyltrehalose | 35.4 | 0.5 |
| Maltotetraosyltrehalose | Trehalose | 48.5 | 35.0 |
|  | Maltotetraose | 42.1 | 64.2 |
|  | Maltotetraosyltrehalose | 32.7 | 0.3 |

TABLE 6-continued

| Substrate | Reaction product | Elution time (min) | Composition (%) |
|---|---|---|---|
| Maltopentaosyltrehalose | Trehalose | 48.5 | 29.5 |
|  | Maltopentaose | 38.2 | 70.2 |
|  | Maltopentaosyltrehalose | 30.2 | 0.3 |
| Maltotriose | Maltotriose | 46.2 | 100.0 |
| Maltotetraose | Maltotetraose | 42.1 | 100.0 |
| Maltopentaose | Maltopentaose | 38.2 | 100.0 |
| Maltohexaose | Maltohexaose | 35.2 | 100.0 |
| Maltoheptaose | Maltoheptaose | 32.6 | 100.0 |

As evident from the results in Table 6, the trehalose-releasing enzyme, obtained by the method in Example 5-2, specifically hydrolyzed a non-reducing saccharide, which has a trehalose structure as an end unit and a glucose polymerization degree of at least three, to release trehalose from the rest of the non-reducing saccharide to form trehalose and a reducing saccharide having a glucose polymerization degree of one or more. While the enzyme did not act on maltooligosaccharides such as maltotriose and lower saccharides.

EXAMPLE 5-3(b)

Molecular Weight

A purified specimen of a trehalose-releasing enzyme, obtained by the method in Example 5-2, was subjected along with molecular markers commercialized by Japan Bio-Rad Laboratories, Tokyo, Japan, to conventional SDS-PAGE using 10 w/v % polyacrylamide gel. After electrophoresis, the position of the specimen electrophoresed on the gel was compared with those of the markers, revealing that the specimen had a molecular weight of about 62,000±5,000 daltons.

EXAMPLE 5-3(c)

Isoelectric Point

A purified specimen of a trehalose-releasing enzyme, obtained by the method in Example 5-2, was in a usual manner subjected to isoelectrophoresis using a polyacrylamide gel containing 2 w/v % "AMPHOLINE", an ampholyte commercialized by Pharmacia LKB Biotechnology AB, Uppsala, Sweden. Measurement of pH of the gel after electrophoresis, it had an isoelectric point of about 4.7±0.5.

EXAMPLE 5-3(d)

Optimum Temperature and pH

A purified specimen of a trehalose-releasing enzyme, obtained by the method in Example 5-2, was examined on the influence of the temperature and pH on the enzyme activity. The influence of temperature was examined according to the assay for enzyme activity except for reacting the enzyme at different temperatures. The influence of pH was examined according to the assay for enzyme activity except for reacting the enzyme at different pHs using appropriate 20 mM buffers. In each procedure, relative values (%) of the increased level of reducing power found in each system were calculated and regarded as relative enzyme activity (%). The results of the influence of temperature and pH are respectively in FIGS. 8 and 9. The cross axles in FIGS. 8 and 9 show reaction temperatures and pHs for the enzyme, respectively. As shown in FIG. 8, the optimum temperature of the enzyme was about 50 to about 55° C. when incubated at pH 6.0 for 30 min, while the optimum pH of the enzyme was a pH of about 6.0 when incubated at 50° C. for 30 min.

EXAMPLE 5-3(e)

Stability on Temperature and pH

A purified specimen of a trehalose-releasing enzyme, obtained by the method in Example 5-2, was examined on the stability of temperature and pH. The stability of temperature was examined by diluting the specimen with 20 mM phosphate buffer (pH 7.0), incubating the dilutions at different temperatures for 60 min, cooling the resulting dilutions, and assaying the enzyme activity remained in the dilutions. The pH stability was studied by diluting the specimen with 50 mM buffers (pH 7.0) with different pHs, incubating the dilutions at 4° C. for 24 hours, adjusted to pH 6, and assaying the enzyme activity remained in the dilutions. The results of the stability of temperature and pH are respectively in FIGS. 10 and 11. The cross axles in FIGS. 10 and 11 show temperatures and pHs at which the enzyme was kept, respectively. As shown in FIG. 10, the enzyme was stable up to about 50° C., while the enzyme was stable at pHs in the range of about 4.5 to about 10.0.

The results described hereinbefore indicate that the trehalose-releasing enzyme, obtained by the method in Example 5-2, is the present enzyme which has an optimum temperature in a medium temperature range.

EXAMPLE 5-4

Partial Amino Acid Sequence

A portion of a purified specimen of a trehalose-releasing enzyme, obtained by the method in Example 5-2, was dialyzed against distilled water and prepared into a sample containing about 80 ng protein for the N-terminal amino acid analysis. Using "PROTEIN SEQUENCER MODEL 473A", a protein sequencer commercialized by Applied Biosystems, Inc., Foster City, USA, the N-terminal amino acid sequence was analyzed up to 20 amino acid residues from the N-terminus. The revealed N-terminal amino acid sequence was the partial amino acid sequence of SEQ ID NO:14.

A portion of a purified specimen of a trehalose-releasing enzyme, obtained by the method in Example 5-2, was dialyzed against 10 mM Tris-HCl buffer (pH 9.0) and in a usual manner concentrated to give a concentration of about one milligram per milliliter using "ULTRACENT-30", an ultrafiltration membrane commercialized by Tosoh Corporation, Tokyo, Japan. To 0.2 ml of the concentrate was added 10 μg of a lysyl endopeptidase reagent commercialized by Wako Pure Chemical Industries, Ltd., Tokyo, Japan, and the mixture was incubated at 30° C. for 22 hours to digest the enzyme and to form peptides. The reaction mixture was subjected to reverse-phase HPLC using a column of "NOVA-PAK C18 COLUMN", 4.5 mm in diameter and 150 mm in length, commercialized by Waters Chromatography Div., Millipore Corp., Milford, Mass., USA, to separate the peptides under ambient temperature. The elution step was carried out using a linear gradient of a 0.1 v/v % aqueous trifluoroacetic acid solution containing acetonitrile increasing from 24 v/v % to 48 v/v % for 60 min during the feeding at a flow rate of 0.9 ml/min. Peptides eluate from the column was monitored by measuring at a wavelength of 210 nm. Two peptides, named "RT18" with a retention time of about 18 min and "RT33" with a retention time of about 33 min and well separated from others, were collected, dried in vacuo, and dissolved respectively in a 50 v/v % aqueous acetonitrile solution containing 200 μl of 0.1 v/v % trifluoroacetic acid. The peptide solutions were subjected to a protein sequencer to analyze up to 20 amino acid residues from the N-terminus of each peptide. The amino acid sequences of SEQ ID NOs:15 and 16 from the peptides RT18 and RT33, respectively.

EXAMPLE 6

DNA Encoding Trehalose-releasing Enzyme

EXAMPLE 6-1

Construction and Screening of Gene Library

According to Example 3-1, a gene library of *Arthrobacter* sp. S34, FERM BP-6450 was constructed, and then subjected to screening by applying colony hybridization method under the conditions as used in Example 3-1 except for using as a probe an oligonucleotide, having a nucleotide sequence encoding the present trehalose-releasing enzyme, prepared by the following procedures; The probe was in a usual manner prepared by labelling with an isotope of [γ-$^{32}$P] ATP and T4 polynucleotide kinase the oligonucleotide having the nucleotide sequence of SEQ ID NO:31, which had been chemically synthesized based on an amino acid sequence consisting of amino acids 12-20 of SEQ ID NO:15 revealed in Example 5-4. A transformant which strongly hybridized with the prove was selected.

According to the method in Example 3-2, a recombinant DNA was extracted from the transformant and analyzed on conventional Southern blot technique using the above prove. A restriction map made based on the analytical data was coincided with that of the recombinant DNA pGY1 obtained in Examples 3-1 and 3-2. As shown in FIG. 5, it was revealed that the present recombinant DNA in this example contained a nucleotide sequence, which encoded the present trehalose-releasing enzyme as indicated with an oblique arrow, within a region consisting of bases of about 2,200 bp positioned between recognition sites by restriction enzymes, PstI and KpnI. Using the recombinant DNA pGY1, it was proceeded the decoding of the nucleotide sequence of DNA encoding the present trehalose-releasing enzyme.

EXAMPLE 6-2

Decoding of Nucleotide Sequence

The recombinant DNA pGY1, obtained by the method in Example 3-2, was in conventional manner completely digested with a restriction enzyme, PstI. The DNA fragment of about 3,300 bp formed in the resulting mixture was removed on conventional agarose electrophoresis, and the formed DNA fragment of about 5,200 bp was collected. The DNA fragment was in a usual manner subjected to ligation reaction, and the ligated product was used to transform "XL1-BLUE", an *Escherichia coli* strain commercialized by Stratagene Cloning Systems, California, USA. From the resultant transformant, a recombinant DNA was extracted by conventional method. The recombinant DNA was confirmed to have a region consisting of bases of about 2,200 bp comprising a nucleotide sequence encoding the present trehalose-releasing enzyme, and named "pGZ2". A transformant intr254oduce with pGZ2 was named a recombinant DNA pGZ2.

Analysis of Conventional dideoxy method for the nucleotide sequence of the recombinant DNA pGZ2 revealed that it contained a nucleotide sequence consisting of 2,218 bp bases as shown in SEQ ID NO:32 derived from *Arthrobacter* sp. S34, FERM BP-6450. The nucleotide sequence could encode the amino acid sequence in SEQ ID NO:32. The amino acid sequence was compared with those of SEQ ID NOs:14 to 16 as partial amino acid sequences of the present trehalose-releasing enzyme confirmed in Example 5-4. As a result, the amino acid sequences of SEQ ID NOs:14, 15 and 16 were respectively coincided with amino acids 1-20, 298-317, and 31-50 of the amino acid sequence in SEQ ID NO:32. The data indicates that the trehalose-releasing enzyme in Example 5 comprises the amino acid sequence in SEQ ID NO:32 or the one of SEQ ID NO:9, and that the enzyme from *Arthrobacter* sp. S34, FERM BP-6450, is encoded by bases 477-2,201 in SEQ ID NO:32 or the nucleotide sequence of SEQ ID NO:17. FIG. 12 shows the structure of the aforesaid recombinant DNA pGZ2.

The above amino acid sequence of the present trehalose-releasing enzyme, obtained by the method in Example 5, and other conventional ones of enzymes having an activity of trehalose-releasing enzyme were compared with each other in accordance with the method in Example 3-2 to determine their homology (%). As conventional enzymes, those derived from *Arthrobacter* sp. Q36 disclosed in Japanese Patent Kokai No. 298,880/95; *Rhizoblum* sp. M-11, disclosed in Japanese Patent Kokai No. 298,880/95; *Sulfolobus acidocaldarius*, ATCC 33909; and *Sulfolobus solfataricus* KM1 disclosed in Sai-Kohyo No. WO95/34642. All of these enzymes have optimum temperatures out of a medium temperature range. The amino acid sequences of these enzymes are available from the GenBank, a DNA database produced by the National Institutes of Health (NIH), USA, under the accession numbers of D63343, D64130, D78001, and D83245. The information of their homology are in Table 7.

TABLE 7

| Origin of enzyme for amino acid sequence(*) comparison | Homology on amino acid sequence |
|---|---|
| *Arthrobacter* sp. Q36 (D63343) | 59.9% |
| *Rhizobium* sp. M-11 (D78001) | 59.1% |
| *Sulfolobus solfataricus* KM1 (D64130) | 37.7% |
| *Sulfolobus acidocaldarius*, ATCC 33909 (D83245) | 36.0% |

*Numerals in parentheses are access numbers to the GeneBank.

As shown in Table 7, the present trehalose-releasing enzyme in Example 5 showed a highest amino acid homology of 59.9% with the enzyme from Arthrobacter sp. Q36 among conventional enzymes with optimum temperatures out of a medium temperature range. The data indicates that the present trehalose-releasing enzyme generally comprises an amino acid sequence with a homology of at least 60% with the amino acid sequence of SEQ ID NO:9. The comparison result on amino acid sequence revealed that the enzyme in Example 5 and the above-identified four types of conventional enzymes have common amino acid sequences of SEQ ID NOs:10 and 13. The enzyme in Example 5 has partial amino acid sequences of SEQ ID NOs:10 to 13 as found in amino acids 148-153, 185-190, 248-254 and 285-291 in SEQ ID NO:9. The four types of enzymes used as references have the above partial amino acid sequences which are positioned at their corresponding parts. Based on the fact that any of the present enzyme in Example 5 and the enzymes as references have commonly an activity of specifically hydrolysing a non-reducing saccharide, which has a trehalose structure as an end unit and a glucose polymerization degree of at least three, to release trehalose from the rest of the non-reducing saccharide, it was indicated that the partial amino acid sequences of SEQ ID NOs:10 to 13 correlated to the expression of such an enzyme activity. These results show that the present trehalose-releasing enzyme can be characterized in that it comprises the amino acid sequences of SEQ ID NOs:10 to 13 and has an optimum temperature in a medium temperature range.

EXAMPLE 6-3

Transformant Introduced with DNA

Based on the 5'- and 3'-terminal nucleotide sequences of SEQ ID NO:17, oligonucleotides of the bases of SEQ ID NOs:33 and 34 were chemically synthesized in a usual manner. As sense-and anti-sense-primers, 85 ng of each of the oligonucleotides and 100 ng of the recombinant DNA pGZ2 in Example 6-2 as a template were mixed in a reaction tube while adding another reagents in accordance with Example 3-3. The temperature for PCR was controlled in such a manner that the mixture was treated with 25 cycles of successive incubations of 95° C. for one minute, 98° C. for 20 seconds, 70° C. for 30 seconds, and 72° C. for four minutes, and finally incubated at 72° C. for 10 min. A DNA as a PCR product was collected in a usual manner to obtain an about 1,700 bp DNA. The DNA thus obtained was admixed with "pKK233-3", a plasmid vector commercialized by Pharmacia LKB Biotechnology AB, Uppsala, Sweden, which had been previously cleaved with a restriction enzyme, EcoRI, and blunted by "DNA BLUNTING KIT" commercialized by Takara Shuzo Co., Ltd., Tokyo, Japan, and ligated by conventional ligation method. Thereafter, the ligated product was treated in a usual manner to obtain a recombinant DNA introduced with the above DNA consisting of bases of about 1,700 bp. Decoding of the recombinant DNA by conventional dideoxy method showed that it comprised a nucleotide sequence which a nucleotide sequence of 5'-TGA-3' was added to 3'-terminus of the nucleotide sequence of SEQ ID NO:17. The DNA was named "pGZ3". The structure of the recombinant DNA pGZ3 was in FIG. 13.

The recombinant pGZ3 was in a usual manner introduced into an *Escherichia coli* LE 392 strain, ATCC 33572, which had been competented in conventional manner, to obtain a transformant. Conventional alkali-SDS method was applied for the transformant to extract a DNA and named "GZ3" by identifying transformant as pGZ3. Thus a transformant, introduced with the present trehalose-releasing enzyme, was obtained.

EXAMPLE 6-4

Transformant Introduced with DNA

PCR was done similarly as in Example 6-3 except for using, as sense- and anti-sense-primers, oligonucleotide having nucleotide sequences of SEQ ID NOs:35 and 36, respectively, which had been chemically synthesized based on the 5'- and 3'-terminal nucleotide sequences of SEQ ID NO:17. A DNA as a PCR product was collected in a usual manner to obtain an about 1,700 bp DNA. The DNA thus obtained was cleaved with restriction enzymes, XbaI and SpeI, and "pKK4", a plasmid vector obtained by the method in Example 3-4, which had been previously cleaved with restriction enzyme, XbaI and SpeI, were ligated in a usual manner. Thereafter, the ligated product was treated in a usual manner to obtain a recombinant DNA comprising the nucleotide sequence of SEQ ID NO:17. The recombinant DNA thus obtained was named "pKGZ1".

A nucleotide sequence in the upper part of the 5'-terminus of SEQ ID NO:17 contained in the recombinant DNA pKGZ1 was modified similarly as in Example 3-4; PCR as a first PCR-C was carried out similarly as in Example 3-3 except for using the above recombinant DNA pKGZ1 as a template and oligonucleotides of SEQ ID NOs:26 and 37, as sense- and anti-sense-primers, which had been chemically synthesized in a usual manner based on the nucleotide sequence of the plasmid vector pKK4. In parallel, PCR as a first PCR-D was carried out similarly as in Example 3-3 except for using the above recombinant DNA pKGZ1 as a template and oligonucleotides of SEQ ID NOs:38 and 39, as sense- and anti-sense-primers, which had been chemically synthesized in a usual manner based on the nucleotide sequences of SEQ ID NOs:38 and 39. A DNA as a PCR-C product was collected in a usual manner to obtain an about 390 bp DNA, while another DNA as a PCR-D product was collected similarly as above to obtain an about 590 bp DNA.

PCR as a second PCR-B was carried out similarly as in Example 3-3 except for using the DNA mixture obtained as products in the first PCR-C and first PCR-D, an oligonucleotide of SEQ ID NO:26 used in the first PCP-C as a sense primer, and an oligonucleotide of SEQ ID NO:39 used in the first PCR-D as an anti-sense primer. A DNA as a PCR product was collected in a usual manner to obtain an about 950 bp DNA.

The DNA as a second PCR-B product was cleaved with a restriction enzyme, EcoRI, and the formed about 270 bp DNA was collected in conventional manner. The recombinant DNA pKGZ1 was cleaved with a restriction enzyme, EcoRI, and the formed about 5,100 bp DNA was collected similarly as above. These DNAs were ligated as usual and treated in a usual manner to obtain a recombinant DNA comprising about 270 bp DNA from the second PCR-B product. Decoding of the recombinant DNA by conventional dideoxy method revealed that it contained the nucleotide sequence of SEQ ID NO:8, one of SEQ ID NO:17, and one represented by 5'-TGA-3' in the order as indicated from the 5'- to 3'-termini. The recombinant DNA thus obtained was named "pGZ4". The recombinant DNA pGZ4 had substantially the same structure as the recombinant DNA pGZ3 obtained in Example 6-3 except that it had the nucleotide sequence of SEQ ID NO:8.

The recombinant DNA pGZ4 was introduced into "BMH71-18mutS", an *Escherichia coli* competent cell commercialized by Takara Shuzo Co., Ltd., Tokyo, Japan, to obtain a transformant. Using conventional alkali-SDS method, a DNA was extracted from the transformant and confirmed to be pGZ4 according to conventional manner. It was named "GZ4". Thus a transformant introduced with a DNA encoding the present trehalose-releasing enzyme.

EXAMPLE 7

Preparation of Trehalose-Releasing Enzyme

EXAMPLE 7-1

Preparation of Enzyme Using Microorganisms of the Genus *Arthrobacter*

A seed culture of *Arthrobacter* sp. S34, FERM BP-6450, was inoculated to a nutrient culture medium and incubated by a fermenter for about 72 hours in accordance with the method in Example 2-1. After the incubation, the resultant culture was filtered and concentrated with an SF-membrane to obtain an about eight liters of cell suspension which was then treated with "MINI-LABO", a super high-pressure cell disrupter commercialized by Dainippon Pharmaceutical Co., Ltd., Tokyo, Japan, to disrupt cells. The cell disruptant was centrifuged to collect and obtain an about 8.5 l supernatant as a cell extract. Determination of the cell extract for trehalose-releasing enzyme activity revealed that the culture contained about 0.3 unit/ml culture of the enzyme activity. To the cell extract was added ammonium sulfate to give a saturation degree of 0.7 to effect salting out, and then centrifuged to obtain the precipitate. The precipitate was dissolved in 10 mM phosphate buffer (pH 7.0), and dialyzed against a fresh preparation of the same buffer. The dialyzed inner solution was subjected to ion-exchange chromatography using "SEPABEADS FP-DA13 GEL" commercialized by Mitsubishi Chemical Co., Ltd., Tokyo, Japan, in accordance with the method in Example 5-2 except that the resin volume used of the ion exchanger was about two liters, followed by collecting fractions having an trehalose-releasing enzyme activity. The fractions were pooled and dialyzed against a fresh preparation of the same buffer but containing 1 M ammonium sulfate, and then the dialyzed solution was centrifuged to obtain the formed supernatant. The supernatant was subjected to a hydrophobic column chromatography using "BUTYL TOYOPEARL 650M GEL", a hydrophobic gel commercialized by Tosoh Co., Ltd., Tokyo, Japan, in accordance with the method in Example 5-2 except that an about 350 ml of the gel was used, and then fractions with a trehalose-releasing enzyme activity were collected. The enzyme collected was confirmed to have an optimum temperature in a medium temperature range, i.e., temperatures over 45° C. but below 60° C. and an optimum pH in an acid pH range, i.e., a pH of less than 7.

Thus an about 6,400 units of the present trehalose-releasing enzyme was obtained.

EXAMPLE 7-2

Preparation of Enzyme Using Microorganism of the Genus *Arthrobacter*

A seed culture of *Arthrobacter* sp. S34, FERM BP-6450, was inoculated to a nutrient culture medium in accordance with the method in Example 7-1. To one l of the resulting culture was added 100 mg "OVALBUMIN LYSOZYME", a lysozyme preparation, commercialized by Nagase Biochemicals, Ltd., Kyoto, Japan. Then aeration was suspended, and cells were disrupted by keeping the culture for 24 hours under the same temperature and stirring conditions as used in the culture. The cell disruptant was subjected to a continuous centrifuge at 10,000 rpm, followed by collecting a supernatant as a cell extract. In accordance with the method in Example 7-1, the cell extract was treated with salting out, and the sediment was dialyzed. The resulting dialyzed inner solution was subjected to ion-exchange chromatography using "SEPABEADS FP-DA13 GEL", a product of Mitsubishi Chemical Co., Ltd., Tokyo, Japan, in accordance with the method in Example 7-1 to collect fractions with a trehalose-releasing enzyme activity. The pooled fractions contained about 16,500 units of the present trehalose-releasing enzyme and about 5,500 units the present non-reducing saccharide-forming enzyme. Thus an enzyme preparation containing the present two types of enzymes was obtained.

EXAMPLE 7-3

Production of Enzyme Using Transformant

In a 500-ml Erlenmeyer flask were placed a 100 ml aqueous solution containing 16 g/l polypeptone, 10 g/l yeast extract, and 5 g/l sodium chloride, and the flask was autoclaved at 121° C. for 15 min, cooled, aseptically adjusted to pH 7.0, and aseptically admixed with 10 mg ampicillin in a sodium salt to obtained a nutrient culture medium. The transformant "GZ2" obtained in Example 6-2 was inoculated into the liquid medium, followed by the incubation at 37° C. for about 20 hours under aeration-agitation conditions to obtain a seed culture. Seven liters of a fresh preparation of the same medium as used in the seed culture were similarly prepared and placed in a 10-l fermenter, inoculated with 70 ml of the seed culture, and cultures for about 20 hours under aeration-agitation conditions. Cells were collected by centrifuging the resulting culture in usual mariner. The collected cells were suspended in 10 mM phosphate buffer (pH 7.0) and ultrasonicated to disrupt the cells. The resulting mixture was centrifuged to remove insoluble substances, followed by collecting a supernatant as a cell extract. The cell extract was dialyzed against 10 mM phosphate buffer (pH 7.0). The dialyzed inner solution was collected and confirmed to have an optimum temperature in a medium temperature range, i.e., temperatures over 45° C. but below 60° C. and an optimum pH in an acid pH range, i.e., a pH of less than 7.

Thus the present trehalose-releasing enzyme was obtained. In this Example, an about 0.5 unit/ml culture of the trehalose-releasing enzyme was obtained.

As a control, "XL1-Blue", an *Escherichia coli* strain commercialized by Stratagene Cloning Systems, California, USA, was cultured under the same culture conditions as used in the above in a fresh preparation of the same culture medium as above but free of ampicillin, followed by collecting and dialyzing a cell extract similarly as above. No trehalose-releasing enzyme activity was observed, meaning that the transformant GZ2 can be advantageously used in producing the present trehalose-releasing enzyme.

EXAMPLE 7-4

Production of Enzyme Using Transformant

The transformant GZ3 in Example 6-3 was cultured similarly as in Example 7-3 except for using a liquid nutrient culture medium (pH 7.0) consisting of one w/v % maltose, three w/v % polypeptone, one w/v % "MEAST PIG" commercialized by Asahi Breweries, Ltd., Tokyo, Japan, 0.1 w/v % dipotassium hydrogen phosphate, 100 µg/ml ampicillin, and water. The resulting culture was treated with ultrasonication to disrupt cells, and the mixture was centrifuged to remove insoluble substances. Measurement of the trehalose-releasing enzyme activity in the resulting supernatant revealed that it contained about 70 units/ml culture of the enzyme. In accordance with the method in Example 5-2, the supernatant was purified and confirmed that the purified specimen had an optimum temperature in a medium temperature range, i.e., temperatures over 45° C. but below 60° C. and an optimum pH in an acid pH range, i.e., a pH of less than 7. Thus the present trehalose-releasing enzyme was obtained.

EXAMPLE 7-5

Production of Enzyme Using Transformant

The transformant GZ4 in Example 6-4 was cultured similarly as in Example 4-4. The resulting culture was treated with ultrasonication to disrupt cells, and the mixture was centrifuged to remove insoluble substances. Measurement of the trehalose-releasing enzyme activity in the resulting supernatant revealed that it contained about 250 units/ml culture of the enzyme. In accordance with the method in Example 5-2, the supernatant was purified and confirmed that the purified specimen had an optimum temperature in a medium temperature range, i.e., temperatures over 45° C. but below 60° C. and an optimum pH in an acid pH range, i.e., a pH of less than 7. Thus the present trehalose-releasing enzyme was obtained.

EXAMPLE 8

Saccharide Production

EXAMPLE 8-1

Production of Non-reducing Saccharide Syrup

A 6 w/w % potato starch suspension was gelatinized by heating, adjusted to pH 4.5 and 50° C., admixed with 2,500 units/g starch, d.s.b., and enzymatically reacted for 20 hours. The reaction mixture was adjusted to pH 6.5, autoclaved at 120° C. for 10 min, cooled to 40° C., admixed with 150 units/g starch, d.s.b., of "TERMAMYL 60L", an α-amylase specimen commercialized by Novo Nordisk Industri A/S, Copenhagen, Denmark, and subjected to an enzymatic reaction for 20 hours while keeping at the temperature. The reaction mixture was autoclaved at 120° C. for 20 min, cooled to 53° C., adjusted to pH 5.7, admixed with one unit per gram starch, d.s.b., of a non-reducing saccharide-forming enzyme obtained in Example 4-1, and subjected to an enzymatic reaction for 96 hours. The reaction mixture thus obtained was heated at 97° C. for 30 min to inactivate the remaining enzyme, cooled, filtered, purified in a usual manner by decoloration with an activated charcoal and desalting with ion exchangers, and concentrated to obtain an about 70 w/w % syrup in a yield of about 90% to the material starch, d.s.b.

The product, which has a low DE of 24 and contains α-glucosyltrehalose, α-maltosyltrehalose, α-maltotriosyltrehalose, α-maltotetraosyltrehalose, and α-maltopentaosyltrehalose in respective amount of 11.5, 5.7, 29.5, 3.5, and 2.8%, d.s.b., has a mild and high-quality sweetness, and a satisfactory viscosity and moisture-retaining ability. It can be arbitrarily used as a sweetener, taste-improving agent, quality-improving agent, stabilizer, filler, adjuvant or excipient in compositions in general such as foods, cosmetics, and pharmaceuticals.

EXAMPLE 8-2

Production of Syrup Containing Non-reducing Saccharide

To a 33 w/w % corn starch suspension was added calcium carbonate to give a final concentration of 0.1 w/w %, and then the mixture was adjusted to pH 6.5, admixed with 0.2 w/w % per starch, d.s.b., of "TERMAMYL 60L", a liquefying α-amylase specimen commercialized by Novo Nordisk Industri A/S, Copenhagen, Denmark, and enzymatically reacted at 95° C. for 15 min to liquefy the starch. The liquefied starch was autoclaved at 120° C. for 10 min, cooled to 53° C., admixed with one unit/g starch, d.s.b., of a maltotetraose-forming enzyme from a *Pseudomonas stutzeri* strain commercialized by Hayashibara Biochemical Laboratories Inc., Okayama, Japan, and two units/g starch, d.s.b., of a non-reducing saccharide-forming enzyme obtained by the method in Example 4-2, and enzymatically reacted for 48 hours. The reaction mixture was admixed with 15 units of "α-AMYLASE 2A", an α-amylase specimen commercialized by Ueda Chemical Co., Ltd., Osaka, Japan, and then incubated at 65° C. for two hours, autoclaved at 120° C. for 10 min, and cooled. The resulting mixture was filtered, and in a usual manner purified by treatments of coloration using an activated charcoal and of desalting using ion exchangers, and concentrated into an about 70 w/w % syrup, d.s.b., in a yield of about 90% with respect to the material starch, d.s.b.

The product, which has a low DE of 18.5 and contains α-glucosyltrehalose, α-maltosyltrehalose, α-maltotriosyltrehalose, α-maltotetraosyltrehalose, and α-maltopentaosyltrehalose in respective amount of 9.3, 30.1, 0.9, 0.8, and 0.5%, d.s.b., has a mild and high-quality sweetness, and a satisfactory viscosity and moisture-retaining ability. It can be arbitrarily used as a sweetener, taste-improving agent, quality-improving agent, stabilizer, filler, adjuvant or excipient in compositions in general such as foods, cosmetics, and pharmaceuticals.

EXAMPLE 8-3

Production of Non-reducing Saccharide

A 20 w/w % aqueous solution of any of reducing partial starch hydrolyzates of maltotriose, maltotetraose, maltopentaose, maltohexaose, and maltoheptaose, which are all produced by Hayashibara Biochemical Laboratories Inc., Okayama, Japan, admixed with two units/g reducing partial starch hydrolyzate of a purified specimen of non-reducing saccharide-forming enzyme obtained by the method in Example 2-2, and subjected to an enzymatic reaction at 50° C. and pH 6.0 for 48 hours. From each of the above-identified reducing partial starch hydrolyzates were respectively formed α-glucosyltrehalose, α-maltosyltrehalose, α-maltotriosyltrehalose, α-maltotetraosyltrehalose, and α-maltopentaosyltrehalose as reducing saccharides. Saccharides in each reaction mixture were in conventional manner fractionated by the following successive treatments: Inactivation of the remaining enzyme by heating, filtration, decoloration, desalting, concentration, and column chromatography using "XT-1016 ($Na^+$-form)", an alkali-metal strong-acid cation exchange resin with a polymerization degree of 4%, commercialized by Tokyo Organic Chemical Industries, Ltd., Tokyo, Japan. The conditions used in the column chromatography were as follows: The inner column temperature was set to 55° C., the load volume of a saccharide solution to the resin was about 5 v/v %, and the flow rate of water heated to 55° C. as a moving bed was set to SV (space velocity) 0.13. An eluate from each column, which contained at least 95 w/w % of any of the above-identified non-reducing saccharides, d.s.b., with respect to saccharide composition, was collected. To each collected eluate was added sodium hydroxide to give a concentration of 0.1 N, and the mixture was heated at 100° C. for two hours to decompose the remaining reducing saccharides. The reaction mixtures thus obtained were respectively decolored with an activated charcoal, desalted with ion exchangers in H— and OH-form, concentrated, dried in vacuo, and pulverized into powdery α-glucosyltrehalose, α-maltosyltrehalose, α-maltotriosyltrehalose, α-maltotetraosyltrehalose, and α-maltopentaosyltrehalose with a purity of at least 99.0 w/w %, d.s.b.

The products, containing highly-purified non-reducing saccharides and having a more lower DE, can be arbitrarily used as a taste-improving agent, quality-improving agent, stabilizer, filler, adjuvant or excipient in compositions in general such as foods, cosmetics, and pharmaceuticals.

EXAMPLE 8-4

Production of Crystalline Powder Containing Non-reducing Saccharide

An aqueous 20 w/w % solution of maltopentaose commercialized by Hayashibara Biochemical Laboratories Inc., Okayama, Japan, was prepared, admixed with two units/g maltopentaose, d.s.b., of a non-reducing saccharide-forming enzyme obtained by the method in Example 4-3, and enzymatically reacted at 50° C. for 48 hours, resulting in a conversion of about 75% maltopentaose into α-maltotriosyltrehalose. The reaction mixture was heated at 97° C. for 30 min to inactivate the remaining enzyme, and then cooled, filtered, and purified by decoloration using an activated charcoal and desalting using ion exchangers.

Thereafter, the resulting solution was concentrated into an about 75 w/w % solution with respect to solid contents, admixed with an about 0.01 w/v α-maltotriosyltrehalose crystal as a seed crystal, and allowed to stand for 24 hours. Then the crystallized α-maltotriosyltrehalose crystal was collected by a centrifuge, washed with a small amount of cold water, and dried in a usual manner to obtain a crystalline powder with a relatively-high content of the non-reducing saccharide in a yield of about 50% to the material solids, d.s.b.

The product, having a relatively-low sweetness and an extremely-low DE of less than 0.2 and containing at least 99.0 w/w % of α-maltotriosyltrehalose as a non-reducing saccharide, can be arbitrarily used as a taste-improving agent, quality-improving agent, stabilizer, filler, adjuvant or excipient in compositions in general such as foods, cosmetics, and pharmaceuticals.

EXAMPLE 8-5

Process for Producing Hydrous Crystalline Trehalose

Corn starch was suspended in water into a 30 w/w % starch suspension which was then admixed with calcium carbonate in an amount of 0.1 w/w %. The mixture was adjusted to pH 6.0, and then admixed with 0.2 w/w % per starch, d.s.b., of "TERMAMYL 60L", a liquefying α-amylase specimen commercialized by Novo Nordisk Industri A/S, Copenhagen, Denmark, and enzymatically reacted at 95° C. for 15 min to gelatinize and liquefy the starch. The resulting mixture was autoclaved at 120° C. for 30 min, cooled to 51° C., adjusted to pH 5.7, and enzymatically reacted at the same temperature for 64 hours after admixed with 300 units/g starch, d.s.b., of an isoamylase specimen commercialized by Hayashibara Biochemical Laboratories Inc., Okayama, Japan; two units/g starch, d.s.b., of a cyclomaltodextrin glucanotransferase specimen commercialized by Hayashibara Biochemical Laboratories Inc., Okayama, Japan; two units of a non-reducing saccharide-forming enzyme obtained by the method in Example 4-1; and 10 unit/g starch, d.s.b., of a trehalose-releasing enzyme obtained by the method in Example 7-1. The reaction mixture was heated at 97° C. for 30 min to inactivate the remaining enzyme, and then cooled 50° C., admixed with 10 unit/g starch, d.s.b., of "GLUCOZYME", a glucoamylase specimen commercialized by Nagase Biochemicals, Ltd., Kyoto, Japan, and subjected to an enzymatic reaction for 24 hours. The reaction mixture thus obtained was heated at 95° C. for 10 min to inactivate the remaining enzymes, cooled, filtered, purified by decoloration using an activated charcoal and desalting using ion exchangers, and concentrated to an about 60 w/w % solution with respect to solid contents or a syrup containing 84.1 w/w % trehalose, d.s.b. The syrup was concentrated up to give a concentration of about 83 w/w %, d.s.b., and the concentrate was placed in a crystallizer, admixed with an about 0.1 w/v % hydrous crystalline trehalose to the syrup, and stirred for about two hours to crystallize the saccharide. The resulting crystals were collected by a centrifuge, washed with a small amount of water to remove molasses, dried by air heated to 45° C. to obtain hydrous crystalline trehalose with a purity of at least 99% in a yield of about 50% to the material starch, d.s.b.

Since the product is substantially free from hygroscopicity and easily handleable, it can be arbitrarily used as a sweetener, taste-improving agent, quality-improving agent, stabilizer, filler, adjuvant or excipient in compositions in general such as foods, cosmetics, and pharmaceuticals.

EXAMPLE 8-6

Process for Producing Crystalline Powder Containing Anhydrous Crystalline Trehalose Using the method in Example 8-5 hydrous crystalline trehalose was prepared, and the saccharide was dried in vacuo using a jacketed rotary-vacuum-dryer. The drying was conducted at 90° C. and 300-350 mmHg for about seven hours. After the drying, the above temperature and pressure were returned to ambient temperature and normal pressure before collecting the product or a crystalline powder containing at least 90 w/w % anhydrous crystalline trehalose, d.s.b.

Since anhydrous crystalline trehalose absorbs moisture in hydrous matters and changes in itself into hydrous crystalline trehalose, the product rich in the saccharide can be arbitrarily used as a non-harmful safe desiccant to dehydrate or dry compositions including food products, cosmetics and pharmaceuticals, as well as materials and intermediates thereof. The product with a mild and high-quality sweetness can be arbitrarily used as a sweetener, taste-improving agent, quality-improving agent, stabilizer, filler, adjuvant or excipient in compositions in general such as foods, cosmetics, and pharmaceuticals.

EXAMPLE 8-7

Process for Producing Trehalose Syrup

A 27 w/w % suspension of tapioca starch was admixed with calcium carbonate to give a final concentration of 0.1 w/w %, adjusted to pH 6.0, admixed with 0.2 w/w % per starch, d.s.b., of "TERMAMYL 60L", a liquefying α-amylase specimen commercialized by Novo Nordisk Industri A/S, Copenhagen, Denmark, and enzymatically reacted at 95° C. for 15 min to gelatinize and liquefy the starch. The resulting mixture was autoclaved at a pressure of 2 kg/cm² for 30 min, cooled to 53° C., adjusted to pH 5.7, and enzymatically reacted at the same temperature for 72 hours after admixed with 500 units/g starch, d.s.b., of "PROMOZYME 200L", a pullulanase specimen commercialized by Novo Nordisk Industri A/S, Copenhagen, Denmark; one unit/g starch, d.s.b., of *Pseudomonas stutzeri* strain commercialized by Hayashibara Biochemical Laboratories Inc., Okayama, Japan; about two units/g starch, d.s.b., of a non-reducing saccharide-forming enzyme and about six units/g starch, d.s.b., of a trehalose-releasing enzyme, obtained by the method in Example 7-2. The reaction mixture thus obtained was heated at 97° C. for 15 min, cooled and filtered to obtain a filtrate. The filtrate was in a usual manner purified by decoloration using an activated charcoal and desalting using ion exchangers, and concentrated to an about 70 w/w % syrup with respect to solid contents in a yield of about 92% to the material, d.s.b.

The product, comprising 35.2% trehalose, 3.4% α-glucosyltrehalose, 1.8% glucose, 37.2% maltose, 9.1% maltotriose, and 13.3% oligosaccharides higher than maltotetraose, has a mild and high-quality sweetness, relatively-lower reducibility and viscosity, and adequate moisture-retaining ability; it can be arbitrarily used as a sweetener, taste-improving agent, quality-improving agent, stabilizer, filler, adjuvant or excipient in compositions in general such as foods, cosmetics, and pharmaceuticals.

EXAMPLE 8-8

Process for Producing Crystalline Powder Containing Anhydrous Crystalline Trehalose One part by weight of "EX-I", an amylose commercialized by Hayashibara Biochemical Laboratories Inc., Okayama, Japan, was dissolved in 15 parts by weight of water by heating, and the solution was heated to 53° C. and adjusted to pH 5.7. To the resulting solution was added two units/g amylose, d.s.b., of a non-reducing saccharide-forming enzyme, obtained in Example 4-3, and six units/g amylose, d.s.b., of a trehalose-releasing enzyme, obtained by the method in Example 7-4, followed by an incubation for 48 hours. The reaction mixture was heated at 97° C. for 30 min to inactivate the remaining enzyme, and then adjusted to pH 5.0, admixed with 10 units/g amylose, d.s.b., of "GLUCOZYME", a glucoamylase specimen commercialized by Nagase Biochemicals, Ltd., Kyoto, and enzymatically reacted for 40 hours. The reaction mixture thus obtained was heated at 95° C. for 10 min to inactivate the remaining enzymes, cooled, filtered, purified by decoloration using an activated charcoal and desalting using ion exchangers, and concentrated to an about 60 w/w % solution with respect to solid contents or a syrup containing 82.1 w/w % trehalose, d.s.b.

Similarly as in Example 8-3, the syrup was subjected to column chromatography, followed by collecting a fraction containing about 98 w/w % trehalose, d.s.b. The fraction was concentrated in vacuo under heating conditions into an about 85 w/w % syrup with respect to solid contents. The syrup was admixed with hydrous crystalline trehalose as a seed crystal in an about 2 w/v % of to the syrup, stirred at 120° C. for five minutes, distributed to plastic vats, and dried at 100° C. in vacuo to crystallize the saccharide. Thereafter, the contents in a block form were detached from the vats and cut with a cutter to obtain a solid product, containing anhydrous crystalline trehalose with a crystallinity of about 70% and having a moisture content of about 0.3 w/w % in a yield of about 70% to the material amylose, d.s.b. The solid product was pulverized in a usual manner into a crystalline powdery containing anhydrous crystalline trehalose.

Since anhydrous crystalline trehalose absorb moisture from hydrous matters and changes into hydrous crystalline trehalose, the product rich in anhydrous crystalline trehalose can be arbitrarily used as a non-harmful safe desiccant to dehydrate or dry compositions including food products, cosmetics and pharmaceuticals, as well as materials and intermediates thereof. The product with a mild and high-quality sweetness can be arbitrarily used as a sweetener, taste-improving agent, quality-improving agent, stabilizer, filler, adjuvant or excipient in compositions in general such as foods, cosmetics, and pharmaceuticals.

As described above, the present invention was made based on the finding of a novel non-reducing saccharide-forming enzyme and a novel trehalose-releasing enzyme, which have an optimum temperature in a medium temperature range and preferably have an optimum pH in an acid pH range. These enzymes according to the present invention can be obtained in a desired amount, for example, by culturing microorganisms capable of producing the enzymes. The present DNAs which encode either of the enzymes are quite useful in producing such enzymes as recombinant proteins. In cases of using transformant introduced with the DNAs, the enzymes according to the present invention can be yielded in a desired amount. The present enzymes can be used in producing non-reducing saccharides having a trehalose structure, which include trehalose, in a medium temperature rang and/or an acid pH range. Particularly, when used the present enzymes in combination with other saccharide-related enzymes having an optimum temperature in a medium temperature rang and/or an optimum pH in an acid pH range, desired saccharides can be produced quite efficiently. The enzymes according to the present invention are ones with revealed amino acid sequences; they can be safely used to produce the non-reducing saccharides to be used in food products and pharmaceuticals. The non-reducing saccharides and reducing saccharides, which contain the same and have a lesser reducibility, produced by the present invention have a mild and high-quality sweetness, and most preferably have an insubstantial reducibility or a reduced reducibility by a large margin. Therefore, the saccharides can be arbitrarily used as in compositions in general such as foods, cosmetics, and pharmaceuticals with lesser fear of coloration and deterioration.

The present invention with these unfathomable advantageous properties and features is a useful invention that would greatly contribute to this art.

While there has been described what is at present considered to be the preferred embodiments of the invention, it will be understood that various modifications may be made therein, and it is intended to cover in the appended claims all such modifications as fall within the true spirit and scope of the invention.

What is claimed is:

1. A purified trehalose-releasing enzyme which hydrolyzes a non-reducing saccharide having a trehalose structure as an end unit to release said trehalose end unit from the rest of said non-reducing saccharide and which has an optimum temperature of over 45° C. but below 60° C., wherein said enzyme comprises the amino acid sequence of SEQ ID NO:9.

2. The purified trehalose-releasing enzyme of claim 1, wherein said enzyme consists of the amino acid sequence of SEQ ID NO:9.

3. The purified trehalose-releasing enzyme of claim 1, which has the following physicochemical properties:

(1) Action

Hydrolyzing a non-reducing saccharide having a trehalose structure as an end unit to release said trehalose end unit from the rest of said non-reducing saccharide;

(2) Molecular weight

About 62,000±5,000 daltons on sodium dodecyl sulfate-polyacrylamide gel electrophoresis (SDS-PAGE);

(3) Optimum temperature

About 50° C. to about 55° C. when incubated at pH 6.0 for 30 min;

(4) Optimum pH

About 6.0 when incubated at 50° C. for 30 min;

(5) Thermal stability

Stable up to a temperature of about 50° C. when incubated at pH 7.0 for 60 min; and (6) pH stability Stable at pHs of about 4.5 to about 10.0 when incubated at 4° C. for 24 hours.

4. The purified trehalose-releasing enzyme of claim 1, which is isolated from a microorganism.

5. The purified trehalose-releasing enzyme of claim 4, wherein said microorganism is a member of the genus *Arthrobacter*.

6. The purified trehalose-releasing enzyme of claim 4, wherein said microorganism is *Arthrobacter* sp. S34, deposited under accession no. FERM BP-6450.

7. The purified trehalose-releasing enzyme of claim 1 obtainable from *Arthrobacter* sp. S34, deposited under accession no. FERM BP-6450.

8. A purified trehalose-releasing enzyme which hydrolyzes a non-reducing saccharide having a trehalose structure as an end unit to release said trehalose end unit from the rest of said non-reducing saccharide and which has an optimum temperature of over 45° C. but below 60° C., wherein said enzyme is a fragment of an enzyme consisting of the amino acid sequence of SEQ ID NO:9.

9. The purified trehalose-releasing enzyme of claim 8, wherein said fragment comprises the amino acid sequence of SEQ ID NO:10, SEQ ID NO:11, SEQ ID NO:12 or SEQ ID NO:13.

10. The purified trehalose-releasing enzyme of claim 8, wherein said fragment comprises the amino acid sequence of SEQ ID NO:14, SEQ ID NO:15, or SEQ ID NO:16.

11. The purified trehalose-releasing enzyme of claim 8, which has the following physicochemical properties:
   (1) Action
      Hydrolyzing a non-reducing saccharide having a trehalose structure as an end unit to release said trehalose end unit from the rest of said non-reducing saccharide;
   (2) Molecular weight
      About 62,000±5,000 daltons on sodium dodecyl sulfate-polyacrylamide gel electrophoresis (SDS-PAGE);
   (3) Optimum temperature
      About 50° C. to about 55° C. when incubated at pH 6.0 for 30 min;
   (4) Optimum pH
      About 6.0 when incubated at 50° C. for 30 min;
   (5) Thermal stability
      Stable up to a temperature of about 50° C. when incubated at pH 7.0 for 60 min; and
   (6) pH stability
      Stable at pHs of about 4.5 to about 10.0 when incubated at 4° C. for 24 hours.

12. The purified trehalose-releasing enzyme of claim 8, which is isolated from a microorganism.

13. The purified trehalose-releasing enzyme of claim 8 obtainable from *Arthrobacter* sp. S34, deposited under accession no. FERM BP-6450.

* * * * *

SEQUENCE LISTING

```
<160> NUMBER OF SEQ ID NOS: 39

<210> SEQ ID NO 1
<211> LENGTH: 756
<212> TYPE: PRT
<213> ORGANISM: ARTHROBACTER sp.S34

<400> SEQUENCE: 1

Pro Ala Ser Thr Tyr Arg Leu Gln Ile Ser Ala Glu Phe Thr Leu Phe
1               5                   10                  15
```

```
Asp Ala Ala Arg Ile Val Pro Tyr Leu His Arg Leu Gly Ala Asp Trp
            20                  25                  30

Leu Tyr Leu Ser Pro Leu Leu Glu Ser Glu Gly Ser Ser His Gly
        35                  40                  45

Tyr Asp Val Val Asp His Ser Arg Val Asp Ala Ala Arg Gly Gly Pro
    50                  55                  60

Glu Gly Leu Ala Glu Leu Ser Arg Ala Ala His Glu Arg Gly Met Gly
65                  70                  75                  80

Val Val Val Asp Ile Val Pro Asn His Val Gly Val Ala Thr Pro Lys
                85                  90                  95

Ala Asn Arg Trp Trp Trp Asp Val Leu Ala Arg Gly Gln Arg Ser Glu
            100                 105                 110

Tyr Ala Asp Tyr Phe Asp Ile Asp Trp Glu Phe Gly Gly Arg Leu
        115                 120                 125

Arg Leu Pro Val Leu Gly Asp Gly Pro Asp Glu Leu Asp Ala Leu Arg
130                 135                 140

Val Asp Gly Asp Glu Leu Val Tyr Tyr Glu His Arg Phe Pro Ile Ala
145                 150                 155                 160

Glu Gly Thr Gly Gly Gly Thr Pro Arg Glu Val His Asp Arg Gln His
            165                 170                 175

Tyr Glu Leu Met Ser Trp Arg Arg Ala Asp His Asp Leu Asn Tyr Arg
        180                 185                 190

Arg Phe Phe Ala Val Asn Thr Leu Ala Ala Val Arg Val Glu Asp Pro
    195                 200                 205

Arg Val Phe Asp Asp Thr His Arg Glu Ile Gly Arg Trp Ile Ala Glu
210                 215                 220

Gly Leu Val Asp Gly Leu Arg Val Asp His Pro Asp Gly Leu Arg Ala
225                 230                 235                 240

Pro Gly Asp Tyr Leu Arg Arg Leu Ala Glu Leu Ala Gln Gly Arg Pro
            245                 250                 255

Ile Trp Val Glu Lys Ile Ile Glu Gly Asp Glu Arg Met Pro Pro Gln
        260                 265                 270

Trp Pro Ile Ala Gly Thr Thr Gly Tyr Asp Ala Leu Ala Gly Ile Asp
    275                 280                 285

Arg Val Leu Val Asp Pro Ala Gly Glu His Pro Leu Thr Gln Ile Val
290                 295                 300

Asp Glu Ala Ala Gly Ser Pro Arg Arg Trp Ala Glu Leu Val Pro Glu
305                 310                 315                 320

Arg Lys Arg Ala Val Ala Arg Gly Ile Leu Asn Ser Glu Ile Arg Arg
            325                 330                 335

Val Ala Arg Glu Leu Gly Glu Val Ala Gly Asp Val Glu Asp Ala Leu
        340                 345                 350

Val Glu Ile Ala Ala Leu Ser Val Tyr Arg Ser Tyr Leu Pro Phe
    355                 360                 365

Gly Arg Glu His Leu Asp Glu Ala Val Ala Ala Gln Ala Ala
370                 375                 380

Pro Gln Leu Glu Ala Asp Leu Ala Ala Val Gly Ala Ala Leu Ala Asp
385                 390                 395                 400

Pro Gly Asn Pro Ala Ala Leu Arg Phe Gln Gln Thr Ser Gly Met Ile
            405                 410                 415

Met Ala Lys Gly Val Glu Asp Asn Ala Phe Tyr Arg Tyr Pro Arg Leu
        420                 425                 430
```

```
Thr Ser Leu Thr Glu Val Gly Gly Asp Pro Ser Leu Phe Ala Ile Asp
        435                 440                 445

Ala Ala Ala Phe His Ala Ala Gln Arg Asp Arg Ala Ala Arg Leu Pro
    450                 455                 460

Glu Ser Met Thr Thr Leu Thr Thr His Asp Thr Lys Arg Ser Glu Asp
465                 470                 475                 480

Thr Arg Ala Arg Ile Thr Ala Leu Ala Glu Ala Pro Glu Arg Trp Arg
                485                 490                 495

Arg Phe Leu Thr Glu Val Gly Gly Leu Ile Gly Thr Gly Asp Arg Val
            500                 505                 510

Leu Glu Asn Leu Ile Trp Gln Ala Ile Val Gly Ala Trp Pro Ala Ser
        515                 520                 525

Arg Glu Arg Leu Glu Ala Tyr Ala Leu Lys Ala Ala Arg Glu Ala Gly
    530                 535                 540

Glu Ser Thr Asp Trp Ile Asp Gly Asp Pro Ala Phe Glu Glu Arg Leu
545                 550                 555                 560

Thr Arg Leu Val Thr Val Ala Val Glu Glu Pro Leu Val His Glu Leu
                565                 570                 575

Leu Glu Arg Leu Val Asp Glu Leu Thr Ala Ala Gly Tyr Ser Asn Gly
            580                 585                 590

Leu Ala Ala Lys Leu Leu Gln Leu Leu Ala Pro Gly Thr Pro Asp Val
        595                 600                 605

Tyr Gln Gly Thr Glu Arg Trp Asp Arg Ser Leu Val Asp Pro Asp Asn
    610                 615                 620

Arg Arg Pro Val Asp Phe Ala Ala Ala Ser Glu Leu Leu Asp Arg Leu
625                 630                 635                 640

Asp Gly Gly Trp Arg Pro Pro Val Asp Glu Thr Gly Ala Val Lys Thr
                645                 650                 655

Leu Val Val Ser Arg Ala Leu Arg Leu Arg Arg Asp Arg Pro Glu Leu
            660                 665                 670

Phe Thr Ala Tyr His Pro Val Thr Ala Arg Gly Ala Gln Ala Glu His
        675                 680                 685

Leu Ile Gly Phe Asp Arg Gly Gly Ala Ile Ala Leu Ala Thr Arg Leu
    690                 695                 700

Pro Leu Gly Leu Ala Ala Ala Gly Gly Trp Gly Asp Thr Val Val Asp
705                 710                 715                 720

Val Gly Glu Arg Ser Leu Arg Asp Glu Leu Thr Gly Arg Glu Ala Arg
                725                 730                 735

Gly Ala Ala Arg Val Ala Glu Leu Phe Ala Asp Tyr Pro Val Ala Leu
            740                 745                 750

Leu Val Glu Thr
        755

<210> SEQ ID NO 2
<211> LENGTH: 6
<212> TYPE: PRT
<213> ORGANISM: ARTHROBACTER sp.S34

<400> SEQUENCE: 2

Asp Ile Val Pro Asn His
1               5

<210> SEQ ID NO 3
<211> LENGTH: 6
<212> TYPE: PRT
<213> ORGANISM: ARTHROBACTER sp.S34
```

<400> SEQUENCE: 3

Gly Thr Thr Gly Tyr Asp
1               5

<210> SEQ ID NO 4
<211> LENGTH: 20
<212> TYPE: PRT
<213> ORGANISM: ARTHROBACTER sp.S34

<400> SEQUENCE: 4

Pro Ala Ser Thr Tyr Arg Leu Gln Ile Ser Ala Glu Phe Thr Leu Phe
1               5                   10                  15

Asp Ala Ala Arg
            20

<210> SEQ ID NO 5
<211> LENGTH: 20
<212> TYPE: PRT
<213> ORGANISM: ARTHROBACTER sp.S34

<400> SEQUENCE: 5

Ser Leu Val Asp Pro Asp Asn Arg Arg Pro Val Asp Phe Ala Ala Ala
1               5                   10                  15

Ser Glu Leu Leu
            20

<210> SEQ ID NO 6
<211> LENGTH: 20
<212> TYPE: PRT
<213> ORGANISM: ARTHROBACTER sp.S34

<400> SEQUENCE: 6

Ala Asn Arg Trp Trp Trp Asp Val Leu Ala Arg Gly Gln Arg Ser Glu
1               5                   10                  15

Tyr Ala Asp Tyr
            20

<210> SEQ ID NO 7
<211> LENGTH: 2268
<212> TYPE: DNA
<213> ORGANISM: ARTHROBACTER sp.S34

<400> SEQUENCE: 7
cccgccagta cctaccgcct tcagatctcg gcggagttca ccctcttcga cgcggcgcgc      60
atcgtgccct acctgcaccg cctcggcgcc gactggctgt acctctcgcc gctgctcgag     120
tccgagtcgg gctcctcgca cggctacgac gtggtcgacc actcccgcgt cgacgccgcc     180
cgcggcgggc cggaggggct cgccgagctc tcccgtgcgg cgcacgagcg cggcatgggc     240
gtcgtcgtcg acatcgtgcc caaccacgtc ggcgtcgcga cgccgaaggc gaaccgctgg     300
tggtgggacg ttctggcccg tggacagcgg tcggagtacg ccgactactt cgacatcgac     360
tgggagttcg cggcggcag gctgcgcctg cccgtgctcg cgacggcccc gacgagctc      420
gacgcgctga gagtggatgg cgacgagctc gtctactacg agcaccgctt cccgatcgcc     480
gagggcaccg gcgcggcac cccgcgcgag gtgcacgacc ggcagcacta cgagctgatg     540
tcgtggcggc gggccgacca cgacctcaac taccgccgct tcttcgccgt gaacacgctc     600
gccgccgtac gcgtcgaaga cccgcgcgtg ttcgacgaca cccaccgcga gatcggccgc     660
tggatcgccg agggcctcgt cgacggcctg gcgtcgacc accccgacgg gctgcgcgcc     720

-continued

```
cccggcgact acctgcgccg tctcgccgag ctcgcccaag gcaggccgat ctgggtcgag    780
aagatcatcg agggcgacga gcggatgccc ccgcagtggc ccatcgccgg caccaccggc    840
tacgacgcgc tggccgggat cgaccgggtg ctcgtcgacc ccgcgggcga gcatccgctc    900
acccagatcg tcgacgaggc ggcaggcagc ccccggcgct gggccgagct ggttcccgag    960
cgcaagcggg ccgtcgcccg cggcatcctg aactccgaga tccgccgcgt cgcccgcgaa   1020
ctcggagagg tcgccggcga cgtcgaagac gcgctcgtcg agatcgccgc cgccctgtcc   1080
gtctaccgca gctacctgcc gttcgggcgc gagcacctcg acgaagccgt ggccgccgcg   1140
caggccgcag ccccccagct cgaggccgac ctcgccgccg tcggcgcagc gctcgccgac   1200
ccgggcaacc ccgccgcgct ccgcttccag cagaccagcg gcatgatcat ggccaagggc   1260
gtcgaggaca acgcgttcta ccgctacccc cggctcacct cgctgaccga ggtcggggga   1320
gacccgagcc tgttcgcgat cgacgcggcc gccttccacg cggcgcagcg cgaccgcgcc   1380
gcccggctgc ccgagtcgat gacgacgctg accacccacg acaccaagcg cagcgaagac   1440
acccgggcgc ggatcaccgc gctcgccgag gcccccgaac gctggcggcg cttcctgacc   1500
gaggtcggcg ggctcatcgg aacgggcgac cgggtgctgg agaacctgat ctggcaggcg   1560
atcgtcggcg cgtggccggc gagccggagc cggctcgagg cctacgcgct gaaggccgcg   1620
cgcgaagccg gcgagtcgac cgactggatc gacggcgacc ccgcgttcga agagcggctg   1680
acccgcctgg tcacggtcgc cgtcgaggag ccgctcgtgc acgagctgct cgagcggctc   1740
gtcgacgagc tgacggcggc cgggtactcc aacggcctcg cggcgaagct gctgcagctg   1800
ctcgcccccg gaaccccga cgtgtaccag ggcacggaac gctgggaccg gtcgctggtg   1860
gacccggaca ccgtcgcccc gtggatttc gccgcggcat ccgagctgct cgaccgcctc   1920
gacggcggct ggcggccgcc cgtcgacgag accggcgcgg tcaagacgct cgtcgtctcc   1980
cgcgcgctgc ggctgcgccg cgaccggccc gagctgttca ccgcgtacca cccggtcacg   2040
gcgcgcggcg cgcaggccga gcacctgatc ggcttcgacc gcggcggcgc gatcgccctg   2100
gccacccgcc tgccgctcgg cctcgccgcc gcaggcggct ggggcgacac ggtcgtcgac   2160
gtcggcgagc ggagcctgcg cgacgagctg accggccgcg aggcccgcgg agcggcgcgc   2220
gtggccgagt tgttcgccga ctaccccgtc gccctgctgg tggagaca               2268
```

```
<210> SEQ ID NO 8
<211> LENGTH: 28
<212> TYPE: DNA
<213> ORGANISM: ARTHROBACTER sp.S34

<400> SEQUENCE: 8
ttttttaata aaatcaggag gaaaaaat                                         28

<210> SEQ ID NO 9
<211> LENGTH: 575
<212> TYPE: PRT
<213> ORGANISM: ARTHROBACTER sp.S34

<400> SEQUENCE: 9

Met Asn Arg Arg Phe Pro Val Trp Ala Pro Gln Ala Ala Gln Val Thr
1               5                   10                  15

Leu Val Val Gly Gln Gly Arg Ala Glu Leu Pro Leu Thr Arg Asp Glu
            20                  25                  30

Asn Gly Trp Trp Ala Leu Gln Gln Pro Trp Asp Gly Gly Pro Asp Leu
        35                  40                  45
```

```
Val Asp Tyr Gly Tyr Leu Val Asp Gly Lys Gly Pro Phe Ala Asp Pro
 50                  55                  60

Arg Ser Leu Arg Gln Pro Arg Gly Val His Glu Leu Gly Arg Glu Phe
 65                  70                  75                  80

Asp Pro Ala Arg Tyr Ala Trp Gly Asp Gly Trp Arg Gly Arg Asp
                 85                  90                  95

Leu Thr Gly Ala Val Ile Tyr Glu Leu His Val Gly Thr Phe Thr Pro
                100                 105                 110

Glu Gly Thr Leu Asp Ser Ala Ile Arg Arg Leu Asp His Leu Val Arg
                115                 120                 125

Leu Gly Val Asp Ala Val Glu Leu Leu Pro Val Asn Ala Phe Asn Gly
                130                 135                 140

Thr His Gly Trp Gly Tyr Asp Gly Val Leu Trp Tyr Ala Val His Glu
145                 150                 155                 160

Pro Tyr Gly Gly Pro Glu Ala Tyr Gln Arg Phe Val Asp Ala Cys His
                165                 170                 175

Ala Arg Gly Leu Ala Val Val Gln Asp Val Val Tyr Asn His Leu Gly
                180                 185                 190

Pro Ser Gly Asn His Leu Pro Asp Phe Gly Pro Tyr Leu Gly Ser Gly
                195                 200                 205

Ala Ala Asn Thr Trp Gly Asp Ala Leu Asn Leu Asp Gly Pro Leu Ser
                210                 215                 220

Asp Glu Val Arg Arg Tyr Ile Ile Asp Asn Ala Val Tyr Trp Leu Arg
225                 230                 235                 240

Asp Met His Ala Asp Gly Leu Arg Leu Asp Ala Val His Ala Leu Arg
                245                 250                 255

Asp Ala Arg Ala Leu His Leu Leu Glu Leu Ala Ala Arg Val Asp
                260                 265                 270

Glu Leu Ala Gly Glu Leu Gly Arg Pro Leu Thr Leu Ile Ala Glu Ser
                275                 280                 285

Asp Leu Asn Asp Pro Lys Leu Ile Arg Ser Arg Ala Ala His Gly Tyr
290                 295                 300

Gly Leu Asp Ala Gln Trp Asp Asp Val His His Ala Val His Ala
305                 310                 315                 320

Asn Val Thr Gly Glu Thr Val Gly Tyr Tyr Ala Asp Phe Gly Gly Leu
                325                 330                 335

Gly Ala Leu Val Lys Val Phe Gln Arg Gly Trp Phe His Asp Gly Thr
                340                 345                 350

Trp Ser Ser Phe Arg Glu Arg His His Gly Arg Pro Leu Asp Pro Asp
                355                 360                 365

Ile Pro Phe Arg Arg Leu Val Ala Phe Ala Gln Asp His Asp Gln Val
                370                 375                 380

Gly Asn Arg Ala Val Gly Asp Arg Met Ser Ala Gln Val Gly Glu Gly
385                 390                 395                 400

Ser Leu Ala Ala Ala Ala Leu Val Leu Gly Pro Phe Thr Pro
                405                 410                 415

Met Leu Phe Met Gly Glu Glu Trp Gly Ala Arg Thr Pro Trp Gln Phe
                420                 425                 430

Phe Thr Ser His Pro Glu Pro Glu Leu Gly Glu Ala Thr Ala Arg Gly
                435                 440                 445

Arg Ile Ala Glu Phe Ala Arg Met Gly Trp Asp Pro Ala Val Val Pro
450                 455                 460
```

```
Asp Pro Gln Asp Pro Ala Thr Phe Ala Arg Ser His Leu Asp Trp Ser
465                 470                 475                 480

Glu Pro Glu Arg Glu Pro His Ala Gly Leu Leu Ala Phe Tyr Thr Asp
            485                 490                 495

Leu Ile Ala Leu Arg Arg Glu Leu Pro Val Asp Ala Pro Ala Arg Glu
        500                 505                 510

Val Asp Ala Asp Glu Ala Arg Gly Val Phe Ala Phe Ser Arg Gly Pro
    515                 520                 525

Leu Arg Val Thr Val Ala Leu Arg Pro Gly Pro Val Gly Val Pro Glu
    530                 535                 540

His Gly Gly Leu Val Leu Ala Tyr Gly Glu Val Arg Ala Gly Ala Ala
545                 550                 555                 560

Gly Leu His Leu Asp Gly Pro Gly Ala Ala Ile Val Arg Leu Glu
                565                 570                 575

<210> SEQ ID NO 10
<211> LENGTH: 6
<212> TYPE: PRT
<213> ORGANISM: ARTHROBACTER sp.S34

<400> SEQUENCE: 10

Trp Gly Tyr Asp Gly Val
1               5

<210> SEQ ID NO 11
<211> LENGTH: 6
<212> TYPE: PRT
<213> ORGANISM: ARTHROBACTER sp.S34

<400> SEQUENCE: 11

Asp Val Val Tyr Asn His
1               5

<210> SEQ ID NO 12
<211> LENGTH: 7
<212> TYPE: PRT
<213> ORGANISM: ARTHROBACTER sp.S34

<400> SEQUENCE: 12

Arg Leu Asp Ala Val His Ala
1               5

<210> SEQ ID NO 13
<211> LENGTH: 7
<212> TYPE: PRT
<213> ORGANISM: ARTHROBACTER sp.S34

<400> SEQUENCE: 13

Ile Ala Glu Ser Asp Leu Asn
1               5

<210> SEQ ID NO 14
<211> LENGTH: 20
<212> TYPE: PRT
<213> ORGANISM: ARTHROBACTER sp.S34

<400> SEQUENCE: 14

Met Asn Arg Arg Phe Pro Val Trp Ala Pro Gln Ala Ala Gln Val Thr
1               5                   10                  15

Leu Val Val Gly
            20
```

<210> SEQ ID NO 15
<211> LENGTH: 20
<212> TYPE: PRT
<213> ORGANISM: ARTHROBACTER sp.S34

<400> SEQUENCE: 15

Ser Arg Ala Ala His Gly Tyr Gly Leu Asp Ala Gln Trp Asp Asp
1               5                   10                  15

Val His His Ala
            20

<210> SEQ ID NO 16
<211> LENGTH: 20
<212> TYPE: PRT
<213> ORGANISM: ARTHROBACTER sp.S34

<400> SEQUENCE: 16

Asp Glu Asn Gly Trp Trp Ala Leu Gln Gln Pro Trp Asp Gly Gly Pro
1               5                   10                  15

Asp Leu Val Asp
            20

<210> SEQ ID NO 17
<211> LENGTH: 1725
<212> TYPE: DNA
<213> ORGANISM: ARTHROBACTER sp.S34

<400> SEQUENCE: 17

```
atgaaccgac gattcccggt ctgggcgccc caggccgcgc aggtgacgct cgtcgtgggc      60
caaggccgcg ccgaactccc gctgacccgc gacgagaacg gatggtgggc tcttcagcag     120
ccgtgggacg gcggccccga cctcgtcgac tacggctacc tcgtcgacgg caagggcccc     180
ttcgccgacc gcggtcgct gcggcagccg cgcggcgtgc acgagctcgg ccgcgaattc     240
gaccccgccc gctacgcgtg gggcgacgac ggatggcgcg gccgagacct caccggagcc     300
gtgatctacg aactgcacgt cggcaccttc acccctgagg aacgctggga cagcgccatc     360
cgtcgcctcg accacctggt gcgcctcggc gtcgacgcgg tcgagctgct gcccgtcaac     420
gcgttcaacg gcacccacgg ctggggctac gacggggtgc tctggtacgc ggtgcacgag     480
ccctacggcg gcccggaggc gtaccagcgc ttcgtcgacg cctgccacgc ccgcggcctc     540
gccgtcgtgc aggacgtcgt ctacaaccac ctgggcccga gcggcaacca cctgcccgac     600
ttcggcccct acctcgggtc gggcgccgcc aacacctggg gcgacgcgct gaacctcgac     660
gggccgctct ccgacgaggt gcggcggtac atcatcgaca acgcggtgta ctggctgcgc     720
gacatgcacg ccgacgggct gcggctcgac gccgtgcacg cgctgcgcga cgcccgcgcg     780
ctgcacctgc tcgaagagct cgccgcccgc gtcgacgagc tggcgggcga gctcggccgg     840
ccgctgacgc tcatcgccga gagcgacctg aacgacccga gctgatccg ctcccgcgcg     900
gcgcacggct acggcctcga cgcccagtgg gacgacgacg tgcaccacgc ggtgcacgcc     960
aacgtgaccg cgcgagaccgt cggctactac gccgacttcg gcgggctcgg cgccctcgtc    1020
aaggtgttcc agcgcggctg gttccacgac ggcacctggt cgagcttccg cgagcggcac    1080
cacgccggc cgctcgaccc cgacatcccg ttccgccggc tcgtcgcctt cgcgcaggat    1140
cacgaccagg tcggcaaccg agcggtcggc gaccgcatgt cggcgcaggt cggcgagggt    1200
tcgctcgccg ccgcggcggc gctcgtgctg ctcggcccgt tcaccccgat gctgttcatg    1260
ggcgaggagt ggggcgcgcg caccccgtgg cagttcttca cctcccaccc cgagcccgag    1320
```

-continued

```
ctgggggagg cgacggcgcg cgggcgcatc gccgagttcg cccgcatggg ctgggacccg    1380
gcagtcgtgc ccgacccgca ggacccggcc accttcgccc gctcgcacct ggactggtcc    1440
gagcccgagc gggaaccgca cgcggggcctg ctcgccttct acaccgacct gatcgcgctg   1500
cggcgcgagc tgccggtcga tgcgccggcg cgcgaggtgg atgccgacga ggcgcgcggc    1560
gtcttcgcgt tcagccgcgg cccgctgcgg gtcacggtcg cgctgcgccc cggaccggtc    1620
ggggtgcccg agcacggggg cctcgtgctc gcctacggcg aggtgcgcgc cggcgccgcc    1680
ggactgcacc tcgacgggcc gggagccgcg atcgtgcgcc tcgag                    1725
```

```
<210> SEQ ID NO 18
<211> LENGTH: 23
<212> TYPE: DNA
<213> ORGANISM: ARTHROBACTER sp.S34

<400> SEQUENCE: 18
gcsaaccgst ggtggtggga cgt                                              23

<210> SEQ ID NO 19
<211> LENGTH: 3252
<212> TYPE: DNA
<213> ORGANISM: ARTHROBACTER sp.S34
<220> FEATURE:
<221> NAME/KEY: 5'UTR
<222> LOCATION: (1)..(742)
<220> FEATURE:
<221> NAME/KEY: 3'UTR
<222> LOCATION: (742)..(3014)
<220> FEATURE:
<221> NAME/KEY: CDS
<222> LOCATION: (743)..(3013)

<400> SEQUENCE: 19
```

```
atgccgacga cgaacttgag cgcgttctcg ggcacccgcg agagcggtcc gcgcacggcg    60
gcgcccagtg ccacgacgag cacgatcgcg gcgagcgccg cgacgacggc gaccggcagg    120 cgccctgat tgctggcgaa ggtgagcacg atgaagacca cctcgaggcc ctcgagcaac    180
acacctttga acgacacggt gaacgcgtac caatcggaga ccccgaaccg gctctcgcgc    240
cgggcgctct cggccgcctc gacctgacgc cggaaggcag cctcctcgtc acggagagcc    300
ctgcgccctg ccgcgcgcag caccgccttg cgcagccagc cgagcccgaa gacgagcagc    360
aacccgccga cgacgaggcg cagcacggcc agcggcagca gcaggatcgc gggaccgacg    420
agcgcgacgg ccgcggccag caccaccacg gcgacggcgg cacctgtcag cgccgaccgc    480
cagctgcggg tggcgccgac cgcgacgacg atcgtggtcg cctccaccgc ctcgaccacg    540
caggcgagga acacggcggc gaacagggcg acggcggtca tcggcccagc agacggttga    600
ccatcacggc acgctagcgc cattgctcac aggaagggcc aagacgcccg caacgcggca    660
cccgtggacg gcgcgtaccg gcgtgtgacc gatcgtgtca accggtggcg cccgccccga    720
```

```
gcacctgcgt agattcggcc tc gtg ccc gcc agt acc tac cgc ctt cag atc      772
                        Val Pro Ala Ser Thr Tyr Arg Leu Gln Ile
                          1               5                  10 tcg gcg gag ttc acc ctc ttc gac gcg gcg cgc atc gtg ccc tac ctg       820
Ser Ala Glu Phe Thr Leu Phe Asp Ala Ala Arg Ile Val Pro Tyr Leu
                 15                  20                  25 cac cgc ctc ggc gcc gac tgg ctg tac ctc tcg ccg ctg ctc gag tcc       868
His Arg Leu Gly Ala Asp Trp Leu Tyr Leu Ser Pro Leu Leu Glu Ser
         30                  35                  40 gag tcg ggc tcc tcg cac ggc tac gac gtg gtc gac cac tcc cgc gtc       916
```

|  |  |
|---|---|
| Glu Ser Gly Ser Ser His Gly Tyr Asp Val Val Asp His Ser Arg Val<br>            45                     50                  55 |  |
| gac gcc gcc cgc ggc ggg ccg gag ggg ctc gcc gag ctc tcc cgt gcg<br>Asp Ala Ala Arg Gly Gly Pro Glu Gly Leu Ala Glu Leu Ser Arg Ala<br>   60                      65                    70 | 964 |
| gcg cac gag cgc ggc atg ggc gtc gtc gtc gac atc gtg ccc aac cac<br>Ala His Glu Arg Gly Met Gly Val Val Val Asp Ile Val Pro Asn His<br>75                    80                    85                    90 | 1012 |
| gtc ggc gtc gcg acg ccg aag gcg aac cgc tgg tgg tgg gac gtt ctg<br>Val Gly Val Ala Thr Pro Lys Ala Asn Arg Trp Trp Trp Asp Val Leu<br>                      95                      100                  105 | 1060 |
| gcc cgt gga cag cgg tcg gag tac gcc gac tac ttc gac atc gac tgg<br>Ala Arg Gly Gln Arg Ser Glu Tyr Ala Asp Tyr Phe Asp Ile Asp Trp<br>                 110                     115                  120 | 1108 |
| gag ttc ggc ggc ggc agg ctg cgc ctg ccc gtg ctc ggc gac ggc ccc<br>Glu Phe Gly Gly Gly Arg Leu Arg Leu Pro Val Leu Gly Asp Gly Pro<br>         125                      130                      135 | 1156 |
| gac gag ctc gac gcg ctg aga gtg gat ggc gac gag ctc gtc tac tac<br>Asp Glu Leu Asp Ala Leu Arg Val Asp Gly Asp Glu Leu Val Tyr Tyr<br>       140                      145                      150 | 1204 |
| gag cac cgc ttc ccg atc gcc gag ggc acc ggc ggc acc ccg cgc<br>Glu His Arg Phe Pro Ile Ala Glu Gly Thr Gly Gly Thr Pro Arg<br>155                    160                    165                  170 | 1252 |
| gag gtg cac gac cgg cag cac tac gag ctg atg tcg tgg cgg gcc<br>Glu Val His Asp Arg Gln His Tyr Glu Leu Met Ser Trp Arg Arg Ala<br>                 175                     180                  185 | 1300 |
| gac cac gac ctc aac tac cgc cgc ttc ttc gcc gtg aac acg ctc gcc<br>Asp His Asp Leu Asn Tyr Arg Arg Phe Phe Ala Val Asn Thr Leu Ala<br>             190                     195                  200 | 1348 |
| gcc gta cgc gtc gaa gac ccg cgc gtg ttc gac gac acc cac cgc gag<br>Ala Val Arg Val Glu Asp Pro Arg Val Phe Asp Asp Thr His Arg Glu<br>         205                      210                    215 | 1396 |
| atc ggc cgc tgg atc gcc gag ggc ctc gtc gac ggc ctg cgc gtc gac<br>Ile Gly Arg Trp Ile Ala Glu Gly Leu Val Asp Gly Leu Arg Val Asp<br>   220                      225                      230 | 1444 |
| cac ccc gac ggg ctg cgc gcc ccc ggc gac tac ctg cgc cgt ctc gcc<br>His Pro Asp Gly Leu Arg Ala Pro Gly Asp Tyr Leu Arg Arg Leu Ala<br>235                    240                    245                  250 | 1492 |
| gag ctc gcc caa ggc agg ccg atc tgg gtc gag aag atc atc gag ggc<br>Glu Leu Ala Gln Gly Arg Pro Ile Trp Val Glu Lys Ile Ile Glu Gly<br>                 255                     260                  265 | 1540 |
| gac gag cgg atg ccc ccg cag tgg ccc atc gcc ggc acc acc ggc tac<br>Asp Glu Arg Met Pro Pro Gln Trp Pro Ile Ala Gly Thr Thr Gly Tyr<br>             270                     275                  280 | 1588 |
| gac gcg ctg gcc ggg atc gac cgg gtg ctc gtc gac ccc gcg ggc gag<br>Asp Ala Leu Ala Gly Ile Asp Arg Val Leu Val Asp Pro Ala Gly Glu<br>       285                      290                    295 | 1636 |
| cat ccg ctc acc cag atc gtc gac gag gcg gca ggc agc ccc cgg cgc<br>His Pro Leu Thr Gln Ile Val Asp Glu Ala Ala Gly Ser Pro Arg Arg<br>         300                      305                    310 | 1684 |
| tgg gcc gag ctg gtt ccc gag cgc aag cgg gcc gtc gcc cgg ggc atc<br>Trp Ala Glu Leu Val Pro Glu Arg Lys Arg Ala Val Ala Arg Gly Ile<br>315                    320                    325                  330 | 1732 |
| ctg aac tcc gag atc cgc cgc gtc gcc cgc gaa ctc gga gag gtc gcc<br>Leu Asn Ser Glu Ile Arg Arg Val Ala Arg Glu Leu Gly Glu Val Ala<br>                 335                     340                  345 | 1780 |
| ggc gac gtc gaa gac gcg ctc gtc gag atc gcc gcc gcc ctg tcc gtc<br>Gly Asp Val Glu Asp Ala Leu Val Glu Ile Ala Ala Ala Leu Ser Val<br>             350                     355                  360 | 1828 |

```
tac cgc agc tac ctg ccg ttc ggg cgc gag cac ctc gac gaa gcc gtg      1876
Tyr Arg Ser Tyr Leu Pro Phe Gly Arg Glu His Leu Asp Glu Ala Val
        365                 370                 375 gcc gcg cag gcc gca gcc ccc cag ctc gag gcc gac ctc gcc gcc          1924
Ala Ala Gln Ala Ala Ala Pro Gln Leu Glu Ala Asp Leu Ala Ala
380                 385                 390 gtc ggc gca gcg ctc gcc gac ccg ggc aac ccc gcc gcg ctc cgc ttc      1972
Val Gly Ala Ala Leu Ala Asp Pro Gly Asn Pro Ala Ala Leu Arg Phe
395                 400                 405                 410 cag cag acc agc ggc atg atc atg gcc aag ggc gtc gag gac aac gcg      2020
Gln Gln Thr Ser Gly Met Ile Met Ala Lys Gly Val Glu Asp Asn Ala
                415                 420                 425 ttc tac cgc tac ccc cgg ctc acc tcg ctg acc gag gtc ggg gga gac      2068
Phe Tyr Arg Tyr Pro Arg Leu Thr Ser Leu Thr Glu Val Gly Gly Asp
            430                 435                 440 ccg agc ctg ttc gcg atc gac gcg gcc gcc ttc cac gcg gcg cag cgc      2116
Pro Ser Leu Phe Ala Ile Asp Ala Ala Ala Phe His Ala Ala Gln Arg
        445                 450                 455 gac cgc gcc gcc cgg ctg ccc gag tcg atg acg acg ctg acc acc cac      2164
Asp Arg Ala Ala Arg Leu Pro Glu Ser Met Thr Thr Leu Thr Thr His
460                 465                 470 gac acc aag cgc agc gaa gac acc cgg gcg cgg atc acc gcg ctc gcc      2212
Asp Thr Lys Arg Ser Glu Asp Thr Arg Ala Arg Ile Thr Ala Leu Ala
475                 480                 485                 490 gag gcc ccc gaa cgc tgg cgg cgc ttc ctg acc gag gtc ggc ggg ctc      2260
Glu Ala Pro Glu Arg Trp Arg Arg Phe Leu Thr Glu Val Gly Gly Leu
                495                 500                 505 atc gga acg ggc gac cgg gtg ctg gag aac ctg atc tgg cag gcg atc      2308
Ile Gly Thr Gly Asp Arg Val Leu Glu Asn Leu Ile Trp Gln Ala Ile
            510                 515                 520 gtc ggc gcg tgg ccg gcg agc cgg gag cgg ctc gag gcc tac gcg ctg      2356
Val Gly Ala Trp Pro Ala Ser Arg Glu Arg Leu Glu Ala Tyr Ala Leu
        525                 530                 535 aag gcc gcg cgc gaa gcc ggc gag tcg acc gac tgg atc gac ggc gac      2404
Lys Ala Ala Arg Glu Ala Gly Glu Ser Thr Asp Trp Ile Asp Gly Asp
540                 545                 550 ccc gcg ttc gaa gag cgg ctg acc cgc ctg gtc acg gtc gcc gtc gag      2452
Pro Ala Phe Glu Glu Arg Leu Thr Arg Leu Val Thr Val Ala Val Glu
555                 560                 565                 570 gag ccg ctc gtg cac gag ctg ctc gag cgg ctc gtc gac gag ctg acg      2500
Glu Pro Leu Val His Glu Leu Leu Glu Arg Leu Val Asp Glu Leu Thr
                575                 580                 585 gcg gcc ggg tac tcc aac ggc ctc gcg gcg aag ctg ctg cag ctg ctc      2548
Ala Ala Gly Tyr Ser Asn Gly Leu Ala Ala Lys Leu Leu Gln Leu Leu
            590                 595                 600 gcc ccc gga acc ccc gac gtg tac cag ggc acg gaa cgc tgg gac cgg      2596
Ala Pro Gly Thr Pro Asp Val Tyr Gln Gly Thr Glu Arg Trp Asp Arg
        605                 610                 615 tcg ctg gtg gac ccg gac aac cgt cgc ccc gtg gat ttc gcc gcg gca      2644
Ser Leu Val Asp Pro Asp Asn Arg Arg Pro Val Asp Phe Ala Ala Ala
620                 625                 630 tcc gag ctg ctc gac cgc ctc gac ggc ggc tgg cgg ccg ccc gtc gac      2692
Ser Glu Leu Leu Asp Arg Leu Asp Gly Gly Trp Arg Pro Pro Val Asp
635                 640                 645                 650 gag acc ggc gcg gtc aag acg ctc gtc gtc tcc cgc gcg ctg cgg ctg      2740
Glu Thr Gly Ala Val Lys Thr Leu Val Val Ser Arg Ala Leu Arg Leu
                655                 660                 665 cgc cgc gac cgg ccc gag ctg ttc acc gcg tac cac ccg gtc acg gcg      2788
Arg Arg Asp Arg Pro Glu Leu Phe Thr Ala Tyr His Pro Val Thr Ala
            670                 675                 680
```

```
cgc ggc gcg cag gcc gag cac ctg atc ggc ttc gac cgc ggc ggc gcg     2836
Arg Gly Ala Gln Ala Glu His Leu Ile Gly Phe Asp Arg Gly Gly Ala
        685                 690                 695 atc gcc ctg gcc acc cgc ctg ccg ctc ggc ctc gcc gcc gca ggc ggc     2884
Ile Ala Leu Ala Thr Arg Leu Pro Leu Gly Leu Ala Ala Ala Gly Gly
    700                 705                 710 tgg ggc gac acg gtc gtc gac gtc ggc gag cgg agc ctg cgc gac gag     2932
Trp Gly Asp Thr Val Val Asp Val Gly Glu Arg Ser Leu Arg Asp Glu
715                 720                 725                 730 ctg acc ggc cgc gag gcc cgc gga gcg gcg cgc gtg gcc gag ttg ttc     2980
Leu Thr Gly Arg Glu Ala Arg Gly Ala Ala Arg Val Ala Glu Leu Phe
            735                 740                 745 gcc gac tac ccc gtc gcc ctg ctg gtg gag aca tgaaccgacg attcccggtc   3033
Ala Asp Tyr Pro Val Ala Leu Leu Val Glu Thr
            750                 755 tgggcgcccc aggccgcgca ggtgacgctc gtcgtgggcc aaggccgcgc cgaactcccg    3093
ctgacccgcg acgagaacgg atggtgggct cttcagcagc cgtgggacgg cggccccgac    3153
ctcgtcgact acggctacct cgtcgacgga agggcccct tcgccgaccc gcggtcgctg     3213
cggcagccgc gcggcgtgca cgagctcggc cgcgaattc                           3252

<210> SEQ ID NO 20
<211> LENGTH: 26
<212> TYPE: DNA
<213> ORGANISM: Artificial
<220> FEATURE:
<223> OTHER INFORMATION: synthetic

<400> SEQUENCE: 20
atgcccgcca gtacctaccg ccttca                                         26

<210> SEQ ID NO 21
<211> LENGTH: 25
<212> TYPE: DNA
<213> ORGANISM: Artificial
<220> FEATURE:
<223> OTHER INFORMATION: synthetic

<400> SEQUENCE: 21
tcatgtctcc accagcaggg cgacg                                          25

<210> SEQ ID NO 22
<211> LENGTH: 50
<212> TYPE: DNA
<213> ORGANISM: Artificial
<220> FEATURE:
<223> OTHER INFORMATION: synthetic

<400> SEQUENCE: 22 aattctttt taataaaatc aggaggaatc tagatgttta ctagtctgca                50

<210> SEQ ID NO 23
<211> LENGTH: 42
<212> TYPE: DNA
<213> ORGANISM: Artificial
<220> FEATURE:
<223> OTHER INFORMATION: synthetic

<400> SEQUENCE: 23
gactagtaaa catctagatt cctcctgatt ttattaaaaa ag                       42

<210> SEQ ID NO 24
```

```
<211> LENGTH: 33
<212> TYPE: DNA
<213> ORGANISM: Artificial
<220> FEATURE:
<223> OTHER INFORMATION: synthetic

<400> SEQUENCE: 24
aaatctagat gcccgccagt acctaccgcc ttc                         33

<210> SEQ ID NO 25
<211> LENGTH: 33
<212> TYPE: DNA
<213> ORGANISM: Artificial
<220> FEATURE:
<223> OTHER INFORMATION: synthetic

<400> SEQUENCE: 25
aaaactagtt tatcatgtct ccaccagcag ggc                         33

<210> SEQ ID NO 26
<211> LENGTH: 22
<212> TYPE: DNA
<213> ORGANISM: Artificial
<220> FEATURE:
<223> OTHER INFORMATION: synthetic

<400> SEQUENCE: 26
atcggtgatg tcggcgatat ag                                     22

<210> SEQ ID NO 27
<211> LENGTH: 29
<212> TYPE: DNA
<213> ORGANISM: Artificial
<220> FEATURE:
<223> OTHER INFORMATION: synthetic

<400> SEQUENCE: 27
gtactggcgg gcatattttt tcctcctga                              29

<210> SEQ ID NO 28
<211> LENGTH: 31
<212> TYPE: DNA
<213> ORGANISM: Artificial
<220> FEATURE:
<223> OTHER INFORMATION: synthetic

<400> SEQUENCE: 28
aatcaggagg aaaaaatatg cccgccagta c                           31

<210> SEQ ID NO 29
<211> LENGTH: 22
<212> TYPE: DNA
<213> ORGANISM: Artificial
<220> FEATURE:
<223> OTHER INFORMATION: synthetic

<400> SEQUENCE: 29
tcgacgatct gggtgagcgg at                                     22

<210> SEQ ID NO 30
<211> LENGTH: 22
<212> TYPE: DNA
<213> ORGANISM: Artificial
<220> FEATURE:
<223> OTHER INFORMATION: synthetic

<400> SEQUENCE: 30
```

-continued

```
tcgacgagca cccggtcgat cc                                                    22

<210> SEQ ID NO 31
<211> LENGTH: 26
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (18)..(18)
<223> OTHER INFORMATION: n is a, c, g, or t

<400> SEQUENCE: 31
cartgggayg aygaygtnca ycaygc                                                26

<210> SEQ ID NO 32
<211> LENGTH: 2218
<212> TYPE: DNA
<213> ORGANISM: Artificial
<220> FEATURE:
<223> OTHER INFORMATION: synthetic
<220> FEATURE:
<221> NAME/KEY: CDS
<222> LOCATION: (477)..(2201)
<220> FEATURE:
<221> NAME/KEY: 3'UTR
<222> LOCATION: (2202)..(2218)

<400> SEQUENCE: 32
ctgcagctgc tcgcccccgg aaccccgac gtgtaccagg gcacggaacg ctgggaccgg           60
tcgctggtgg acccggacaa ccgtcgcccc gtggatttcg ccgcggcatc cgagctgctc         120
gaccgcctcg acggcggctg gcggccgccc gtcgacgaga ccggcgcggt caagacgctc         180
gtcgtctccc gcgcgctgcg gctgcgccgc gaccggcccg agctgttcac cgcgtaccac         240
ccggtcacgg cgcgcggcgc gcaggccgag cacctgatcg gcttcgaccg cggcggcgcg         300
atcgccctgg ccacccgcct gccgctcggc ctcgccgccg caggcggctg ggcgacacg          360 gtcgtcgacg tcggcgagcg gagcctgcgc gacgagctga ccggccgcga ggcccgcgga         420
gcggcgcgcg tggccgagtt gttcgccgac taccccgtcg ccctgctggt ggagac atg        479
                                                                    Met
                                                                    1 aac cga cga ttc ccg gtc tgg gcg ccc cag gcc gcg cag gtg acg ctc           527
Asn Arg Arg Phe Pro Val Trp Ala Pro Gln Ala Ala Gln Val Thr Leu
        5                   10                  15 gtc gtg ggc caa ggc cgc gcc gaa ctc ccg ctg acc cgc gac gag aac           575
Val Val Gly Gln Gly Arg Ala Glu Leu Pro Leu Thr Arg Asp Glu Asn
    20                  25                  30 gga tgg tgg gct ctt cag cag ccg tgg gac ggc ggc ccc gac ctc gtc           623
Gly Trp Trp Ala Leu Gln Gln Pro Trp Asp Gly Gly Pro Asp Leu Val
35                  40                  45 gac tac ggc tac ctc gtc gac ggc aag ggc ccc ttc gcc gac ccg cgg           671
Asp Tyr Gly Tyr Leu Val Asp Gly Lys Gly Pro Phe Ala Asp Pro Arg
50                  55                  60                  65 tcg ctg cgg cag ccg cgc ggc gtg cac gag ctc ggc cgc gaa ttc gac           719
Ser Leu Arg Gln Pro Arg Gly Val His Glu Leu Gly Arg Glu Phe Asp
                70                  75                  80 ccc gcc cgc tac gcg tgg ggc gac gac gga tgg cgc ggc cga gac ctc           767
Pro Ala Arg Tyr Ala Trp Gly Asp Asp Gly Trp Arg Gly Arg Asp Leu
            85                  90                  95 acc gga gcc gtg atc tac gaa ctg cac gtc ggc acc ttc acc cct gag           815
Thr Gly Ala Val Ile Tyr Glu Leu His Val Gly Thr Phe Thr Pro Glu
```

-continued

```
                100                 105                 110
gga acg ctg gac agc gcc atc cgt cgc ctc gac cac ctg gtg cgc ctc      863
Gly Thr Leu Asp Ser Ala Ile Arg Arg Leu Asp His Leu Val Arg Leu
    115                 120                 125 ggc gtc gac gcg gtc gag ctg ctc ccc gtc aac gcg ttc aac ggc acc      911
Gly Val Asp Ala Val Glu Leu Leu Pro Val Asn Ala Phe Asn Gly Thr
130                 135                 140                 145 cac ggc tgg ggc tac gac ggg gtg ctc tgg tac gcg gtg cac gag ccc      959
His Gly Trp Gly Tyr Asp Gly Val Leu Trp Tyr Ala Val His Glu Pro
                150                 155                 160 tac ggc ggc ccg gag gcg tac cag cgc ttc gtc gac gcc tgc cac gcc     1007
Tyr Gly Gly Pro Glu Ala Tyr Gln Arg Phe Val Asp Ala Cys His Ala
            165                 170                 175 cgc ggc ctc gcc gtc gtg cag gac gtc gtc tac aac cac ctg ggc ccg     1055
Arg Gly Leu Ala Val Val Gln Asp Val Val Tyr Asn His Leu Gly Pro
        180                 185                 190 agc ggc aac cac ctg ccc gac ttc ggc ccc tac ctc ggg tcg ggc gcc     1103
Ser Gly Asn His Leu Pro Asp Phe Gly Pro Tyr Leu Gly Ser Gly Ala
    195                 200                 205 gcc aac acc tgg ggc gac gcg ctg aac ctc gac ggg ccg ctc tcc gac     1151
Ala Asn Thr Trp Gly Asp Ala Leu Asn Leu Asp Gly Pro Leu Ser Asp
210                 215                 220                 225 gag gtg cgg cgg tac atc atc gac aac gcg gtc tac tgg ctg cgc gac     1199
Glu Val Arg Arg Tyr Ile Ile Asp Asn Ala Val Tyr Trp Leu Arg Asp
                230                 235                 240 atg cac gcc gac ggg ctg cgg ctc gac gcc gtg cac gcg ctg cgc gac     1247
Met His Ala Asp Gly Leu Arg Leu Asp Ala Val His Ala Leu Arg Asp
            245                 250                 255 gcc cgc gcg ctg cac ctg ctc gaa gag ctc gcc gcc cgc gtc gac gag     1295
Ala Arg Ala Leu His Leu Leu Glu Glu Leu Ala Ala Arg Val Asp Glu
        260                 265                 270 ctg gcg ggc gag ctc ggc cgg ccg ctg acg ctc atc gcc gag agc gac     1343
Leu Ala Gly Glu Leu Gly Arg Pro Leu Thr Leu Ile Ala Glu Ser Asp
    275                 280                 285 ctg aac gac ccg aag ctg atc cgc tcc cgc gcg gcg cac ggc tac ggc     1391
Leu Asn Asp Pro Lys Leu Ile Arg Ser Arg Ala Ala His Gly Tyr Gly
290                 295                 300                 305 ctc gac gcc cag tgg gac gac gac gtg cac cac gcg gtg cac gcc aac     1439
Leu Asp Ala Gln Trp Asp Asp Asp Val His His Ala Val His Ala Asn
                310                 315                 320 gtg acc ggc gag acc gtc ggc tac tac gcc gac ttc ggc ggg ctc ggc     1487
Val Thr Gly Glu Thr Val Gly Tyr Tyr Ala Asp Phe Gly Gly Leu Gly
            325                 330                 335 gcc ctc gtc aag gtg ttc cag cgc ggc tgg ttc cac gac ggc acc tgg     1535
Ala Leu Val Lys Val Phe Gln Arg Gly Trp Phe His Asp Gly Thr Trp
        340                 345                 350 tcg agc ttc cgc gag cgg cac cac ggc cgg ccg ctc gac ccc gac atc     1583
Ser Ser Phe Arg Glu Arg His His Gly Arg Pro Leu Asp Pro Asp Ile
    355                 360                 365 ccg ttc cgc cgg ctc gtc gcc ttc gcg cag gat cac gac cag gtc ggc     1631
Pro Phe Arg Arg Leu Val Ala Phe Ala Gln Asp His Asp Gln Val Gly
370                 375                 380                 385 aac cga gcg gtc ggc gac cgc atg tcg gcg cag gtc ggc gag ggt tcg     1679
Asn Arg Ala Val Gly Asp Arg Met Ser Ala Gln Val Gly Glu Gly Ser
                390                 395                 400 ctc gcc gcc gcg gcg gcg ctc gtg ctg ctc ggc ccg ttc acc ccg atg     1727
Leu Ala Ala Ala Ala Ala Leu Val Leu Leu Gly Pro Phe Thr Pro Met
            405                 410                 415 ctg ttc atg ggc gag gag tgg ggc gcg cgc acc ccg tgg cag ttc ttc     1775
```

```
                Leu Phe Met Gly Glu Glu Trp Gly Ala Arg Thr Pro Trp Gln Phe Phe
                    420                 425                 430 acc tcc cac ccc gag ccc gag ctg ggg gag gcg acg gcg cgc ggg cgc              1823
Thr Ser His Pro Glu Pro Glu Leu Gly Glu Ala Thr Ala Arg Gly Arg
    435                 440                 445 atc gcc gag ttc gcc cgc atg ggc tgg gac ccg gca gtc gtg ccc gac              1871
Ile Ala Glu Phe Ala Arg Met Gly Trp Asp Pro Ala Val Val Pro Asp
450                 455                 460                 465 ccg cag gac ccg gcc acc ttc gcc cgc tcg cac ctg gac tgg tcc gag              1919
Pro Gln Asp Pro Ala Thr Phe Ala Arg Ser His Leu Asp Trp Ser Glu
                470                 475                 480 ccc gag cgg gaa ccc cac gcg ggc ctg ctc gcc ttc tac acc gac ctg              1967
Pro Glu Arg Glu Pro His Ala Gly Leu Leu Ala Phe Tyr Thr Asp Leu
            485                 490                 495 atc gcg ctg cgg cgc gag ctg ccg gtc gat gcg ccg gcg cgc gag gtg              2015
Ile Ala Leu Arg Arg Glu Leu Pro Val Asp Ala Pro Ala Arg Glu Val
        500                 505                 510 gat gcc gac gag gcg cgc ggc gtc ttc gcg ttc agc cgc ggc ccg ctg              2063
Asp Ala Asp Glu Ala Arg Gly Val Phe Ala Phe Ser Arg Gly Pro Leu
    515                 520                 525 cgg gtc acg gtc gcg ctg cgc ccc gga ccg gtc ggg gtg ccc gag cac              2111
Arg Val Thr Val Ala Leu Arg Pro Gly Pro Val Gly Val Pro Glu His
530                 535                 540                 545 ggg ggc ctc gtg ctc gcc tac ggc gag gtg cgc gcc ggc gcc gcc gga              2159
Gly Gly Leu Val Leu Ala Tyr Gly Glu Val Arg Ala Gly Ala Ala Gly
                550                 555                 560 ctg cac ctc gac ggg ccg gga gcc gcg atc gtg cgc ctc gag                      2201
Leu His Leu Asp Gly Pro Gly Ala Ala Ile Val Arg Leu Glu
                565                 570                 575 tgacgcggct gggtacc                                                           2218

<210> SEQ ID NO 33
<211> LENGTH: 25
<212> TYPE: DNA
<213> ORGANISM: Artificial
<220> FEATURE:
<223> OTHER INFORMATION: synthetic

<400> SEQUENCE: 33
atgaaccgac gattcccggt ctggg                                                  25

<210> SEQ ID NO 34
<211> LENGTH: 25
<212> TYPE: DNA
<213> ORGANISM: Artificial
<220> FEATURE:
<223> OTHER INFORMATION: synthetic

<400> SEQUENCE: 34
tcactcgagg cgcacgatcg cggct                                                  25

<210> SEQ ID NO 35
<211> LENGTH: 36
<212> TYPE: DNA
<213> ORGANISM: Artificial
<220> FEATURE:
<223> OTHER INFORMATION: synthetic

<400> SEQUENCE: 35
aaatctagat gaaccgacga ttcccggtct gggcgc                                      36

<210> SEQ ID NO 36
```

```
<211> LENGTH: 36
<212> TYPE: DNA
<213> ORGANISM: Artificial
<220> FEATURE:
<223> OTHER INFORMATION: synthetic

<400> SEQUENCE: 36
aaaactagtt tatcactcga ggcgcacgat cgcggc                                  36

<210> SEQ ID NO 37
<211> LENGTH: 28
<212> TYPE: DNA
<213> ORGANISM: Artificial
<220> FEATURE:
<223> OTHER INFORMATION: synthetic

<400> SEQUENCE: 37
atcgtcggtt catatttttt cctcctga                                           28

<210> SEQ ID NO 38
<211> LENGTH: 28
<212> TYPE: DNA
<213> ORGANISM: Artificial
<220> FEATURE:
<223> OTHER INFORMATION: synthetic

<400> SEQUENCE: 38
aatcaggagg aaaaaatatg aaccgacg                                           28

<210> SEQ ID NO 39
<211> LENGTH: 22
<212> TYPE: DNA
<213> ORGANISM: Artificial
<220> FEATURE:
<223> OTHER INFORMATION: synthetic

<400> SEQUENCE: 39
aggtggttgt agacgacgtc ct                                                 22
```